United States Patent
Ohara et al.

(10) Patent No.: US 9,394,397 B2
(45) Date of Patent: Jul. 19, 2016

(54) BIOMASS-RESOURCE-DERIVED POLYURETHANE, METHOD FOR PRODUCING SAME, AND BIOMASS-RESOURCE-DERIVED POLYESTER POLYOL

(71) Applicants: Teruhiko Ohara, Tokyo (JP); Naoki Suzuki, Niigata (JP); Yasuko Nakajima, Kanagawa (JP); Hiroto Itou, Mie (JP); Takayuki Aoshima, Kanagawa (JP); Naoki Sugai, Kanagawa (JP); Takanao Matsumoto, Kanagawa (JP)

(72) Inventors: Teruhiko Ohara, Tokyo (JP); Naoki Suzuki, Niigata (JP); Yasuko Nakajima, Kanagawa (JP); Hiroto Itou, Mie (JP); Takayuki Aoshima, Kanagawa (JP); Naoki Sugai, Kanagawa (JP); Takanao Matsumoto, Kanagawa (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 36 days.

(21) Appl. No.: 13/632,992

(22) Filed: Oct. 1, 2012

(65) Prior Publication Data
US 2013/0035448 A1 Feb. 7, 2013

Related U.S. Application Data

(63) Continuation of application No. PCT/JP2011/057984, filed on Mar. 30, 2011.

(30) Foreign Application Priority Data

Mar. 31, 2010 (JP) .................. 2010-082393

(51) Int. Cl.
| | | |
|---|---|---|
| C08G 18/42 | (2006.01) |
| C07C 69/34 | (2006.01) |
| C07C 69/40 | (2006.01) |
| C07C 69/66 | (2006.01) |
| C07C 69/675 | (2006.01) |
| C07C 69/70 | (2006.01) |
| C07C 69/704 | (2006.01) |
| C08G 63/06 | (2006.01) |
| C08G 63/20 | (2006.01) |
| C08G 63/60 | (2006.01) |
| A43B 13/04 | (2006.01) |
| C08G 18/66 | (2006.01) |
| C08G 18/76 | (2006.01) |
| C07C 59/245 | (2006.01) |
| C08G 63/16 | (2006.01) |
| C08G 101/00 | (2006.01) |

(52) U.S. Cl.
CPC ............ *C08G 18/4286* (2013.01); *A43B 13/04* (2013.01); *C07C 59/245* (2013.01); *C07C 69/34* (2013.01); *C07C 69/40* (2013.01); *C07C 69/66* (2013.01); *C07C 69/675* (2013.01); *C07C 69/70* (2013.01); *C07C 69/704* (2013.01); *C08G 18/4238* (2013.01); *C08G 18/4241* (2013.01); *C08G 18/664* (2013.01); *C08G 18/7671* (2013.01); *C08G 63/06* (2013.01); *C08G 63/16* (2013.01); *C08G 63/20* (2013.01); *C08G 63/60* (2013.01); *C08G 2101/0008* (2013.01); *C08G 2410/00* (2013.01)

(58) Field of Classification Search
CPC ........... C08G 18/4241; C08G 18/4286; C08G 18/4238
USPC ....................... 528/80, 83; 521/172
See application file for complete search history.

(56) References Cited

U.S. PATENT DOCUMENTS

| | | | |
|---|---|---|---|
| 5,436,056 A | 7/1995 | Takiyama et al. | |
| 5,688,890 A * | 11/1997 | Ishiguro et al. | 528/51 |
| 2010/0055467 A1 | 3/2010 | Kulfan et al. | |
| 2010/0130633 A1 | 5/2010 | Usaka et al. | |

FOREIGN PATENT DOCUMENTS

| | | |
|---|---|---|
| EP | 1640397 | 3/2006 |
| JP | 2008-94888 A | 4/2008 |
| JP | 2008-274092 | 11/2008 |
| JP | 2009-096824 | 5/2009 |
| JP | 4301918 B2 | 7/2009 |
| WO | WO 2005/030973 A1 * | 4/2005 |
| WO | WO 2005/080307 | 9/2005 |
| WO | 2008/104541 | 9/2008 |
| WO | 2010/035837 | 4/2010 |
| WO | 2011/064151 | 6/2011 |

OTHER PUBLICATIONS

Sax et al.; Hawley's Condensed Chemical Dictionary, Eleventh Edition; Van Nostrand Reinhold; New York; 1987; pp. 1102, 1121.*
International Search Report issued Jul. 19, 2011 in PCT/JP2011/057984.

(Continued)

*Primary Examiner* — Rabon Sergent
(74) *Attorney, Agent, or Firm* — Oblon, McClelland, Maier & Neustadt, L.L.P.

(57) ABSTRACT

The invention relates to a method for producing a biomass-resource-derived polyurethane, which comprises: reacting a dicarboxylic acid and an aliphatic diol to produce a polyester polyol; and reacting the polyester polyol and a polyisocyanate compound, wherein the dicarboxylic acid contains at least one component derived from biomass resources, a content of an organic acid in the dicarboxylic acid is more than 0 ppm and not more than 1,000 ppm relative to the dicarboxylic acid, and a pKa value of the organic acid at 25° C. is not more than 3.7.

6 Claims, No Drawings

(56) References Cited

OTHER PUBLICATIONS

Fundamentals and Applications in Polyurethanes, pp. 96-105, supervised by Matsunaga, by CMC Publishing Co., Ltd., issued in Nov. 2006.
CRC Handbook of Chemistry and Physics, $75^{th}$ Ed., pp. 8-43 to 8-56, CRC Press, (1995).
Kagku-binran (Chemical Handbook) (Basic Ed.), pp. 1054-1059, Maruzen Publishing Co. Ltd. (1966).
JIS-K7105—1981 with English translation.
Combined Chinese Office Action and Search Report issued Dec. 16, 2013, in Chinese Patent Application No. 201180016195.3 with English translation.
Chinese Office Action issued on Aug. 4, 2014, in Patent Application No. 201180016195.3 with English translation.
Japanese Office Action issued on Aug. 5, 2014 in Patent Application No. 2011-073099.
Chinese Office Action issued on Apr. 3, 2015 in corresponding Chinese Patent Application No. 201180016195.3 w/English translation.
Japanese Office Action issued on Aug. 4, 2014 in the corresponding Japanese patent application No. 2015-005341 with English translation.
Extended European Search Report issued Nov. 19, 2015, in corresponding European Patent Application No. 11765620.7 (with English Translation).
Notice of Demand for Agreement issued Oct. 7, 2015, in Korean Patent Application No. 2012-7027895 filed Mar. 30, 2011 and Korean Patent Application No. 2015-7019374 filed Mar. 30, 2011 (with English translation).
Notice of Grounds for Rejection issued Oct. 7, 2015, in Korean Patent Application No. 2012-7027895 filed Mar. 30, 2011 (with English translation).
Final Rejection issued Sep. 29, 2015, in Japanese Patent Application No. 2015-005341 filed Jan. 14, 2015 (with English translation).
Korean Office Action issued Jan. 21, 2016 in corresponding Korean Patent Application No. 2012-7027895, filed Oct. 25, 2012, with English translation (14 pages).
Extended European Search Report issued Feb. 23, 2016, in European Patent Application No. 15184944.5.

\* cited by examiner

SEQUENCE LISTING

```
<160> NUMBER OF SEQ ID NOS: 9

<210> SEQ ID NO 1
<211> LENGTH: 24
<212> TYPE: DNA
<213> ORGANISM: Artificial sequence
<220> FEATURE:
<223> OTHER INFORMATION: primer

<400> SEQUENCE: 1
acgaagtgac tgctatcacc cttg                                      24

<210> SEQ ID NO 2
<211> LENGTH: 23
<212> TYPE: DNA
<213> ORGANISM: Artificial sequence
<220> FEATURE:
<223> OTHER INFORMATION: primer

<400> SEQUENCE: 2
cagaacttta ctgcatccgc aca                                       23

<210> SEQ ID NO 3
<211> LENGTH: 36
<212> TYPE: DNA
<213> ORGANISM: Artificial sequence
<220> FEATURE:
<223> OTHER INFORMATION: primer

<400> SEQUENCE: 3
gtggatgaga caggactatc tagagctaca gtgaca                         36

<210> SEQ ID NO 4
<211> LENGTH: 33
<212> TYPE: DNA
<213> ORGANISM: Artificial sequence
<220> FEATURE:
<223> OTHER INFORMATION: primer

<400> SEQUENCE: 4
agaattgatt ataggtcact aaaactaatt cag                            33

<210> SEQ ID NO 5
<211> LENGTH: 25
<212> TYPE: DNA
<213> ORGANISM: Artificial sequence
<220> FEATURE:
<223> OTHER INFORMATION: primer

<400> SEQUENCE: 5
gtaggtatca cccatgcaca agttg                                     25

<210> SEQ ID NO 6
<211> LENGTH: 23
<212> TYPE: DNA
<213> ORGANISM: Artificial sequence
```

```
<220> FEATURE:
<223> OTHER INFORMATION: primer

<400> SEQUENCE: 6
cctagtatcg taacccccga ttc                                              23

<210> SEQ ID NO 7
<211> LENGTH: 21
<212> TYPE: DNA
<213> ORGANISM: Artificial sequence
<220> FEATURE:
<223> OTHER INFORMATION: primer

<400> SEQUENCE: 7
gttttcccag tcacgacgtt g                                                21

<210> SEQ ID NO 8
<211> LENGTH: 24
<212> TYPE: DNA
<213> ORGANISM: Artificial sequence
<220> FEATURE:
<223> OTHER INFORMATION: primer

<400> SEQUENCE: 8
actggcattg atgtcgatcc agca                                             24

<210> SEQ ID NO 9
<211> LENGTH: 23
<212> TYPE: DNA
<213> ORGANISM: Artificial sequence
<220> FEATURE:
<223> OTHER INFORMATION: primer

<400> SEQUENCE: 9
ctgttgccaa tttgcgaagc tca                                              23
```

BIOMASS-RESOURCE-DERIVED POLYURETHANE, METHOD FOR PRODUCING SAME, AND BIOMASS-RESOURCE-DERIVED POLYESTER POLYOL

TECHNICAL FIELD

The present invention relates to a biopolyurethane derived from novel polyester polyol based biomass resources and a method for producing the same and to a biomass-resource-derived polyester polyol. Specifically, the present invention relates to a polyurethane derived from polyester-polyol-based biomass resources having an excellent balance in physical properties such as mechanical physical properties, molding operability, etc., which are useful for applications over a wide range inclusive of synthetic or artificial leathers, foamed resins for shoe sole, thermoplastic resins, thermosetting resins, paints, laminating adhesives, elastic fibers, and the like, all of which are produced using, as a raw material, a biomass-resource-derived polyester polyol.

BACKGROUND ART

A main soft segment part of polyurethane resins which have been conventionally produced on an industrial scale, namely a polyol, is classified into a polyether type represented by polypropylene glycol and polytetramethylene glycol, a polyester polyol type represented by dicarboxylic acid based polyesters, a polylactone type represented by polycaprolactone, and a polycarbonate type obtained by reacting a carbonate source and a diol (Non-Patent Document 1).

Of these, though the polyether type is excellent in hydrolysis resistance, flexibility, and elasticity, it is considered to be inferior in mechanical strength such as abrasion resistance, flexibility resistance, etc., heat resistance, and weather resistance. On the other hand, though the conventional polyester type is improved in heat resistance and weather resistance, it cannot be used depending upon an application because hydrolysis resistance of an ester segment thereof is low. Though the polylactone type is considered to be a slightly better in hydrolysis resistance as compared with adipates, it is unable to completely suppress the hydrolysis because it similarly has an ester group.

Furthermore, though the polycarbonate type is excellent in hydrolysis resistance and durability, it involves such a drawback that handling operability is poor because a solution viscosity of a polyol itself or a polyurethane produced using this as a raw material is high. In addition, though it is also proposed to use these polyester type, polyether type, polylactone type, and polycarbonate type upon being mixed and copolymerized, the respective drawbacks cannot be completely compensated yet.

In addition, in recent years, global-scale awareness concerning environmental issues is increasing, and raw materials derived from biomass resources such as plants, etc. but not petroleum-derived raw materials affecting the warming of the earth are expected. However, almost all of the foregoing polyols are derived from petroleum exclusive of an extremely part of raw materials.

Furthermore, in polyester polyols which are most widely used at present, polyester polyols synthesized from adipic acid are leading. However, in producing adipic acid, a nitric acid oxidation method is adopted, and there is present an environmental issue that $N_2O$ which is conspicuously large in a warming effect following the production as compared with $CO_2$.

Then, in order to solving these problems, polyester polyols having a variety of structures are proposed. For example, there is a method for forming a polyester polyol by mixing and copolymerizing succinic acid as a dicarboxylic acid other than adipic acid and a diol without adopting nitric acid oxidation for the production thereof, specially a method of co-mixing succinic acid and an oligomer of ethylene glycol (Patent Document 1).

But, though polyester polyols using petroleum-derived succinic acid and polyurethanes produced therefrom are known and industrially produced, the polyester polyols using succinic acid as a raw material are generally poor in handling properties.

For example, the polyester polyols using succinic acid involved such problems that reaction control in the polyurethane reaction is difficult; the molecular weight of a polyurethane resin is liable to increase; in the case of using a polyisocyanate with low reactivity, etc. as a raw material, the polyurethane reaction becomes instable; and the like. In addition, as compared with those produced using generally widely used adipic acid as a raw material, the resulting polyurethane resins have such properties that as a physical property of the resin, are high in hardness and high in elastic modulus of tensile strength, and their applications for use were restricted.

On the other hand, from the viewpoint of protecting the global environment in the recent years, polyurethane resins derived from biomass resources are demanded. However, sebacic acid and castor oil are merely used in small amounts for limited applications, and polyurethane raw materials derived from biomass resources have been expected.

In the recent years, there is disclosed a technology for producing a polyester polyol using, as a raw material, biosuccinic acid obtained by the fermentation method (Patent Document 2). However, a polyurethane using the polyester polyol produced by the technology described in Patent Document 2 merely exhibits mechanical characteristics equal to those in the case of using a polyester polyol produced using, as a raw material, succinic acid derived from petroleum resources.

In the light of the above, according to any of the foregoing methods, the resulting polyester polyols are not ones having a balance of physical properties of the polyester polyol per se, good handling properties, color, and a balance of easiness of reaction control or mechanical physical properties when formed into a polyurethane. Thus, the development thereof has been expected.

RELATED ART DOCUMENT

Non-Patent Document

Non-Patent Document 1: *Fundamentals and Applications in Polyurethanes*, page 96, supervised by MATSUNAGA, Katsuji, published by CMC Publishing Co., Ltd, issued in November 2006

Patent Document

Patent Document 1: JP-A-2009-96824
Patent Document 2: International Publication No. 2008/104541

SUMMARY OF THE INVENTION

Problems to be Solved by the Invention

According to investigations made by the present inventors, in the technology described in Patent Document 1, succinic acid obtained from petroleum resources is used. In general, in a process of producing succinic acid from petroleum resources, malic acid is formed as a by-product and incorporated as an impurity into the succinic acid. But, it was not mentioned that the incorporation of malic acid as an excessive impurity adversely affects physical properties of a polyurethane, such as easiness of reaction control and flexibility.

For example, in succinic acid obtained from petroleum resources, malic acid is in general contained in an amount of from about 1,500 to 5,000 ppm relative to succinic acid, and its content largely varies depending upon a production lot. For that reason, as a result of extensive and intensive investigations, it has become clear that polyurethanes obtained from the subject succinic acid are not constant in physical properties; and that stable operations are hardly achieved in a production step thereof. Furthermore, the fact that that control of the amount of malic acid is important for stable production of a polyurethane using succinic acid as a raw material has been clarified. But, it is not industrially easy to remove this malic acid.

In addition, from a separate viewpoint, it may be considered that malic acid takes on the responsibility of regulating the strength of the polyurethane and regulating a solution viscosity at the time of production, and it is not always unnecessary as a component to be made coexistent with succinic acid. As a result of extensive and intensive investigations, it has become clear that in view of regulating desired performances of the polyurethane, malic acid is a component, the content of which is to be controlled appropriately.

On the other hand, it is known that malic acid is formed as a by-product in producing biosuccinic acid (see International Publication No. 2005/030973). As compared with succinic acid obtained from petroleum resources, the content of malic acid at the time of completion of a fermentation reaction of biosuccinic acid is conspicuously large; however, the content of malic acid is in general reduced in a subsequent purification step.

However, random purification against malic acid does not reach a level of biosuccinic acid to be used as a raw material of a biopolyurethane in a practical level, and in its application, purification to the purpose or any means at the time of a production step or the like are necessary, and it was difficult to achieve practice implementation by merely applying the conventional biosuccinic acid to a biopolyurethane.

For example, Patent Document 2 discloses a biopolyurethane using biosuccinic acid. However, though it is disclosed that the succinic acid raw material to be used for the biopolyurethane is used upon being purified, details regarding its steps and the like are not described.

Then, Patent Document 2 describes that physical properties of the resulting polyester polyol and polyurethane are equal to those in the case of using succinic acid obtained from petroleum resources. That is, according to the usual conventional purification methods, the amount of malic acid cannot be controlled, and it was still difficult to produce a polyurethane in a practically useful level.

In addition, in the biopolyurethane produced by the technology of Patent Document 2, a problem of coloration remains, and it is the present situation that the technology has not reached the production of a biopolyurethane in a practically useful level yet.

Then, in view of the foregoing background art, the present invention has been made, and problems thereof are to provide a polyurethane, in which a molecular weight thereof is easily controllable and which is excellent in mechanical characteristics such as flexibility, etc. and less in coloration, and a biopolyester polyol for producing a biopolyurethane.

Means for Solving the Problems

In order to solve the foregoing problems, the present inventors made extensive and intensive investigations. As a result, it has been found that by controlling a content of a specified organic acid in a biopolyurethane to a specified range, more specifically by strictly controlling an organic acid contained in a dicarboxylic acid and having a pKa value at 25° C. of not more than 3.7 (this organic acid will be hereinafter sometimes referred to simply as "organic acid") during a period of from a production step to production of a polyurethane, thereby enabling one to largely affect a molecular weight in the production of a polyurethane and mechanical physical properties of the resulting polyurethane, such as flexibility, elasticity, etc., a biopolyurethane in a practically useful level, which is excellent in mechanical physical properties, production stability, and the like, and a polyester polyol that is also a raw material of the biopolyurethane are obtained, leading to the present invention.

Specifically, the gist of the present invention is as follows.

1. A method for producing a biomass-resource-derived polyurethane, which comprises: reacting a dicarboxylic acid and an aliphatic diol to produce a polyester polyol; and reacting the polyester polyol and a polyisocyanate compound, wherein the dicarboxylic acid contains at least one component derived from biomass resources, a content of an organic acid in the dicarboxylic acid is more than 0 ppm and not more than 1,000 ppm relative to the dicarboxylic acid, and a pKa value of the organic acid at 25° C. is not more than 3.7.

2. The method for producing a biomass-resource-derived polyurethane according to the item 1 above, wherein the at least one component of the dicarboxylic acid is one derived from biomass resources.

3. The method for producing a biomass-resource-derived polyurethane according to the item 1 or 2 above, wherein the dicarboxylic acid contains succinic acid derived from biomass resources.

4. The method for producing a biomass-resource-derived polyurethane according to any one of the items 1 to 3 above, wherein the organic acid having a pKa value at 25° C. of not more than 3.7 has three or more active hydrogen groups per molecule.

5. The method for producing a biomass-resource-derived polyurethane according to any one of the items 1 to 4 above, wherein the organic acid having a pKa value of the organic acid at 25° C. of not more than 3.7 is at least one member selected from malic acid, tartaric acid, and citric acid.

6. A biomass-resource-derived polyurethane, as obtained by the production method according to any one of the items 1 to 5 above.

7. A biomass-resource-derived polyurethane, which at least comprises, as constituent units, a dicarboxylic acid unit, an aliphatic diol unit, a polyisocyanate unit, and an organic acid unit having a pKa value at 25° C. of not more than 3.7, wherein the dicarboxylic acid contains at least one component derived from biomass resources, and a content of the organic acid unit is more than 0% by mole and not more than 0.09% by mole relative to the dicarboxylic acid unit.

8. The biomass-resource-derived polyurethane according to the item 7 above, wherein the at least one component of the dicarboxylic acid is one derived from biomass resources.

9. The biomass-resource-derived polyurethane according to the item 7 or 8 above, wherein the dicarboxylic acid contains succinic acid derived from biomass resources.

10. The biomass-resource-derived polyurethane according to any one of the items 7 to 9 above, wherein the aliphatic diol unit contains at least one of an ethylene glycol unit and a 1,4-butanediol unit.
11. The biomass-resource-derived polyurethane according to any one of the items 7 to 10 above, wherein the organic acid unit having a pKa value at 25° C. of not more than 3.7 is an organic acid unit having three or more active hydrogen groups per molecule.
12. The biomass-resource-derived polyurethane according to any one of the items 7 to 11 above, wherein the organic acid unit having a pKa value at 25° C. of not more than 3.7 is at least one member selected from malic acid, tartaric acid, and citric acid.
13. The biomass-resource-derived polyurethane according to any one of the items 7 to 12 above, having a YI value (in conformity with JIS-K7105) of not more than 20.
14. The biomass-resource-derived polyurethane according to any one of the items 6 to 13 above, having a molecular weight distribution (Mw/Mn) by the GPC measurement of from 1.5 to 3.5.
15. A biomass-resource-derived polyester polyol for production of a polyurethane, which at least comprises, as constituent units, a dicarboxylic acid unit, an aliphatic diol unit, and an organic acid unit having a pKa value at 25° C. of not more than 3.7, wherein the dicarboxylic acid contains at least one component derived from biomass resources, and a content of the organic acid unit is more than 0% by mole and not more than 0.09% by mole relative to the dicarboxylic acid unit.
16. The biomass-resource-derived polyester polyol according to the item 15 above, wherein the at least one component of the dicarboxylic acid is one derived from biomass resources.
17. The biomass-resource-derived polyester polyol according to the item 15 or 16 above, wherein the dicarboxylic acid contains succinic acid derived from biomass resources.
18. The biomass-resource-derived polyester polyol according to any one of the items 15 to 17 above, having a number average molecular weight of 500 or more and not more than 5,000.
19. The biomass-resource-derived polyester polyol according to any one of the items 15 to 18 above, wherein the organic acid unit is at least one member selected from malic acid, tartaric acid, and citric acid.
20. The biomass-resource-derived polyester polyol according to any one of the items 15 to 19 above, having a value expressed as a Hazen color number (APHA value: in conformity with JIS-K0101) of not more than 50.
21. An artificial leather or synthetic leather, as produced using the biomass-resource-derived polyurethane according to any one of the items 6 to 14 above.
22. A polyurethane for shoe sole, as produced using the biomass-resource-derived polyurethane according to any one of the items 6 to 14 above.

Advantage of the Invention

In the production method of the present invention, in a step of reacting a dicarboxylic acid containing at least one component derived from biomass resources and an aliphatic diol to produce a polyester polyol, a content of an organic acid having a pKa value at 25° C. of not more than 3.7, which is represented by malic acid in the dicarboxylic acid, is controlled to a specified amount or less. In consequence, a polyurethane resin produced using the polyester polyol produced by the subject step can be used for a variety of applications because it has a linear structure and has an excellent color. In addition, as a preferred embodiment, there is brought such an advantage that a polyurethane reaction is easily controllable by mediating a control step (for example, a purification step, etc.) of an organic acid having a pKa value at 25° C. of not more than 3.7.

In addition, the biomass-resource-derived polyurethane according to the present invention, which is produced using the polyester polyol produced by the foregoing step, has such a characteristic feature that it is excellent in flexibility, while keeping mechanical strength and heat resistance that are characteristics of the conventional polyester polyol-derived polyurethane. In addition, the biomass-resource-derived polyurethane according to the present invention also has such characteristic features that a viscosity of the resulting polyurethane solution is low; and that operability of molding or coating is enhanced.

In consequence, for example, artificial or synthetic leathers, polyurethane resins for shoe sole, paints or coating agents, cast polyurethanes, and adhesives or sealants, which are produced using the biomass-resource-derived polyurethane according to the present invention, are flexible and highly elastic and are improved in handling properties, as compared with polyurethanes produced using a polyester polyol using a petroleum-derived succinic acid as a raw material, and they are extremely useful in industry.

Furthermore, in a preferred embodiment, the biomass-resource-derived polyurethane according to the present invention is derived from plants, is an environmentally friendly resin, and is enhanced in biodegradability, and therefore, it is very useful.

MODES FOR CARRYING OUT THE INVENTION

Embodiments of the present invention are hereunder described in detail, but it should not be construed that the present invention is limited to the following embodiments and can be carried out upon being modified within the scope of the gist thereof.
<Biomass-Resource-Derived Polyurethane>
A production method of a biomass-resource-derived polyurethane (in the present description, this polyurethane will be sometimes referred to simply as "biopolyurethane" or "polyurethane") is a method for producing a polyurethane including at least a step of reacting an aliphatic diol and a dicarboxylic acid to produce a polyester polyol; and a step of reacting the polyester polyol and a polyisocyanate compound, wherein the dicarboxylic acid contains at least one component derived from biomass resources, and a content of an organic acid having a pKa value at 25° C. of not more than 3.7 in the dicarboxylic acid is more than 0 ppm and not more than 1,000 ppm.

In addition, the biomass-resource-derived polyurethane according to the present invention is a biomass-resource-derived polyurethane containing, as constituent units, at least an aliphatic diol unit, a dicarboxylic acid unit, a polyisocyanate unit, and an organic acid unit having a pKa value at 25° C. of not more than 3.7, wherein the dicarboxylic acid unit is one derived from biomass resources, and a content of the organic acid unit is more than 0% by mole and not more than 0.09% by mole relative to the dicarboxylic acid unit.

Incidentally, the polyurethane as referred to in the present invention means a polyurethane or a polyurethaneurea unless otherwise restricted, and it has hitherto been known that these two kinds of resins have substantially the same physical properties. On the other hand, so far as a structural characteristic feature is concerned, the polyurethane is one produced using a short-chain polyol as a chain extender, whereas the polyurethaneurea is one produced using a polyamine compound as a chain extender.

(1) Dicarboxylic Acid:

Examples of the dicarboxylic acid component which is used in the present invention (in the present invention, this dicarboxylic acid component will be sometimes referred to simply as "dicarboxylic acid") include aliphatic dicarboxylic acids or mixtures thereof, aromatic dicarboxylic acids or mixtures thereof, aromatic dicarboxylic acids or mixtures thereof, and mixtures of an aromatic dicarboxylic acid and an aliphatic dicarboxylic acid. Of these, those composed mainly of an aliphatic dicarboxylic acid are preferable.

It is meant by the terms "composed mainly of" as referred to in the present invention that in general, the content is preferably 50% by mole or more, more preferably 60% by mole or more, still more preferably 70% by mole or more, and especially preferably 90% by mole or more relative to the total dicarboxylic acid unit.

Examples of the aromatic dicarboxylic acid include terephthalic acid, isophthalic acid, and the like. Examples of the derivative of an aromatic dicarboxylic acid include lower alkyl esters of an aromatic dicarboxylic acid. Specific examples of the lower alkyl ester of an aromatic dicarboxylic acid include methyl esters, ethyl esters, propyl esters, butyl esters, and the like.

Of these, terephthalic acid and isophthalic acid are preferable as the aromatic dicarboxylic acid. In addition, dimethyl terephthalate and dimethyl isophthalate are preferable as the derivative of an aromatic dicarboxylic acid. For example, a desired aromatic polyester polyol polyurethane can be produced by using an arbitrary aromatic dicarboxylic acid as in polyesters of dimethyl terephthalate or 1,4-butanediol.

Examples of the aliphatic dicarboxylic acid include aliphatic dicarboxylic acids or derivatives thereof. In general, the aliphatic dicarboxylic acid preferably has a carbon number of 2 or more and not more than 40. In addition, the aliphatic dicarboxylic acid is preferably a normal chain or alicyclic dicarboxylic acid.

Specific examples of the normal chain or alicyclic dicarboxylic acid having a carbon number of 2 or more and not more than 40 include oxalic acid, succinic acid, glutaric acid, adipic acid, sebacic acid, dodecane diacid, dimer acids, cyclohexanedicarboxylic acids, and the like. Of these, from the standpoint of physical properties of an obtained polymer, the aliphatic dicarboxylic acid is preferably adipic acid, succinic acid, sebacic acid, or a mixture thereof, and especially preferably one composed mainly of succinic acid.

In addition, examples of the derivative of an aliphatic dicarboxylic acid include lower alkyl esters of the foregoing aliphatic dicarboxylic acid, such as methyl esters, ethyl esters, propyl esters, butyl esters, etc., cyclic acid anhydrides of the foregoing aliphatic dicarboxylic acid, such as succinic acid, etc., and the like. Of these, a methyl ester of adipic acid or succinic acid, or a mixture thereof is more preferable as the derivative of an aliphatic dicarboxylic acid.

These dicarboxylic acids can be used solely or in admixture of two or more kinds thereof.

The dicarboxylic acid which is used in the present invention contains at least one component derived from biomass resources. Examples of the preferred component derived from biomass resources, which is contained in the dicarboxylic acid, include adipic acid, succinic acid, and sebacic acid. Of these, succinic acid is especially preferable.

In the present invention, as to the matter that the dicarboxylic acid contains at least one component derived from biomass resources, in the case where the dicarboxylic acid is a single kind, the component may be a mixture of, for example, succinic acid that is a petroleum-derived raw material and, for example, succinic acid derived from biomass resources; and in the case where the dicarboxylic acid is a mixture of two or more kinds thereof, the component may be a mixture in which at least one member of the dicarboxylic acids is one derived from biomass resources, or it may be a mixture of a dicarboxylic acid derived from biomass resources and a dicarboxylic acid as a petroleum-derived raw material.

In the case of a mixture of a dicarboxylic acid derived from biomass resources and a dicarboxylic acid as a petroleum-derived raw material, the dicarboxylic acid derived from biomass resources accounts for preferably 20% by mole or more, more preferably 40% by mole or more, still more preferably 60% by mole or more, and especially preferably 90% by mole or more.

In addition, in the present invention, it is preferable that at least one component of the dicarboxylic acid is one derived from biomass resources. This means that for example, when succinic acid is taken as an example as at least one component of the dicarboxylic acid, the whole of the succinic acid is one derived from biomass resources.

Examples of the biomass resources as referred to in the present invention include those in which solar light energy is converted in a form of starch, sugar, cellulose, or the like due to photosynthesis of plants and stored; animal bodies growing by eating vegetable bodies; products prepared by processing vegetable bodies or animal bodies; and the like.

Of these, vegetable resources are more preferable as the biomass resources. Examples of the vegetable resources include wood, rice straw, chaff, rice bran, old rice, corn, sugar cane, cassava, sago palm, bean curd, corn cob, tapioca, bagasse, vegetable oil dregs, potato, soba, soybean, fats and oils, wastepaper, papermaking residue, aquatic residue, livestock excrement, sewage sludge, food waste, and the like.

Of these, vegetable resources such as wood, rice straw, chaff, rice bran, old rice, corn, sugar cane, cassava, sago palm, bean curd, corn cob, tapioca, bagasse, vegetable oil dregs, potato, soba, soybean, fats and oils, wastepaper, papermaking residue, etc. are preferable; wood, rice straw, chaff, old rice, corn, sugar cane, cassava, sago palm, potato, fats and oils, wastepaper, and papermaking residue are more preferable; and corn, sugar cane, cassava, and sago palm are the most preferable. In general, these biomass resources contain a nitrogen element and a lot of alkali metals and alkaline earth metals such as Na, K, Mg, Ca, etc.

Then, though these biomass resources are not particularly limited, for example, they are derived into a carbon source via a step of a known pretreatment such as a chemical treatment with an acid or an alkali, etc., a biological treatment using a microorganism, a physical treatment, etc. and saccharification.

For example, though there is in general no particular limitation, the foregoing step includes a size reduction step by a pretreatment such as chipping, shaving or grinding of the biomass resources, etc. Furthermore, a pulverization step with a grinder or a mill is included according to the need.

The thus microfabricated biomass resources are further derived into a carbon source via the pretreatment and saccharification step. Specific examples of such a method include chemical methods such as an acid treatment with a strong acid, for example, sulfuric acid, nitric acid, hydrochloric acid, phosphoric acid, etc., an alkali treatment, an ammonia freezing steam explosion method, solvent extraction, a supercritical fluid treatment, an oxidizing agent treatment, etc.; physical methods such as pulverization, a steam explosion method, a microwave treatment, electron beam irradiation, etc.; biological treatments such as hydrolysis with a microorganism or enzymatic treatment.

Examples of the carbon source which is derived from the foregoing biomass resources include fermentable carbohydrates such as hexoses, for example, glucose, mannose, galactose, fructose, sorbose, tagatose, etc.; pentoses, for example, arabinose, xylose, ribose, xylulose, ribulose, etc.; disaccharides or polysaccharides, for example, pentosan, saccharose, starch, cellulose, etc.; fatty acids, for example, butyric acid, caproic acid, caprylic acid, capric acid, lauric acid, myristic acid, palmitic acid, parmitoleic acid, stearic acid, oleic acid, linoleic acid, linolenic acid, monocutinic acid, arachidic acid, eicosenoic acid, arachidonic acid, behenic acid, erucic acid, docosapentaenoic acid, docosahexaenoic acid, lignoceric acid, ceracoreic acid, etc.; polyalcohols, for example, glycerin, mannitol, xylitol, ribitol, etc.; and the like Of these, glucose, maltose, fructose, sucrose, lactose, trehalose, and cellulose are preferable.

A dicarboxylic acid is synthesized using such a carbon source by means of a fermentation method utilizing microbial conversion with a microorganism having production capability of a dicarboxylic acid, a chemical conversion method including a reaction step such as hydrolysis, a dehydration reaction, a hydration reaction, an oxidation reaction, etc., or a combination of the fermentation method and the chemical conversion method. Of these, the fermentation method by means of microbial conversion is preferable.

The microorganism having production capability of a dicarboxylic acid is not particularly limited so far as it is a microorganism having production capability of a dicarboxylic acid. Examples thereof include enterobacteria such as *Escherichia coli*, etc.; bacteria belonging to the genus *bacillus*; coryneform bacteria; and the like. Above all, the use of an aerobic microorganism, a facultative anaerobic microorganism, or a microaerophilic microorganism is preferable.

Examples of the aerobic microorganism include coryneform bacterium, bacteria belonging to the genus *bacillus*, bacteria belong to the genus *rhizobium*, bacteria belonging to the genus *arthrobacter*, bacteria belonging to the genus *mycobacterium*, bacteria belonging to the genus *rhodococcus*, bacteria belonging to the genus *nocardia*, bacteria belonging to the genus *streptomyces*, and the like, with coryneform bacteria being more preferable.

The coryneform bacterium is not particularly limited so far as it is classified into this group, and examples thereof include bacteria belonging to the genus *cornebacterium*, bacteria belonging to the genus *brevibacterium*, bacteria belonging to the genus *arthrobacter*, and the like. Of these, bacteria belonging to the genus *cornebacterium* or genus *brevibacterium* are preferable, and bacteria classified into *Cornebacterium glutamicum, Brevibacterium flavum, Brevibacterium ammoniagenes*, or *Brevibacterium lactofermentum* are more preferable.

In the case of using a succinic acid-producing bacterium as the microorganism having production capability of a dicarboxylic acid, as described in the Examples as described later, it is preferable to use a strain having enhanced pyruvate carboxylase activity and reduced lactate dehydrogenase activity.

Though a reaction condition in the microbial transformation, such as reaction temperature and pressure, etc., depends upon the activity of a microorganism to be chosen such as bacterial cells, fungi, etc., a suitable condition for obtaining a dicarboxylic acid may be chosen depending upon each case.

In the microbial transformation, when the pH becomes low, the metabolic activity of the microorganism decreases, the microorganism stops the activity, the production yield is deteriorated, or the microorganism becomes extinct. Thus, a neutralizing agent is usually used.

In general, the pH within the reaction system is measured by a pH sensor, and the pH is regulated by the addition of a neutralizing agent such that the pH falls within a predetermined range. The pH value is regulated to the range where the activity is most effectively exhibited depending upon the kind of a microorganism to be used. An addition method of the neutralizing agent is not particularly limited, and it may be continuous addition or intermittent addition.

Examples of the neutralizing agent include ammonia, ammonium carbonate, urea, hydroxides of an alkali metal, hydroxides of an alkaline earth metal, carbonates of an alkali metal, and carbonates of an alkaline earth metal. Of these, ammonia, ammonium carbonate, and urea are preferable.

Examples of the hydroxide of an alkali (alkaline earth) metal include NaOH, KOH, $Ca(OH)_2$, $Mg(OH)_2$, etc., and mixtures thereof, and the like. In addition, examples of the carbonate of an alkali (alkaline earth) metal include $Na_2CO_3$, $K_2CO_3$, $CaCO_3$, $MgCO_3$, $NaKCO_3$, etc., and mixtures thereof, and the like.

The pH value is regulated to the range where the activity is most effectively exhibited depending upon the kind of a microorganism to be used. In general, the pH is preferably in the range of from 4 to 10, and more preferably in the range of from about 6 to 9.

A fermentation liquid after the microbial transformation may be properly concentrated while taking into consideration operability or efficiency in the subsequent purification step. Though a concentration method is not particularly limited, examples thereof include a method of circulating an inert gas, a method of distilling off water by heating, a method of distilling off water under reduced pressure, a combination thereof, and the like. In addition, a concentration operation may be either a batch operation or a continuous operation.

Incidentally, in the case of using a fermentation liquid, it is preferable to use the fermentation liquid after removing the microorganism. Though the removal method of a microorganism is not particularly limited, examples thereof include settling separation, centrifugation, filtration separation, a combined method thereof, and the like. The removal of a microorganism is industrially carried out by a method such as centrifugation, membrane filtration separation, etc.

Examples of the centrifugation include centrifugal settling, centrifugal filtration, and the like. In the centrifugation, though its operation condition is not particularly limited, in general, it is preferable to conduct the separation by a centrifugal force of from 100 G to 100,000 G. In addition, both a continuous mode and a batch mode can be adopted for the operation.

In addition, examples of the membrane filtration separation include precise filtration, ultrafiltration, and the like, and these may be combined. Though a material quality of the membrane is not particularly limited, examples thereof include organic membranes such as polyolefins, polysulfines, polyacrylonitrile, polyvinylidene fluoride, etc.; and membranes of an inorganic material such as ceramics, etc. In addition, as an operation method thereof, any of a dead-end type and a cross-flow type can be adopted. In the membrane filtration separation, the microorganism often causes clogging of the membrane, and therefore, a method in which after roughly removing the microorganism by means of centrifugation or the like, membrane filtration is carried out, or other method is adopted, too.

Embodiments of the production method of a dicarboxylic acid are hereunder described in detail. However, these descriptions are representative examples of the embodiments, and it should not be construed that the present invention is limited thereto.

As the representative example of the production method of a dicarboxylic acid, a method for producing a dicarboxylic acid, which includes the following steps I to V, is enumerated.

I. An extraction step of mixing of an aqueous solution containing a dicarboxylic acid and a solvent for achieving phase separation from the aqueous solution and recovering the dicarboxylic acid in the solvent;

II. An extract phase concentration step that is a step of concentrating the dicarboxylic acid recovered in the extraction step, in which a water concentration in the extract phase increases due to the concentration;

III. A crystallization step of depositing the dicarboxylic acid from a liquid after the extract phase concentration step;

IV. A solid-liquid separation step of recovering the dicarboxylic acid deposited in the crystallization step; and V. A crystallization mother liquid recycling step of returning at least a part of a crystallization mother liquid after recovering the dicarboxylic acid obtained in the solid-liquid separation step into any one of the steps before the crystallization step.

An embodiment of each of the steps is hereunder described in detail, but the expressions of a dicarboxylic acid and succinic acid are particularly limited and are applicable to the both.

[I. Extraction Step]

The extraction step is a step in which in producing a dicarboxylic acid from an aqueous solution containing a dicarboxylic acid obtained from biomass resources, the aqueous solution containing a dicarboxylic acid and a solvent for achieving phase separation from the aqueous solution are mixed, and the dicarboxylic acid is recovered in the solvent. In general, the extraction step preferably includes a contact step of mixing an aqueous solution containing a dicarboxylic acid and a solvent for achieving phase separation from the aqueous solution to bring them into contact with each other and a phase separation step of after the contact step, subjecting the liquid to phase separation.

In the phase separation step, the aqueous solution and the solvent are subjected to phase separation from each other. According to circumstances, there is a concern that a phase containing a solid content (hereinafter sometimes referred to as "intermediate phase") is formed at a phase interface, thereby allowing the intermediate phase to make it difficult to separate the solvent phase (hereinafter sometimes referred to as "extract phase") and the aqueous solution phase (hereinafter sometimes referred to as "raffinate phase") from each other, or increasing an amount of impurities incorporated into the extract phase. Here, it is preferable to remove the intermediate phase.

In the case of carrying out the contact step by means of a batch operation, the aqueous solution containing a dicarboxylic acid is added with the solvent capable of achieving phase separation from the aqueous solution; the contents are thoroughly mixed; and thereafter, in the phase separation step, the extract phase, the intermediate phase, and the raffinate phase can be separated and recovered by a method of discharging the extract phase, the intermediate phase, and the raffinate phase from the neighborhoods of the respective phases through outlets, a method of successively discharging the phases from the bottom of a container used for the contact, or other method. The intermediate phase containing a large amount of a solid content can also be discharged together with the extract phase, or can also be discharged together with the raffinate phase.

In addition, for example, in the case of carrying out the contact step by means of a continuous operation, in the phase separation step using a contact apparatus composed of a mixer section having a mixer for contact mixing the aqueous solution containing a dicarboxylic acid and the solvent capable of achieving phase separation from the aqueous solution and a settler section having a settler to be applied to a step of allowing the mixed solution obtained by contact mixing to stand to achieve phase separation (sometimes referred to as "phase separation step") (the contact apparatus is sometimes referred to as "mixer-settler type extractor"), the extract phase, the intermediate phase, and the raffinate phase can be recovered, respectively.

(Solid Content)

In the case of adopting the fermentation method with a microorganism at the time of obtaining a dicarboxylic acid from a raw material derived from biomass resources, in general, polymers having a high-order structure such as proteins, etc. are present as impurities in the fermentation liquid. The proteins, etc. are in general highly soluble in water, and almost all of them are distributed into an aqueous solution phase. However, a material in which the high-order structure thereof breaks and which causes denaturation and is insoluble in both water and a solvent is partly present.

A solid content formed in the extraction process tends to gather in the neighborhood of a liquid-liquid interface. In general, in the batch extraction, even when the solid content is formed in the neighborhood of a liquid-liquid interface, there is no significant problem in the operation so far as the solid content is removed, and the extract phase and the raffinate phase are recovered.

On the other hand, in the continuous extraction, in particular, in a countercurrent multi-stage extraction column, since the solid content is continuously formed, a hindrance is caused in liquid-liquid dispersion or liquid-liquid separation, and there is a concern that not only the stable operation is disturbed, but even the extraction cannot be achieved. In addition, when the liquid containing a solid content flows into the succeeding step, there is a concern that the succeeding step is adversely affected.

For example, since the extract phase containing a dicarboxylic acid as recovered in the extraction step has a low dicarboxylic acid concentration, there may be the case where the extract phase is concentrated. However, when the solid content is present, the solid content attaches onto a heating surface of a reboiler, etc. and gets burnt thereon, thereby deteriorating heat transfer efficiency. Furthermore, the may be the case where a problem occurs on the material quality depending upon the succeeding step.

In addition, in the case of using a dicarboxylic acid as a raw material of the polyester polyol, it becomes clear that a nitrogen atom-containing component greatly participates in the polymer color tone.

Since the solid content contains a large amount of a protein denaturant and also contains a large amount of a nitrogen atom-containing component, when the solid content is incorporate into a final product, there is a possibility that the color tone of the polymer is affected. In consequence, it is preferable to remove the solid content formed in the extraction process by the extraction step.

(Removal of Solid Content)

Though a removal method of the solid content is not particularly restricted, it is preferable to selectively remove only the solid content.

For example, in the batch extraction, the solvent is added to the aqueous solution containing a dicarboxylic acid; the contents are thoroughly mixed; and thereafter, the extract phase, the intermediate phase containing a large amount of the solid content, and the raffinate phase can be separated and recovered, respectively.

In addition, in the continuous extraction, in a mixer-settler type extractor composed of a mixer section having a mixer for mixing the fermentation liquid and the solvent and a settler section for subjecting the mixed liquid to liquid-liquid separation, the extract phase, the intermediate phase containing a large amount of the solid content, and the raffinate phase can be recovered, respectively by the settler.

As the mixer, any system may be adopted so far as the fermentation liquid and the solvent are thoroughly mixed, and examples thereof include a mixing tank, a static mixer, and the like. However, in the case of using a mixing tank, air bubbles dragged into the mixing tank by stirring attach to the produced solid content and conspicuously hinder settling of the solid content in the succeeding settler, and therefore, a care is required to be taken for setting a stirring condition. From the viewpoints of an extent of an operation tolerance range and equipment costs, the mixer is preferably a static mixer.

On the other hand, the type of the settler is not particularly limited. Examples thereof include a type of recovering the extract phase, the intermediate phase, and the raffinate phase, respectively by a single-tank system; and a type of recovering the extract phase, the intermediate phase, and the raffinate phase, respectively by a multi-tank system.

Since the intermediate phase containing a large amount of the solid contains the extract phase and the raffinate phase, the intermediate phase is subjected to solid-liquid separation to separate the solid content and the extract phase and/or the raffinate phase from each other, whereby the extract phase and/or the raffinate phase can be recovered. Though the solid-liquid separation method is not particularly limited, examples thereof include methods such as settling separation, filtration separation, etc.

In the settling separation, the solid content may be subjected to settling separation in a gravitational field, or the solid content may be subjected to settling separation in a centrifugal force field. However, from the standpoint of a settling rate, centrifugal settling separation is preferable. In addition, a system thereof may be either a batch operation or a continuous operation. Examples of a continuous centrifugal settler include a screw decanter and a separation plate type centrifugal settler.

In the filtration separation, its method is classified by a filter material, a filtration pressure, a continuous operation or a batch operation, and the like. However, it is not particularly limited so far as it is able to separate the solid content from the extract phase and/or the raffinate phase. However, an opening of the filter material is preferably 0.1 µm or more and not more than 10 µm. When the opening of the filter material is 0.1 µm or more, a penetrating flux is not excessively small, and it is possible to prevent the matter that it takes an excessive time for the filtration. On the other hand, when the opening of the filter material is not more than 10 µm, the separation of the solid content is sufficient.

In view of the fact that the material quality of the filter material is required to be insoluble in the solvent, it is preferable to use Teflon (registered trademark). In addition, any of a vacuum type, a pressure type, or a centrifugation type can be adopted for the filtration. Furthermore, a system thereof may be either a continuous system or a batch system.

(Contact Apparatus)

As the contact apparatus, any apparatus may be used so far as it is able to allow the aqueous solution containing a dicarboxylic acid and the solvent to come into contact with each other and recover a solvent phase and an aqueous solution phase. However, an apparatus capable of further remove the solid content is preferable. Above all, the above-described mixer-settler type extractor which is simple and easy in operation is preferable.

As the mixer, any system may be useful so far as it is able to thoroughly mix the aqueous solution containing a dicarboxylic acid and the solvent capable of achieving phase separation from the aqueous solution, and examples thereof include a container having a stirrer, a static mixer, and the like. However, in the case of using a container having a stirrer, air bubbles or the like dragged into the container by stirring attach to the produced solid content and conspicuously hinder phase separation of the solid content in the succeeding settler, and therefore, it is preferable to achieve stirring under a condition under which air or the like is not dragged. From the viewpoints of an extent of an operation tolerance range and equipment costs, the mixer is preferably a static mixer.

(Phase Separation Apparatus)

The settler may be any system so far as it is able to achieve phase separation of a liquid obtained after bringing the aqueous solution containing a dicarboxylic acid and the solvent capable of achieving the phase separation from the aqueous solution into contact with each other. Examples thereof include a type of recovering the extract phase, the intermediate phase, and the raffinate phase, respectively by a single-tank system; a type of recovering the extract phase, the intermediate phase, and the raffinate phase, respectively by a multi-tank system; a type of recovering each of the phases by means of centrifugation by a rotation apparatus; and the like.

Since in general, the intermediate phase containing a large amount of the solid content contains at least one liquid selected from a liquid of the extract phase and a liquid of the raffinate phase, the at least one liquid selected from a liquid of the extract phase and a liquid of the raffinate phase can be separated and recovered by subjecting the intermediate phase to phase separation. The recovered liquid can be returned to the step after the phase separation step and can also be reused in the step before the contact step. By reusing the recovered liquid, the production efficiency of the dicarboxylic acid can be enhanced, and therefore, such is preferable.

The solid-liquid separation method is not particularly limited, and examples thereof include settling separation, filtration separation, and the like. In the settling separation, the solid content may be subjected to settling separation in a gravitational field, or the solid content may be subjected to settling separation in a centrifugal force field. Centrifugal settling separation is preferable because the settling rate is increased.

A system of the operation of solid-liquid separation may be either a batch operation or a continuous operation. Examples of a continuous centrifugal settler include a screw decanter and a separation plate type centrifugal settler.

In the filtration separation, its method is classified by a filter material, a filtration pressure, a continuous operation or a batch operation, and the like. However, it is not particularly limited so far as it is able to separate the solid content from the extract phase and/or the raffinate phase. However, an opening of the filter material is preferably 0.1 µm or more and not more than 10 µm. When the opening of the filter material is 0.1 µm or more, a penetrating flux is not excessively small, and it is possible to prevent the matter that it takes an excessive time for the filtration. On the other hand, when the opening of the filter material is not more than 10 µm, the separation of the solid content is sufficient. In addition, since the material quality of the filter material is required to be insoluble in the solvent, it is preferable to use a filter material made of a fluorine based resin such as Teflon, etc.

Any of a vacuum type, a pressure type, or a centrifugation type can be adopted for the filtration. Furthermore, a system thereof may be either a continuous system or a batch system.

(Solvent)

Though the solvent which is used in the contact step is not particularly limited so far as it is able to achieve phase separation from the aqueous solution containing a dicarboxylic acid, an inorganicity/organicity ratio (hereinafter sometimes abbreviated as "I/O value") is preferably 0.2 or more and not more than 2.3, and more preferably 0.3 or more and not more than 2.0. By using such a solvent, it becomes possible to selectively extract the dicarboxylic acid and efficiently separate from impurities.

In addition, a solvent having a boiling point of 40° C. or higher at ordinary pressure (one atmosphere), and more preferably, a solvent having a boiling point of 60° C. or higher at ordinary pressure is used. In addition, a solvent having a boiling point of preferably not higher than 120° C., more preferably not higher than 100° C., and especially preferably not higher than 90° C. at ordinary pressure is useful.

By using the foregoing solvent, it becomes possible to avoid danger of ignition of the solvent upon evaporation, a problem of a decrease of extraction efficiency of the dicarboxylic acid to be caused due to evaporation of the solvent, and a problem that the solvent is hardly recycled. In addition, there is brought such an advantage that the amount of heat to be required at the time of separating the solvent after the use by means of distillation or the like, or reusing the solvent upon purification may be minimized.

The inorganicity and the organicity are proposed by *Organic Conception Diagram, "Systematic Organic Qualitative Analysis"*, FUJITA, Yuzuru, Kazamashobo Co., Ltd. (1974). The inorganicity/organicity ratio is obtained by calculating an organicity and an inorganicity on the basis of numerical values set in advance for functional groups constituting an organic compound and determining a ratio therebetween.

Examples of the solvent having an I/O value of 0.2 or more and not more than 2.3 and having a boiling point of 40° C. or higher at ordinary pressure include ketone based solvents such as methyl ethyl ketone, methyl isobutyl ketone, acetone, etc.; ether based solvents such as tetrahydrofuran, dioxane, etc.; ester based solvents such as ethyl acetate, etc.; nitrile based solvents such as acetonitrile, etc.; and alcohols having a carbon number of 3 or more, such as propanol, butanol, octanol, etc.

I/O values and boiling points of respective solvents are shown in the following table.

TABLE 1

I/O value of respective solvents

| | I | O | I/O | Boiling point |
|---|---|---|---|---|
| Tetrahydrofuran | 30 | 80 | 0.375 | 66.0 |
| Methyl ethyl ketone | 65 | 60 | 1.083 | 79.6 |
| Methyl isobutyl ketone | 65 | 120 | 0.542 | 94.2 |
| Acetone | 65 | 40 | 1.625 | 56.1 |
| Acetonitrile | 70 | 40 | 1.750 | 81.1 |
| Ethyl acetate | 85 | 80 | 1.063 | 77.2 |
| Propanol | 100 | 60 | 1.667 | 97.2 |
| Isobutanol | 100 | 70 | 1.429 | 108.0 |
| Octanol | 100 | 160 | 0.625 | 179.8 |
| Dioxane | 40 | 80 | 0.500 | 101.3 |

By the contact step, the dicarboxylic acid can be selectively extracted into the solvent, and sugars, amino acids, and inorganic salts, all of which are highly soluble in water, are distributed into the aqueous solution phase. As a matter of course, a by-product salt formed in a protonation step of the dicarboxylic acid salt is distributed into the aqueous solution phase and can be easily separated from the dicarboxylic acid.

For example, in the case where the by-product salt is ammonium sulfate, almost all thereof is recovered into the aqueous solution phase. At the same time, ammonium sulfate is subjected to treatments including concentration, crystallization, drying, and the like together with the amino acids and sugars recovered into the aqueous solution phase, and the amino acids and sugars can be recovered as ammonium sulfate containing organic contents. In view of the fact that the ammonium sulfate appropriately contains organic materials, it is useful as a fertilizer.

(Contact Operation)

In the contact operation, the operation for bringing the aqueous solution containing a dicarboxylic acid and the solvent capable of achieving phase separation from the aqueous solution into contact with each other may be carried out by a single-stage or multi-stage manner, and it is preferably carried out by a multi-stage manner.

In addition, the solvent may be allowed to flow either concurrently or countercurrently to the aqueous solution containing a dicarboxylic acid. The contact step may be carried out either continuously or batchwise. An especially preferred embodiment is an embodiment in which after mixing the aqueous solution containing a dicarboxylic acid and the solvent by a mixer settler, the mixture is subjected to liquid-liquid separation; an extract phase, an intermediate phase, and a raffinate phase are separated and recovered, respectively; the intermediate phase is subjected to solid-liquid separation; and the separated and recovered liquid is subjected to phase separation according to the need and then returned into a step after the phase separation step.

By the foregoing contact step of brining the solvent and the aqueous solution containing a dicarboxylic acid into contact with each other, the dicarboxylic acid is extracted into the solvent. Here, the solvent is added in an amount of preferably from 0.5 to 5 volume times, and more preferably from 1 to 3 volume times the volume of the aqueous solution containing a dicarboxylic acid at the temperature at the time of contact.

Though the temperature at the time of contact is not particularly limited so far as it is a temperature at which the dicarboxylic acid is extracted, it is preferably from 30 to 60° C. When the contact temperature is 30° C. or higher, problems such as an increase of the viscosity of the solvent, etc. are prevented; in view of the fact that a time required for settling of the formed solid content becomes long, floating of the solid content in the solvent phase is prevented; and incorporation of the solid content into the solvent phase is suppressed. On the other hand, when the contact temperature is not higher than 60° C., a decrease of the extraction rate of the dicarboxylic acid is prevented, and the efficiency is good.

A time at the time of contact is not particularly limited so far as it is a time at which the dicarboxylic acid is sufficiently extracted, and though the contact time varies depending upon the contact apparatus or contact condition, in general, it is preferably from one second to 5 hours. When the contact time is one second or longer, the extraction of the dicarboxylic acid into the solvent phase is sufficient. On the other hand, when the contact time is not longer than 5 hours, not only the matter that the apparatus becomes unnecessarily large is prevented, an aspect of which is efficient, but the progress of denaturation of proteins coexistent in the dicarboxylic acid with the solvent is prevented, thereby suppressing an increase of the solid content.

A pressure at the time of contact is not particularly limited so far as it is a pressure at which the dicarboxylic acid is sufficiently extracted. In the case where the contact is continuously carried out, it is in general operated at atmospheric pressure.

(Phase Separation Operation)

The phase separation operation in the phase separation step can be carried out by allowing the contents to stand in the tank for a certain period, or can be carried out by a centrifuge. The foregoing mixer-settler type extractor has a settler section for achieving phase separation by allowing the mixed liquid obtained by contact mixing to stand, and the phase separation can be achieved by allowing the liquid to stand in the settler section for a certain period. The phase separation step may be carried out either continuously or batchwise.

Though a temperature at the time of phase separation is not particularly limited so far as it is a temperature at which of each of the phases can be separated, it is preferably from 30 to 60° C., and it is preferable to conduct the treatment at a temperature of the same degree as that in the contact operation. When the phase separation temperature is 30° C. or higher, an increase of the liquid viscosity is prevented to make it easy to achieve the separation of the solid content; incorporation of the solid content into the solvent phase is prevented; and the amount of the solvent incorporating into the solid content can be suppressed. On the other hand, when the phase separation temperature is not higher than 60° C., back extraction of the dicarboxylic acid into the aqueous solution in the phase separation process can be prevented.

A time at the time of phase separation is not particularly limited so far as it is a time at which the phase separation of each of the phases is achieved, and though the phase separation time varies depending upon the contact apparatus, the contact condition, and the phase separation method, in general, it is preferably from one minute to 5 hours. When the phase separation time is one minute or longer, the phase separation becomes sufficient; incorporation of the aqueous solution or the solid content into the solvent phase is prevented; and inversely, incorporation of the solvent or the solid content into the aqueous solution phase can be suppressed. On the other hand, when the separation time is not longer than 5 hours, the matter that the apparatus becomes unnecessarily large is prevented, an aspect of which is efficient.

In addition, a pressure at the time of phase separation is not particularly limited so far as it is a pressure at which the dicarboxylic acid is sufficiently extracted. In the case where the phase separation is continuously carried out, it is in general operated at atmospheric pressure.

(Protonation Step)

At the time of recovering the dicarboxylic acid in the solvent in the extraction step, in the aqueous solution containing a dicarboxylic acid, in the case where the dicarboxylic acid is present as an aqueous solution of a salt, there may be the case where an amount of the dicarboxylic acid and/or the dicarboxylic acid salt to be extracted into the solvent capable of achieving phase separation from the aqueous solution containing a dicarboxylic acid is small, and therefore, it is preferable to add an acid to the aqueous solution to achieve protonation.

For example, at the time of obtaining a dicarboxylic acid from a raw material derived from biomass resources, in the case of obtaining it utilizing fermentation with a microorganism, there may be the case where a hydrogen ion concentration (pH) of the fermentation liquid is regulated for the purpose of allowing the fermentation to efficiently proceed. In the case of carrying out alkali neutralization, the dicarboxylic acid exists as an aqueous solution of a salt, and therefore, it is especially preferable to conduct protonation. For example, in the case of using ammonia as a neutralizing agent in the fermentation operation, since the dicarboxylic acid exists as an ammonium salt, it is preferable to conduct protonation with an acid.

A protonation step of adding an acid to the aqueous solution containing a dicarboxylic acid may be a step to be carried out at any stage so far as it is a step before the extraction step. Since the acid which is used in the protonation step is required to achieve salt exchange with the dicarboxylic acid salt, in general, it is preferable to use an acid stronger than the dicarboxylic acid, namely an acid having an acid dissociation constant pKa smaller than the dicarboxylic acid, usually an acid having a pKa of less than 4.

The acid to be used may be either an organic acid or an inorganic acid, and it may be either a monovalent acid or a polyvalent acid. However, an inorganic acid is preferable. In the case of using sulfuric acid in the protonation step, ammonium sulfate is formed as a by-product salt. In the present production method, the case where the inorganic salt is a by-product salt is preferable because an improvement in liquid-liquid separation properties can be expected due to a salting out effect by the by-product salt in the extraction step.

Though an amount of the acid to be added varies depending upon the intensity of the acid, in general, the acid is added in an amount of from about 0.1 to 5 equivalent times the amount relative to the cation constituting the dicarboxylic acid salt. In general, the addition of the acid is regulated by a pH. Though the pH varies depending upon the acid intensity pKa of the dicarboxylic acid, it is at least not more than the pKa. The regulation is preferably operated at a pH of less than 4. On the other hand, even when the acid is excessively added, the decrease of the pH becomes blunt step-by-step, the excessive salt does not achieve salt exchange with the dicarboxylic acid salt and exists within the system. The surplus acid is finally recovered as the raffinate phase in the subsequently extraction step, and a neutralization treatment or the like is again required for that treatment, and hence, such is inefficient. In consequence, the pH is preferably controlled to 1 or more.

[II. Extract Phase Concentration Step]

In general, since the dicarboxylic acid concentration in the extraction phase is thin, a concentration operation is required. Though a degree of concentration is not particularly limited, it is preferable that a solubility of the dicarboxylic acid in the final concentrated liquid is not more than a saturated solubility and is close to the saturated solubility as far as possible.

In addition, the solvent which is used for the extraction frequently forms a minimum azeotropic composition together with water, and the azeotropic composition is frequently a composition in which a ratio of the solvent is larger than that of water. In consequence, a large amount of the solvent is distilled off following the concentration operation, and the solvent concentration in the concentrated liquid often decreases as compared with that before the concentration.

In general, the dicarboxylic acid obtained from a raw material derived from biomass resources contains a large amount of impurities which are highly soluble in water, and hence, in the subsequent crystallization step, a purification effect in which the system where water exists is higher than the system where the solvent coexists can be expected. In addition, when the solvent remains until the subsequent step, its recovery becomes more difficult, and therefore, the solvent concentration after the concentration is not more than 1%.

In order that the solvent concentration of the final concentrated liquid may be not more than 1% and made close to the saturated solubility, it is preferable to add water before the concentration and/or in the process of the concentration operation.

[III. Crystallization Step]

In general, the crystallization step is a step of crystallizing the dicarboxylic acid in the solution containing an extract phase as a solid dicarboxylic acid while utilizing a difference in solubility of the dicarboxylic acid or the like. Any method may be adopted so far as it is a step of crystallizing the dicarboxylic acid as a solid from the solution containing an extract phase.

More specifically, examples thereof include a cooling crystallization method of achieving crystallization utilizing temperature dependency of the solubility by varying the solution temperature; a method of achieving crystallization by volatilizing the solvent from the solution by an operation such as heating, pressure reduction, etc. to increase the dicarboxylic acid concentration in the solution; a method composed of a combination thereof; and the like.

In addition, in the cooling crystallization, examples of a cooling method thereof include a method of achieving cooling by circulating the solution containing an extract phase into an external heat exchanger, etc.; a method of throwing a tube through which a coolant circulates into the solution containing an extract phase; and the like.

Above all, according to a method in which the solvent in the solution is volatilized by decompressing the inside of the apparatus, thereby achieving cooling by evaporation heat of the solvent, not only hindrance of heat transfer to be caused due to deposition of the dicarboxylic acid on a heat exchange interface can be prevented, but concentration of the dicarboxylic acid in the solution follows, and this method is also preferable from the standpoint of crystallization yield.

In addition, the crystallization operation may be either a batch operation or a continuous operation. However, the continuous operation is preferable for reasons such that a scatter in particle size of the resulting solid dicarboxylic acid can be minimized; the operation is efficient for the mass production; and the energy required for the crystallization can be minimized; and other reason. A crystallization apparatus is not required to be a special crystallization tank, and known mixing tanks can be used.

[IV. Solid-Liquid Separation Step]

A dicarboxylic acid slurry obtained by crystallization is subjected to a solid-liquid separation operation, thereby separating a dicarboxylic acid crystal and a mother liquid from each other. A separation method is not particularly limited, and examples thereof include filtration separation, settling separation, and the like. In addition, the operation may be either a batch manner or a continuous manner. For example, examples of a solid-liquid separator with good efficiency include a continuous centrifugal filter, a centrifugal settler such as decanter, etc., and the like.

In addition, a wet cake recovered by the solid-liquid separation operation depending upon a required purity of the dicarboxylic acid can be rinsed with cold water or the like.

[V. Crystallization Mother Liquid Recycling Step]

At least a part of the mother liquid and/or rinsed liquid obtained in the solid-liquid separation step can be recycled into the step before the crystallization step. Though the step to be recycled is not particularly limited, recycling can be made into the extraction step or the concentration step.

When recycling is made into the extraction step, though an extraction column becomes large, impurities which are liable to be distributed into the water phase (with a small distribution coefficient) can be selectively removed from the recycling system. On the other hand, when recycling is made into the concentration step, though an extraction column may be made small, all of non-volatile impurities are accumulated within the recycling system.

Though all of the mother liquid and the rinse liquid can be recycled, in view of the fact that when the operation is continued for a long period of time, the impurities are accumulated within the recycling system, it is preferable to purge at least a part thereof out the system. In general, the purged water is disposed after treating the organic material with an activated sludge or the like. However, since the purged water contains the dicarboxylic acid and has a low pH, it is effective as a deactivating agent of the used bacterial cell as recovered by the fermentation operation.

As to the recycling, a recycling amount and a recycling place can be determined depending upon the required specification of the dicarboxylic acid.

[Other Purification Steps]

There may be the case where the dicarboxylic acid obtained by the foregoing methods is required to be further applied to a purification treatment or a drying step. That is, in the purification from the fermentation liquid containing a dicarboxylic acid, in many cases, it is important to decrease the amounts of, in addition to the nitrogen element contained in the biomass resources, many impurities such as a nitrogen element and ammonia derived from fermentation microorganisms, sulfur-containing impurities, metal cations, etc. In addition, there may be the case where it is necessary to reduce the content of a coloring component or an odorous component contained in the dicarboxylic acid, or to reduce the amount of impurities displaying absorption in an ultraviolet ray region of from 250 to 300 nm to an extent that an average absorbance is not more than 0.05.

Examples of such a removal method of impurities include treatments such as a decoloration step with an adsorbing agent such as an activated carbon, etc., an ion exchange step of removing coexistent ions with an ion exchange resin, a hydrogen treatment step for the purpose of hydrogenation of an existent unsaturated dicarboxylic acid, a crystallization step of further achieving high-degree purification, etc.

In addition, examples of a removal method of an odorous component include a deodorization method with an adsorbing agent such as an activated carbon, etc., a cleansing removal method with an organic solvent, a crystallization method, an aeration method, and the like. As other means, a hydrogen treatment in the presence of a catalyst is effective.

Of these deodorization methods of a dicarboxylic acid, for example, in the case of containing succinic acid as the component derived from biomass resources, there may be the case where the dicarboxylic acid-containing liquid contains a small amount of fumaric acid. Therefore, when a hydrogen treatment is carried out, not only the odorous component in the dicarboxylic acid can be easily removed, but succinic acid is formed from fumaric acid, and an enhancement of the yield of succinic is simultaneously achieved. Thus, the hydrogen treatment method is an especially excellent technique.

In addition, in order to reduce the amount of impurities displaying absorption in an ultraviolet ray region of from 250 to 300 nm to an extent that the average absorbance is not more than 0.05, a technique in which an aliphatic dicarboxylic acid is subjected to a hydrogen treatment, and a purification treatment such as a crystallization treatment, an activated carbon treatment, etc. is further combined therewith and achieved is effective.

Embodiments of the respective steps are hereunder described in detail by reference to the case where the dicarboxylic acid is succinic acid. But, these descriptions are representative examples of the embodiments, and it should not be construed that the present invention is limited thereto.

The hydrogen treatment may be any reaction form of a batch system or a continuous system and can be carried out according to the conventionally known method. Specifically, examples of the hydrogen treatment include a method in which a solution containing succinic acid and a hydrogenation catalyst are allowed to coexist in a pressure reactor, this mixture is subjected to a hydrogen treatment by introducing a hydrogen gas thereinto while stirring, and a succinic acid-containing reaction liquid after the treatment is separated from the hydrogenation catalyst and discharged from the reactor; a method in which using a fixed bed multipipe type or single pipe reactor, a succinic acid-containing solution and a hydrogen gas are subjected to a hydrogen treatment while circulating them from a lower part of the reactor, and a succinic acid-containing reaction liquid after the treatment is discharged; a method in which a hydrogen gas is circulated from a lower part of a reactor, and a succinic acid-containing solution is circulated from an upper part thereof, thereby carrying out a hydrogen treatment, and a succinic acid-containing reaction liquid after the treatment is discharged; and the like.

As the hydrogenation catalyst, known homogenous or heterogeneous noble metal-containing hydrogenation catalysts can be used. Though the hydrogenation catalyst is not particularly limited, specific examples thereof include hydrogenation catalysts containing a noble metal such as ruthenium, rhodium, palladium, platinum, etc. Of these, hydrogenation catalysts containing palladium or platinum are preferable, and in particular, hydrogenation catalysts containing palladium are more preferable.

In such a hydrogenation catalyst, the foregoing noble metal-containing compound can be used as it is, or can be used while allowing a ligand such as organic phosphines, etc. to coexist. However, heterogeneous noble metal-containing catalysts are preferable from a reason of easiness of catalyst separation.

In addition, such a noble metal-containing compound is able to achieve the hydrogen treatment in the copresence of silica or titanium, a metal oxide such as zirconia, active alumina, etc., or a composite metal oxide thereof, or an activated carbon. This method is a preferred embodiment because not only the odorous component contained in succinic acid derived from biomass resources but the coloring component or organic impurities can be simultaneously adsorbed and removed, and the impurities can be efficiently removed.

The same effects can also be achieved at the time of using a catalyst obtained by supporting the foregoing noble metal on a carrier such as silica or titanium, a metal oxide, for example, zirconia, active alumina, etc., or a composite metal oxide thereof, or an activated carbon, and therefore, a method of using such a supported catalyst is also suitably adopted.

In general, a supporting amount of the noble metal is preferably from 0.1 to 10% by weight of the carrier. In addition, though the carrier is not particularly limited, for a reason that an elution amount of the metal during the hydrogen treatment is small, silica or an activated carbon is preferable, and an activated carbon is especially preferable.

In consequence, the embodiment in which the hydrogen treatment is carried out with a hydrogenation catalyst obtained by supporting the foregoing noble metal on a carrier such as silica or titanium, a metal oxide, for example, zirconia, active alumina, etc., or a composite metal oxide thereof, or an activated carbon is included in the definition of an embodiment in which the hydrogenation treatment is carried out with a hydrogenation catalyst in the presence of any one adsorbing agent selected from the group consisting of a metal oxide, silica, and an activated carbon.

Examples of the solvent into which the component derived from biomass resources is incorporated at the time of the hydrogen treatment include water; organic acids such as acetic acid, propionic acid, etc.; esters such as ethyl acetate, etc.; alcohols such as methanol, ethanol, propanol, isopropanol, butanol, 2-ethyl-1-hexanol, isobutanol, etc.; ethers such as diethyl ether, di-n-butyl ether, diisopropyl ether, di-n-butyl ether, tetrahydrofuran, dioxane, etc.; ketones such as acetone, methyl ethyl ketone, diethyl ketone, etc.; nitriles such as acetonitrile, etc.; mixed solvents thereof; and the like. Of these, water is the most preferable.

In general, the water is preferably deionized water, distilled water, river water, well water, tap water, or the like. The solution obtained by crystallizing succinic acid from the succinic acid-containing reaction liquid in a post step after the hydrogenation reaction, followed by filtration can also be repeatedly used according to the need. A succinic acid concentration in the solution may be not more than the saturated solubility at the liquid temperature.

In general, as to a content of fumaric acid that is an unsaturated dicarboxylic acid contained in succinic acid to be subjected to the hydrogen treatment, a lower limit thereof is preferably 0.01% by weight or more, and more preferably 0.05% by weight or more, and an upper limit thereof is preferably not more than 10% by weight, and more preferably not more than 5% by weight relative to the weight of succinic acid. When the content of fumaric acid is 0.01% by weight or more, the matter that the purification process until the hydrogen treatment step becomes complicated can be prevented. On the other hand, when the content of fumaric acid is not more than 10% by weight, the matter that it takes a long time for the hydrogen treatment can be prevented, and such a problem that a high-concentration succinic acid solution cannot be prepared while suppressing the deposition of fumaric acid having a low solubility can be prevented.

Though the hydrogen to be used may be pure hydrogen, hydrogen diluted with an inert gas such as nitrogen, helium, argon, etc. can also be used. In general, a concentration of carbon monoxide in the hydrogen gas is preferably not more than 10,000 ppm, more preferably not more than 2,000 ppm, and still more preferably not more than 1,000 ppm because the influence against the hydrogen treatment efficiency is a matter of concern.

As to a hydrogen pressure at the time of the hydrogen treatment, in general, a lower limit thereof is preferably 0.1 MPa or more, and in general, an upper limit thereof is preferably not more than 5 MPa, more preferably not more than 3 MPa, and still more preferably not more than 1 MPa. When the hydrogen pressure is 0.1 MPa or more, the reaction rate increases, so that the matter that it takes a time too much until completion of the reaction can be prevented. On the other hand, when the hydrogen pressure is not more than 5 MPa, it is possible to prevent the formation of, as a by-product, a hydride of succinic acid such as butanediol, tetrahydrofuran, etc. depending upon the catalyst or reaction condition.

As to a temperature at the time of the hydrogen treatment, in general, a lower limit thereof is preferably 30° C. or higher, and more preferably 50° C. or higher, and in general, an upper limit thereof is preferably not higher than 150° C., and more preferably not higher than 120° C. When the reaction temperature is 30° C. or higher, the reaction rate increases, so that the matter that it takes a time too much until completion of the reaction can be prevented. On the other hand, when the reaction temperature is not higher than 150° C., not only the formation of, as a by-product, a hydride of succinic acid can be prevented, but the matter that the amount of a by-product such as malic acid, etc. increases at the time of using water as the solvent can be prevented.

Examples of the crystallization solvent in the crystallization treatment include water; organic acids such as acetic acid, propionic acid, etc.; esters such as ethyl acetate, etc.; alcohols such as methanol, ethanol, propanol, isopropanol, butanol, 2-ethyl-1-hexanol, isobutanol, etc.; ethers such as diethyl ether, di-n-butyl ether, diisopropyl ether, di-n-butyl ether, tetrahydrofuran, dioxane, etc.; ketones such as acetone, methyl ethyl ketone, diethyl ketone, etc.; nitriles such as acetonitrile, etc.; mixed solvents thereof; and the like. Of these, water is the most preferable. In general, the water is preferably deionized water, distilled water, river water, well water, tap water, or the like.

A crystallization temperature can be chosen from the range of preferably from about 0 to 90° C., and more preferably from about 0 to 85° C. A cooling rate can be chosen within the range of preferably from about 1 to 120° C./hr, and more preferably from about 5 to 60° C./hr, and it is preferable to conduct the crystallization at ordinary pressure (for example, about 1 atm.), under reduced pressure, or under elevated pressure. In addition, an aging time can be suitably chosen within the range of preferably from about 0.1 to 5 hours, more preferably from about 0.5 to 4 hours, and still more preferably from about 0.5 to 2 hours.

By combining the foregoing crystallization treatment with an activated carbon treatment according to the need, the amount of impurities contained in succinic acid, which display absorption in an ultraviolet ray region of from 250 to 300 nm, may be reduced to an extent that an average absorbance is not more than 0.05.

As the activated carbon to be used, arbitrary known activated carbons including coal based, wood based, coconut shell based, or resin based activated carbons or the like are useful. In addition, activated carbons obtained by activating each of these various raw material activated carbons including coal based, wood based, coconut shell based, or resin based activated carbons or the like through a method such as a gas activation method, a steam activation method, a chemical activation method using zinc chloride, phosphoric acid, or the like, etc. are useful.

Specific examples thereof include Calgon CPG, Calgon CAL, Calgon SGL, Diasorb W, Diahope MS10, Diahope MO10, Diahope MS16, Diahope 6MD, Diahope 6MW, Diahope 8ED, Diahope ZGN4, and Centur, all of which are manufactured by Calgon Mitsubishi Chemical Corporation; GAC, GAC PLUS, GCN PLUS, C GRAN, RO, ROX, DARCO, CN, SX, SX PLUS, SA, SX, PK, and W, all of which are manufactured by Norit Japan Co., Ltd.; GW, GWH, GLC, 4GC, KW, PW, and PK, all of which are manufactured by Kuraray Chemical Co., Ltd.; HC-30S, GL-30S, 4G-3S, PA, and PC, all of which are manufactured by Tsurumi Coal Co., Ltd.; P, W, CW, SG, SGP, S, GB, CA, and K, all of which are manufactured by Futamura Chemical Co., Ltd.; Shirasagi KL, Shirasagi W2C, Shirasagi WH2C, Shirasagi W5C, Shirasagi WH5C, Shirasagi WH5X, Shirasagi XS7100H-3, Carboraffin, Shirasagi A, Shirasagi C, and Shirasagi M, all of which are manufactured by Japan EnviroChemicals, Ltd.; Hokuetsu CL-K, Hokuetsu HS, and Hokuetsu KS, all of which are manufactured by Ajinomoto Fine-Techno Co., Inc.; and the like.

Of these, a coconut shell based activated carbon and a wood based activated carbon are preferable for the reason that they are able to efficiently remove impurities contained in an aliphatic dicarboxylic acid, especially succinic acid, which display absorption in an ultraviolet ray region of from 250 to 300 nm.

On the other hand, from the viewpoint of efficiently removing a coloring component of an aliphatic dicarboxylic acid, especially succinic acid, an activated carbon activated by a gas activation method, a steam activation method, a chemical activation method using zinc chloride, phosphoric acid, etc., or other method is preferable. Of these, an activated carbon activated by a steam activation method or a chemical activation method using zinc chloride, phosphoric acid, etc. is preferable; and an activated carbon activated by a chemical activation method using zinc chloride, phosphoric acid, etc. is especially preferable.

As to the shape of the activated carbon to be used, any of a powered activated carbon, a crushed activated carbon, a molded activated carbon, or a fibrous activated carbon is useful. In the case where the activated carbon is used upon being packed in a column, a particulate or granular activated carbon is preferable in view of controlling a column pressure.

As a system for the activated carbon treatment, any of a method of mixing the activated carbon in a batch manner and then subjecting the mixture to filtration separation, or a method of allowing the liquid to flow into a packed layer of the activated carbon is adoptable. In general, a treatment time is preferably from 5 minutes to 5 hours, and more preferably from 10 minutes to 2 hours in the case of a batch manner, and in general, it is preferably from 0.1 to 20 $hr^{-1}$ in terms of SV (space velocity) in the case of a packed column system. In general, a treatment temperature is preferably from 20 to 90° C.

Furthermore, for the purpose of removing impurities in succinic acid, a purification operation such as an ion exchange column treatment, etc. may be adopted in combination. The ion exchange column treatment as referred to herein is to allow the liquid to be treated to flow into a column packed with an ion exchange resin, thereby removing an ion.

The ion exchange resin should be selected depending upon an ion contained in the liquid to be treated and the purity of succinic acid as required. For example, for the purpose of removing an anion such as a sulfate ion, a chlorine ion, etc., an anion exchange resin (OH type) can be used; and for the purpose of removing a cation such as a metal ion, an ammonium ion, etc., a cation exchange resin (H type) can be used. The both may be used according to the need.

The ion exchange resin is classified into a strongly acidic cation exchange resin, a weakly acidic cation exchange resin, a strongly basic anion exchange resin, and a weakly basic anion exchange resin depending upon the intensity of an acid or base of a functional group thereof. Furthermore, the ion exchange resin is classified into a gel type and a porous type depending upon the shape thereof, but the ion exchange resin to be used is not particularly limited. However, taking into consideration the efficiency of ion exchange, it is preferable to use a strongly acidic cation exchange resin with a higher intensity as the acid or a strongly basic anion exchange resin with a higher intensity as the base. In addition, there is no special reason that the shape is a porous type, and it is preferable to use a gel type which is generally useful and inexpensive. Specifically, there are exemplified Diaion SK1B (H type), etc. for the cation exchange resin and Diaion SA10A, etc. for the anion exchange resin, respectively.

The ion exchange column treatment can be carried out within the temperature range of a temperature at which succinic acid is dissolved in a liquid to be treated or higher and lower than a heat-resistant temperature of the ion exchange resin. That is, in the cation exchange resin, in general, the treatment is preferably carried out at from 20 to 100° C., the temperature of which, however, varies depending upon the concentration of succinic acid in a liquid to be treated. On the other hand, the anion exchange resin is lower in heat resistance than the cation exchange resin, and therefore, in general, the treatment is preferably carried out at from 10 to 80° C. From the viewpoint of the treatment temperature, in the case of using the anion exchange column treatment, a step in which the column treatment can be achieved in a low concentration of succinic acid at a low temperature is preferable.

In addition, though the method of allowing the liquid to flow is not particularly limited, in general, the treatment is preferably carried out at a space velocity (SV) of from 0.1 to 10 $hr^{-1}$ and at a superficial velocity of from 1 to 20 m/hr. When the treatment rate is not more than the upper limit, the matter that a pressure loss becomes large before and after the column is prevented, and the ion exchange becomes sufficient. In addition, when the treatment rate is the lower limit or more, the matter that the column becomes unnecessarily large can be prevented.

In general, in the column treatment, when the ion concentration is always or periodically measured in a column outlet, and leakage of the ion in the column outlet is found, the ion exchange resin is subjected to a regeneration treatment. The regeneration of the ion exchange resin can be carried out using an acid such as sulfuric acid, hydrochloric acid, etc. in the cation exchange resin or an alkali such as caustic soda, etc. in the anion exchange resin, respectively according to a usual method.

At the time of using the resulting dicarboxylic acid as a polymer raw material, there may be the case where it is necessary to reduce the amount of impurities displaying absorption in an ultraviolet ray region of from 250 to 300 nm such that an average absorbance is not more than 0.05. In that case, the average absorbance is preferably not more than 0.03, and especially preferably not more than 0.01. When an aliphatic dicarboxylic acid having a high average absorbance is used as a polymer raw material, there may be the case where coloration of the produced polymer becomes remarkable.

In the case where the aliphatic dicarboxylic acid is succinic acid, the absorbance in the present description is a value obtained by charging a 3.0 wt % succinic acid aqueous solution in a quartz cell having an optical path length of 1 cm and achieving the measurement by an ultraviolet-visible absorption spectrophotometer. In the present description, though the absorbance was measured using an ultraviolet-visible absorption spectrophotometer (Hitachi's spectrophotometer: UV-3500), it can also be measured using a commercially available ultraviolet-visible absorption spectrophotometer.

The absorbance (A) as referred to herein is an absorbance when measured at an optical path length 1 cm and is a value calculated according to the following definition.

$$A=\log_{10}(I_0/I)$$

(Here, $I_0$ represents an intensity of incident light; and I represents an intensity of transmitted light.)

In addition, the average absorbance in an ultraviolet ray region of from 250 to 300 nm is a value obtained by dividing the total sum of absorbances measured at intervals of 1 nm within the range of from 250 to 300 nm by 51.

Average absorbance=(Total sum of absorbances measured at intervals of 1 nm within the range of from 250 to 300 nm)/51

In the present description, though the foregoing impurities displaying absorption in an ultraviolet ray region of from 250 to 300 nm are not particularly limited, examples thereof include compounds having a nitrogen element and compounds displaying aromaticity. Examples of such compounds include oxygen-containing heterocyclic aromatic compounds such as furan, etc.; nitrogen-containing heterocyclic aromatic compounds such as pyrrole, pyridine, pyrazine, etc.; and benzene based aromatic compounds such as phenol, benzaldehyde, benzoic acid, etc.

Specific examples thereof include monohydroxybenzoic acids such as furfural, furfuryl alcohol, methylfurfuryl alcohol, hydroxymethylfurfural, furosine, 2-pyrrolecarboxyaldehyde, pyrrolecarboxylic acid, methylpyrrolecarboxylic acid, pyridinecarboxylic acid, pyridinedicarboxylic acid, methylpyridinecarboxylic acid, methylpyridinedicarboxylic acid, pyrazine, 2-methylpyrazine, dimethylpyrazine, trimethylpyrazine, tetramethylpyrazine, phenol, benzoic acid, salicylic acid, creosotic acid, etc.; dihydroxybenzoic acids such as pyrocatechuic acid, protocatechuic acid, etc.; trihydroxybenzoic acids such as gallic acid, etc.; aromatic aldehydes such as benzaldehyde, methyl benzaldehyde, dimethyl benzaldehyde, etc.; mixtures thereof; and the like. Incidentally, while there may be the case where the foregoing compounds include isomers, the foregoing examples of the compounds include all of isomers.

As described previously, the species of impurities to be removed vary depending upon the kind of the activated carbon, and therefore, examples of a method for removing such impurities include a method of combining plural species of activated carbon and a method of combining an activated carbon treatment with the foregoing hydrogen treatment or crystallization treatment. In addition, at the time of using water as the solvent, there may be the case where a water-insoluble component incorporates into the dicarboxylic acid solution derived from the fermentation. Such incorporation of an insoluble component causes a lowering in the efficiency of the foregoing removal of impurities by an activated carbon or the subsequent purification step, and therefore, it is preferable to remove the insoluble component in advance.

A method in which the removal of an insoluble component is carried out by subjecting the succinic acid solution derived from the fermentation to a known membrane permeation treatment in a step after deriving into succinic acid from a succinate formed by the fermentation method until the activated carbon treatment step is preferable. Also, as another method, a method in which permeability of the membrane permeation treatment is enhanced by adsorbing the insoluble component in the copresence of a powdered activated carbon, or a method in which the foregoing impurities are simultaneously adsorbed and removed together with the insoluble component using an appropriate powdered active carbon is also suitably adopted.

Furthermore, at the time of carrying out the removal of impurities by means of a combination of crystallization or/and an activated carbon treatment with a hydrogen treatment, though there are no particular limitations, a process of carrying out the crystallization or/and the activated carbon treatment step before the hydrogen treatment step is suitably adopted because the impurities are efficiently removed. This process is also suitably adopted in the removal of impurities from the succinic acid solution derived from biomass resources.

The succinic acid recovered by means of crystallization can be dried in the usual way depending upon its application. In general, the succinic acid is dried to such an extent that its water content is preferably from 0.1 to 2% by weight, and more preferably from 0.2 to 1% by weight.

The drying method is not particularly limited, and a direct heating system for directly heating it with warm air, an indirect heating system with a steam, or the like is adoptable depending upon the heating type. For example, a box type dryer, a band dryer, a rotary dryer, and the like are exemplified as the dryer with warm air; a drum dryer, a disc dryer, and the like are exemplified as the dryer by means of indirect heating.

In addition, the operation pressure may be ordinary pressure or reduced pressure. Furthermore, the operation system may be either a batch operation or a continuous operation. In general, the temperature of warm air is preferably from 20 to 200° C., and more preferably from 50 to 150° C. in terms of a temperature of the heating plane. When the temperature is 20° C. or higher, the matter that a highly reduced pressure is required for drying can be prevented. In addition, when the temperature is not more than 200° C., the matter that succinic acid is dehydrated to form succinic anhydride can be prevented.

In addition, the dicarboxylic acid can also be purified to the same extent by a method described below. A purification method of the case where the dicarboxylic acid is succinic acid is hereunder described as an example.

That is, a technique for carrying out a reactive crystallization step of not only forming succinic acid but depositing the formed succinic acid in the copresence of an alcohol by a multi-stage manner by reacting ammonium succinate as fermentation-produced with a microorganism or a solution thereof with a monocarboxylic acid is also effective. Though the monocarboxylic acid to be used is not particularly limited so far as it is a monocarboxylic acid capable of converting ammonium succinate into succinic acid, it is preferably acetic acid or propionic acid.

In addition, what the reactive crystallization step is carried out by a multi-stage manner means that after adding a monocarboxylic acid to the ammonium succinate reaction liquid to carry out first-stage reactive crystallization, an ammonium succinate intermediate deposited by the first-stage reactive crystallization, such as monoammonium succinate, etc., is separated; a monocarboxylic acid is newly added to the separated intermediate to carry out second-stage reactive crystallization; and the separation of an intermediate and the reactive crystallization with a monocarboxylic acid are repeated according to the need. Such multi-stage reactive crystallization is especially effective for the case where the amount of impurities is large, the case where succinic acid in the mother liquid is recovered by means of recrystallization, or the like.

The term "multi-stage" means two or more stages, and preferably from two to four stages. However, what number of stages should the reactive crystallization be carried out in total can be arbitrarily set according to the reaction scale, the required purity, or the like. As to the matter that at what number of final stage is obtainable free succinic acid by carrying out the reactive crystallization, it is preferable to set a total number of stages in advance by carrying out a preliminary experiment, or the like.

As the specific crystallization apparatus which is used for the reactive crystallization step, in addition to a mixing tank, generally used crystallization tanks can be used. The apparatus is unconcerned about its shape or technique so far as a crystal can be obtained by a solid-liquid equilibrium phenomenon. Examples thereof include a Krystal-Oslo crystallizer, a draft tube bulb crystallizer, a mixing tank crystallizer, a Swenson crystallizer, and the like.

The reactive crystallization condition is different between the final stage and other stage (preceding stage). First of all, the condition of the preceding stage is described. That is, in the preceding stage, since it is intended to convert diammonium succinate into monoammonium succinate as far as possible, it is preferable that the amount of the monocarboxylic acid to be added is equal to or more than the mole of ammonium succinate. However, when the amount of the monocarboxylic acid to be added is excessively large, the recovery rate is lowered due to a solvent effect of the monocarboxylic acid, and therefore, it is preferably not more than 5 molar times. Incidentally, an optimum value increases or decreases depending upon the amount of coexisting ammonia or water.

In the case of using acetic acid, an upper limit of the acetic acid amount is dominated by the solubility, and this is conspicuously dependent upon the temperature. Furthermore, in a region having a high pH, the viscosity is high, and it takes a long time for the filtration, and therefore, a weight ratio of ammonia and acetic acid is much more preferably 14 or more. On the other hand, when a large amount of acetic acid is used, energy is required for recovery, and therefore, the weight ratio of ammonia and acetic acid is preferably not more than 100, and much more preferably not more than 30. In the case where propionic acid is used, a lower limit of the pH is larger than that of acetic acid. Since an upper limit of the pH is determined by an equilibrium relation with the salt exchange reaction and solubility, it is equal to that in acetic acid. In consequence, a narrower range than that in acetic acid is the condition.

Though the condition of the temperature or pressure in the preceding stage is not particularly limited, there may be the case where it is restricted by the kind and amount of the alcohol or monocarboxylic acid to be used, or the crystallization apparatus. For example, in the case where a large amount of methanol is used, methanol vaporizes in vacuo and is not aggregated, thereby making the recovery difficult. Thus, it is preferable that the system is not made in vacuo.

In addition, even when a little pressure is kept, there may be the case where a refrigerator is necessary. Thus, though the condition varies depending upon the crystallization apparatus to be used, for example, the temperature is preferably from 0° C. to 50° C., and the pressure is preferably not more than ordinary pressure and 5 kPa or more.

Though the foregoing reactive crystallization is carried out in the copresence of an alcohol, the alcohol to be made coexistent is preferably a monohydric alcohol. In addition, an alcohol having a carbon number of from 1 to 3 is preferable. In particular, methanol, ethanol, 1-propanol, and 2-propanol are preferable.

The alcohol is added in the preceding stage, and its addition amount is preferably 5% by weight or more and not more than 40% by weight relative to the total weight of the ammonium succinate reaction liquid and the monocarboxylic acid. When the alcohol is coexistent, the viscosity of a mixture of ammonium succinate and acetic acid decreases, and therefore, the efficiency of the reactive crystallization increases. In addition, in the case where the ammonium succinate solution is mixed with a sugar, there is brought an effect for separating the sugar as in the case of fermentation producing the ammonium succinate solution with a microorganism.

In the light of the above, in the preceding stage, after the alcohol is added to carry out the reactive crystallization, ammonium succinate is recovered, and in the final stage, a monocarboxylic acid is added while regulating the alcohol concentration of the reaction system within the range of from 0.1 ppm to 10%, thereby carrying out the reactive crystallization. In the final stage, it is preferable to carry out the reactive crystallization without adding an alcohol.

In addition, even in the case where an alcohol is not added, since a considerable amount of the alcohol is present in a slurry containing ammonium succinate which comes out from the crystallization tank just before the final stage, for the purpose of regulating the alcohol concentration in the reactive crystallization tank of the final stage within the range of from 0.1 ppm to 10%, it is preferable to remove the alcohol in the slurry by means of filtration, drying, washing, etc. of this slurry.

In addition, the system of the reaction system may contain water. However, in this case, it is also preferable to regulate the water concentration in the final-stage reactive crystallization tank to not more than 10%. In consequence, it is preferable to simultaneously remove the alcohol and water in the slurry by means of filtration, drying, washing, etc. of the ammonium succinate-containing slurry as obtained in the crystallization tank in the stage just before the final stage.

As a method for removing the alcohol and water from the ammonium succinate-containing slurry as obtained by the preceding stage, for example, the slurry from the crystallization tank of the preceding stage is subjected to a combination of separation of the mother liquid by usual filtration or centrifugation (centrifugal decantation) or the like, washing or rinsing with acetic acid or a filtrate (mother liquid) in the final stage, drying or distillation of the solution, and the like, whereby water or the alcohol can be separated. In addition, the alcohol or water may be removed through a treatment such as centrifugal filtration, filter pressing, etc.

By obtaining a crystal or concentrated liquid containing succinic acid from the slurry obtained in the preceding stage and further carrying out final-stage crystallization with acetic acid by an arbitrary method, succinic acid is obtained. As to a final-stage crystallization condition, it is preferable that the amount of the alcohol is in the range of from 1 ppm to 10%, and the amount of water is in the range of from 1 ppm to 10%; and it is much more preferable that the amount of each of water and the alcohol is not more than 5%. At that time, the pH obtained from succinic acid is in general from about 2.1 (dissolved state) to about 4.5 (filtrate). This is corresponding to the weight ratio of ammonia and acetic acid of 13.4 or more.

Furthermore, when the weight ratio of ammonia and acetic acid is 1/14 or more, the matter that it takes a long time for the filtration can be prevented, and therefore, the weight ratio of ammonia and acetic acid is much more preferably 1/14 or more. On the other hand, by using a large amount of acetic acid, the matter that energy is required for the recovery is prevented, and therefore, the weight ratio of ammonia and acetic acid is preferably not more than 1/100, much more preferably not more than 1/50, and especially preferably not more than 1/30.

The lower the temperature, the higher the recovery rate is. In a region where the pH is close to 2.1, the melting point of acetic acid that is 16° C. is a lower limit value thereof; whereas an upper limit thereof is dominated by the solubility, and in general, it is preferably not higher than 40° C., and more preferably 20° C. or higher and not higher than 35° C. In a region where the pH is close to 4.5, since there is depression of freezing point of acetic acid, the temperature is preferably 10° C. or higher; whereas an upper limit thereof is dominated by the solubility, and in general, it is preferably not higher than 60° C., and more preferably 15° C. or higher and not higher than 40° C.

Incidentally, the amount of acetic acid which is added in the final-stage crystallization is preferably from about 0.8 times to 3.5 times in terms of a weight ratio relative to the crystal as obtained in the preceding stage.

As to this final-stage reactive crystallization, there are no particular restrictions regarding the apparatus. However, usual crystallization apparatuses, for example, a Krystal-Oslo crystallizer, a draft tube bulb crystallizer, a mixing tank crystallizer, a Swenson crystallizer, and the like, can be used. By subjecting the resulting slurry to solid-liquid separation adopting a general method such as filtration, centrifugation, etc., succinic acid can be obtained. When the crystal is washed with cold water and acetic acid, succinic acid with a higher purity can be obtained.

Succinic acid deposited in the final stage is collected by means of separation in the usual way. As the separation method, for example, a usual filtration operation, pressure filtration or filtration under reduced pressure with a Nutsche type filter, centrifugation, and the like can be adopted. Incidentally, as described above, the mother liquid after collecting succinic acid in the final stage can be reused for washing the slurry obtained in the preceding stage. Furthermore, a deionization treatment with a cation exchange resin or the like may be carried out according to the need. The thus obtained crystal of succinic acid can be further subjected to heat drying or drying under reduced pressure according to the need.

The dicarboxylic acid derived from biomass resources contains, as an impurity, a nitrogen atom derived from biomass resources and caused due to a fermentation treatment and a purification treatment including a neutralization step with an acid.

Specifically, a nitrogen atom derived from an amino acid, a protein, an ammonium salt, urea, a microorganism, and the like is contained. In general, for the purpose of obtaining a practically useful polymer, it is important to control the amount of the organic acid having a pKa value at 25° C. of not more than 3.7, the nitrogen compound, or the metal cation contained in the dicarboxylic acid by the foregoing purification method.

As to the organic acid having a pKa value at 25° C. of not more than 3.7, which is contained in the dicarboxylic acid derived from biomass resources by the foregoing method, a lower limit value thereof is in general more than 0 ppm, preferably 0.001 ppm or more, more preferably 0.01 ppm or more, still more preferably 0.05 ppm or more, especially preferably 0.07 ppm or more, and most preferably 0.1 ppm or more relative to the dicarboxylic acid. An upper limit thereof is in general not more than 1,000 ppm, preferably not more than 800 ppm, and more preferably not more than 600 ppm.

When the amount of the organic acid having a pKa value at 25° C. of not more than 3.7, which is contained in the dicarboxylic acid is more than 1,000 ppm, the viscosity of the polyester polyol as a polyurethane raw material becomes high; the handling operability is deteriorated; and a polyurethane having an abnormally high molecule weight, an abnormally large molecular weight distribution, or poor mechanical characteristics such as flexibility, elasticity, etc. due to gelation or the like at the time of polyurethane reaction tends to be formed. In addition, when the amount is too large, a scatter of the content is liable to be caused, and not only physical properties of the resulting polyurethane are variable, but even in the production step, the stable operation tends to become difficult.

In addition, when the amount of the organic acid having a pKa value is more than 0 ppm, the matter that the purification step of the dicarboxylic acid becomes complicated is prevented, an aspect of which is thus economically advantageous. Furthermore, when formed into a polyurethane, the mechanical strength tends to be enhanced.

Incidentally, by combining the foregoing fermentation condition with the purification condition such as extraction, crystallization, etc., it becomes possible to control the content of the organic acid having a pKa value at 25° C. of not more than 3.7. In addition, the content of the organic acid may be regulated by adding an organic acid to the dicarboxylic acid having a small amount of an organic acid. In addition, by undergoing a step for controlling the content of the organic acid to a preferred range, the content of a nitrogen atom or the content of a sulfur atom contained in the dicarboxylic acid derived from biomass resources can also be controlled, and in general, a dicarboxylic acid suitable for obtaining a practically useful polymer can be obtained.

As to a content of the nitrogen atom contained in the dicarboxylic acid derived from biomass resources by the foregoing method, in general, an upper limit thereof is preferably not more than 2,000 ppm, more preferably not more than 1,000 ppm, still more preferably not more than 100 ppm, and most preferably not more than 50 ppm in the dicarboxylic acid in terms of a mass ratio relative to the dicarboxylic acid. In general, a lower limit thereof is 0.01 ppm or more, and more preferably 0.05 ppm or more. For an economical reason of the purification step, the lower limit is still more preferably 0.1 ppm or more, yet still more preferably 1 ppm or more, and especially preferably 10 ppm or more.

When the content of the nitrogen atom contained in the dicarboxylic acid is not more than the foregoing upper limit, retardation of the polymerization reaction, an increase of the quantity of terminal carboxyl groups of the polyester polyol, coloration, partial gelation, a lowering of the stability, and the like can be prevented. On the other hand, when the content of the nitrogen atom contained in the dicarboxylic acid is the foregoing lower limit or more, the matter that the purification step becomes complicated is prevented, an aspect of which is thus economically advantageous.

The content of the nitrogen atom is a value measured by a known method such as an elemental analysis method, etc., or a method in which an amino acid or ammonia in a sample is separated under a biological amino acid separation condition using an amino acid analyzer and subjected to ninhydrin coloration, followed by detection.

The use of a dicarboxylic acid having a nitrogen atom content falling within the foregoing range is advantageous for reducing the coloration of the resulting polyurethane and polyester polyol. In addition, there is also brought an effect for delaying the polymerization reaction of the polyurethane and polyester polyol.

In addition, in the case of using a dicarboxylic produced by the fermentation method, there may be the case where a large amount of a sulfur atom is contained by the purification treatment including a neutralization step with an acid. Specifically, examples of impurities containing a sulfur atom include sulfuric acid, a sulfate, sulfurous acid, an organic sulfonic acid, an organic sulfonate, and the like.

As to a content of the sulfur atom contained in the dicarboxylic acid, in general, an upper limit thereof is preferably not more than 100 ppm, more preferably not more than 20 ppm, still more preferably not more than 10 ppm, especially preferably not more than 5 ppm, and most preferably not more than 0.5 ppm in the dicarboxylic acid in terms of a mass ratio relative to the dicarboxylic acid. On the other hand, in general, a lower limit thereof is 0.001 ppm or more, more preferably 0.01 ppm or more, still more preferably 0.05 ppm or more, and especially preferably 0.1 ppm or more.

When the content of the sulfur atom contained in the dicarboxylic acid is not more than the foregoing upper limit, delay of the polymerization reaction, partial gelation of the polyester polyol, an increase of the quantity of carboxyl terminal, a lowering of the stability, and the like can be prevented. On the other hand, when the content of the sulfur atom contained in the dicarboxylic acid is the foregoing lower limit or more, the matter that the purification step becomes complicated is prevented, an aspect of which is thus economically advantageous. The content of the sulfur atom is a value measured by a known elemental analysis method.

In the present invention, in using the dicarboxylic acid derived from biomass resources as obtained by the foregoing method as a polyurethane raw material, a concentration of oxygen within a tank storing the dicarboxylic acid, which is connected to the polymerization system, may be controlled to not more than a fixed value. According to this, coloration due to an oxidation reaction of a nitrogen source that is an impurity of the polyurethane can be prevented.

For the purposes of controlling the oxygen concentration and storing the raw material, a tank is in general used. But, an apparatus other than the tank is also useful without particular limitations so far as it is able to control the oxygen concentration.

The kind of the storage tank is not specifically limited, and known metal-made storage tanks or those in which a lining of glass, a resin, or the like is applied to an inner surface thereof, glass-made or resin-made containers, and the like are useful. From the standpoint of strength or the like, metal-made tanks or those in which a lining is applied are preferably used.

As a material of the metal-made tank, known materials are used. Specifically, examples thereof include carbon steels, ferrite based stainless steels, martensite based stainless steels such as SUS410, etc., austenite based stainless steels such as SUS310, SUS304, SUS316, etc., clad steels, cast iron, copper, copper alloys, aluminum, Inconel, Hastelloy, titanium, and the like.

As to an oxygen concentration within the storage tank of the dicarboxylic acid, though a lower limit thereof is not particularly limited, in general, it is preferably 0.00001% or more, and more preferably 0.01% or more relative to the total volume of the storage tank. On the other hand, an upper limit thereof is preferably not more than 16%, more preferably not more than 14%, and still more preferably not more than 12%.

When the oxygen concentration within the storage tank of the dicarboxylic acid is the foregoing lower limit or more, the matter that the equipment or control step becomes complicated is prevented, an aspect of which is thus economically advantageous. On the other hand, when the oxygen concentration within the storage tank of the dicarboxylic acid is not more than the foregoing upper limit, coloration of the produced polyurethane can be suppressed.

As to a temperature within the storage tank of the dicarboxylic acid, in general, a lower limit thereof is preferably −50° C. or higher, and more preferably 0° C. or higher. On the other hand, in general, an upper limit thereof is preferably not higher than 200° C., more preferably not higher than 100° C., and still more preferably not higher than 50° C. For the reason that the temperature control is not necessary, a method of storage at room temperature is the most preferable. When the temperature is −50° C. or higher, an increase of the storage costs can be prevented. In addition, when the temperature is not higher than 200° C., concurrence of a dehydration reaction of the carboxylic acid or the like can be prevented.

As to a humidity within the storage tank of the dicarboxylic acid, in general, a lower limit thereof is preferably 0.0001% or more, more preferably 0.001% or more, still more preferably 0.01% or more, and most preferably 0.1% or more; and an upper limit thereof is preferably not more than 80%, more preferably not more than 60%, and still more preferably not more than 40%, relative to the total volume of the storage tank.

When the humidity within the storage tank of the dicarboxylic acid is 0.0001% or more, the matter that the control step becomes complicated is prevented, an aspect of which is thus economically advantageous. In addition, when the humidity within the storage tank of the dicarboxylic acid is not more than 80%, attachment of the dicarboxylic acid onto the storage tank or piping and blocking of the dicarboxylic acid can be prevented, and in the case where the storage tank is made of a metal, corrosion of the tank or the like can be prevented.

In general, a pressure within the storage tank of the dicarboxylic acid is preferably atmospheric pressure (ordinary pressure).

In general, the dicarboxylic acid which is used in the present invention is preferably one with less coloration. As to the yellow index (YI value) of the dicarboxylic acid which is used in the present invention, in general, an upper limit thereof is preferably not more than 50, more preferably not more than 20, still more preferably not more than 10, yet still more preferably not more than 6, and especially preferably not more than 4. On the other hand, though a lower limit thereof is not particularly limited, in general, it is preferably −20 or more, more preferably −10 or more, still more preferably −5 or more, especially preferably −3 or more, and most preferably −1 or more.

When a dicarboxylic acid having a YI value of not more than 50 is used, coloration of the produced polyurethane can be suppressed. On the other hand, when a dicarboxylic acid having a YI value of −20 or more is used, it is economically advantageous because not only extremely expensive investment in plant and equipment is not required for the production, but a long production time is not required. In the present description, the YI value is a value measured by a method on the basis of JIS-K7105.

(2) Aliphatic Diol:

The aliphatic diol which is used in the present invention is not particularly limited so far as it is an aliphatic or alicyclic compound having two OH groups, and examples thereof include aliphatic diols in which a lower limit value of the carbon atom number is preferably 2 or more, and an upper limit value thereof is preferably not more than 10, and more preferably not more than 6.

In addition, the diol unit as referred to herein is one derived from an aromatic diol and/or an aliphatic diol, and known compounds can be used. Of these, the use of an aliphatic diol is preferable.

Specific examples of the aliphatic diol include ethylene glycol, 1,3-propanediol, 2-methyl-1,3-propanediol, neopentyl glycol, 1,5-pentanediol, 3-methyl-1,5-pentanediol, 1,2-butanediol, 1,6-hexanediol, decamethylene glycol, 1,9-nonanediol, 1,4-butanediol, 1,4-cyclohexanedimethanol, and the like. These may be used solely or in admixture of two or more kinds thereof.

Of these, ethylene glycol, 1,4-butanediol, 1,3-propanediol, 2-methyl-1,3-propanediol and 3-methyl-1,5-pentanediol are preferable. Above all, ethylene glycol, 1,4-butanediol, and a mixture thereof are preferable; and one containing, as a main component, 1,4-butanediol or 1,4-butanediol is especially preferable.

It is meant by the terms "main component" as referred to herein that in general, the subject component accounts for preferably 50% by mole or more, more preferably 60% by mole or more, still more preferably 70% by mole or more, and especially preferably 90% by mole or more relative to the whole of diol units. These diols may be used solely, or may be used in admixture of two or more kinds thereof.

The diol having a branched structure is especially preferably 2-methyl-1,3-propanediol or 3-methyl-1,5-pentanediol.

When a diol having a methylene group between the hydroxyl groups and having an even carbon number is used, the mechanical strength of the resulting polyurethane increases, and when a diol having an odd carbon number or a branched structure is used, the handling properties of the polyester polyol are enhanced.

In addition to the above, examples of a diol other than the aliphatic diol, which may be mixed, include aromatic diols. Though the aromatic diol is not particularly limited so far as it is an aromatic compound having two OH groups, examples thereof include aromatic diols in which a lower limit value of the carbon number is preferably 6 or more, whereas in general, an upper limit value thereof is preferably not more than 15.

Specific examples of the aromatic diol include hydroquinone, 1,5-dihydroxynaphthalene, 4,4'-dihydroxydiphenyl, bis(p-hydroxyphenyl)methane, bis(p-hydroxyphenyl)-2,2-propane, and the like. In the present invention, in general, the content of the aromatic diol in the total amount of the diols is preferably not more than 30% by mole, more preferably not more than 20% by mole, and still more preferably not more than 10% by mole.

In addition, a polyether, both ends of which are terminated with a hydroxyl group, may be used in combination with the foregoing aliphatic diol, or may be used solely. As to the polyether, both ends of which are terminated with a hydroxyl group, in general, a lower limit value of the carbon number is preferably 4 or more, and more preferably 10 or more, and in general, an upper limit value thereof is preferably not more than 1,000, more preferably not more than 200, and still more preferably not more than 100.

Specific examples of the polyether, both ends of which are terminated with a hydroxyl group, include diethylene glycol, triethylene glycol, polyethylene glycol, polypropylene glycol, polytetramethylene glycol, poly-1,3-propanediol, poly-1,6-hexamethylene glycol, and the like. In addition, a copolymer polyether between polyethylene glycol and polypropylene glycol and the like can also be used.

In general, the use amount of such a polyether, both ends of which are terminated with a hydroxyl group, is a calculated amount of preferably not more than 90% by weight, more preferably not more than 50% by weight, and still more preferably not more than 30% by weight as the content in the polyester.

In the present invention, diols derived from biomass resources may be used as such a diol. Specifically, the diol compound may be produced directly from carbon sources such as glucose, etc. by the fermentation method, or a dicarboxylic acid, a dicarboxylic anhydride, or a cyclic ether, as obtained by the fermentation method, may be converted into a diol compound by a chemical reaction.

For example, 1,4-butanediol may be produced by means of chemical synthesis of succinic acid, succinic anhydride, a succinic acid ester, maleic acid, maleic anhydride, a maleic acid ester, tetrahydrofuran, γ-butyrolactone, or the like, as obtained by the fermentation method, or 1,4-butanediol may be produced from 1,3-butadiene obtained by the fermentation process. Of these, a method of obtaining 1,4-butanediol by means of hydrogenation of succinic acid in the presence of a reduction catalyst is efficient and preferable.

Examples of the catalyst to be used for hydrogenating succinic acid include Pd, Ru, Re, Rh, Ni, Cu, and Co, and compounds thereof. More specifically, examples thereof include Pd/Ag/Re, Ru/Ni/Co/ZnO, Cu/Zn oxide, Cu/Zn/Cr oxide, Ru/Re, Re/C, Ru/Sn, Ru/Pt/Sn, Pt/Re/alkali, Pt/Re, Pd/Co/Re, Cu/Si, Cu/Cr/Mn, ReO/CuO/ZnO, CuO/CrO, Pd/Re, Ni/Co, Pd/CuO/CrO$_3$, Ru phosphate, Ni/Co, Co/Ru/Mn, Cu/Pd/KOH, and Cu/Cr/Zn. Of these, Ru/Sn or Ru/Pt/Sn is preferable from the standpoint of catalytic activity.

Furthermore, a method of producing a diol compound from biomass resources through a combination of known organic chemical catalytic reactions is also positively adopted. For example, in the case of utilizing pentose as a biomass resource, a diol such as butanediol, etc. can be easily produced through a combination of known dehydration reaction and catalytic reaction.

There may be the case where the diol derived from biomass resources contains a nitrogen atom as an impurity derived from biomass resources or caused due to a fermentation treatment or a purification treatment including a neutralization step with an acid. In that case, specifically, a nitrogen atom derived from an amino acid, a protein, ammonia, urea, or a fermentation microorganism is contained.

As to a content of a nitrogen atom contained in the diol produced by the fermentation method, in general, an upper limit thereof is preferably not more than 2,000 ppm, more preferably not more than 1,000 ppm, still more preferably not more than 100 ppm, and most preferably not more than 50 ppm in terms of a mass ratio relative to the diol. Though a lower limit thereof is not particularly limited, in general, it is preferably 0.01 ppm or more, and more preferably 0.05 ppm or more. For the reason of economy of the purification step, the lower limit is still more preferably 0.1 ppm or more, yet still more preferably 1 ppm or more, and especially preferably 10 ppm or more.

When the content of the nitrogen atom contained in the diol produced by the fermentation method is not more than the foregoing upper limit, retardation of the polymerization reaction, an increase of the quantity of terminal carboxyl groups of the polyester polyol, coloration, partial gelation, a lowering of the stability, and the like can be prevented. On the other hand, when the content of the nitrogen atom contained in the dicarboxylic acid is the foregoing lower limit or more, the matter that the purification step becomes complicated is prevented, an aspect of which is thus economically advantageous.

In addition, in another embodiment, as to a content of a nitrogen atom contained in the dicarboxylic acid raw material and diol, in general, an upper limit thereof is preferably not more than 2,000 ppm, more preferably not more than 1,000 ppm, still more preferably not more than 100 ppm, and most preferably not more than 50 ppm in terms of a mass ratio relative to a total sum of the foregoing raw materials. Though a lower limit thereof is not particularly limited, in general, a lower limit thereof is preferably 0.01 ppm or more, more preferably 0.05 ppm or more, and still more preferably 0.1 ppm or more.

In the case of using the diol produced by the fermentation method, there may be the case where a sulfur atom is contained by the purification treatment including a neutralization step with an acid. In that case, specifically, examples of impurities containing a sulfur atom include sulfuric acid, sulfurous acid, an organic sulfonate, and the like.

As to a content of the sulfur atom contained in the diol, in general, an upper limit thereof is preferably not more than 100 ppm, more preferably not more than 20 ppm, still more preferably not more than 10 ppm, especially preferably not more than 5 ppm, and most preferably not more than 0.5 ppm in the diol in terms of a mass ratio relative to the diol. On the other hand, though a lower limit thereof is not particularly limited, in general, it is 0.001 ppm or more, more preferably 0.01 ppm or more, still more preferably 0.05 ppm or more, and especially preferably 0.1 ppm or more.

When the content of the sulfur atom contained in the diol is not more than the foregoing upper limit, retardation of the polymerization reaction, an increase of the quantity of terminal carboxyl groups of the polyester polyol, coloration, partial gelation, a lowering of the stability, and the like can be prevented. On the other hand, when the content of the nitrogen atom contained in the diol is the foregoing lower limit or more, the matter that the purification step becomes complicated is prevented, an aspect of which is thus economically advantageous. The content of the sulfur atom is a value measured by a known elemental analysis method.

In addition, in another embodiment, as to a content of a sulfur atom contained in the dicarboxylic acid raw material and diol, in general, an upper limit thereof is preferably not more than 100 ppm, more preferably not more than 20 ppm, still more preferably not more than 10 ppm, specially preferably not more than 5 ppm, and most preferably not more than 0.5 ppm as reduced into an atom in terms of a mass ratio relative to a total sum of the foregoing raw materials. Though a lower limit thereof is not particularly limited, in general, a lower limit thereof is preferably 0.001 ppm or more, more preferably 0.01 ppm or more, still more preferably 0.05 ppm or more, and especially preferably 0.1 ppm or more.

In the present invention, in using the diol derived from biomass resources as obtained by the foregoing method as a polyurethane raw material, for the purpose of suppressing coloration of the polyurethane to be caused due to the foregoing impurities, a concentration of oxygen or a temperature within a tank storing the diol, which is connected to the polymerization system, may be controlled.

This control makes it possible to suppress the coloration of the impurities themselves or the oxidation reaction of the diol accelerated by the impurities. For example, in the case of using 1,4-butanediol, coloration of a polyurethane due to an oxidation product of the diol such as 2-(4-hydroxybutyloxy) tetrahydrofuran, etc. can be prevented.

For the purposes of controlling the oxygen concentration and storing the raw material, a tank is in general used. But, an apparatus other than the tank is also useful without particular limitations so far as it is able to control the oxygen concentration. The kind of the storage tank is not specifically limited, and known metal-made storage tanks or those in which a lining of glass, a resin, or the like is applied to an inner surface thereof, glass-made or resin-made containers, and the like are useful. From the standpoint of strength or the like, metal-made tanks or those in which a lining is applied are preferably used.

As a material of the metal-made tank, known materials are used. Specifically, examples thereof include carbon steels, ferrite based stainless steels, martensite based stainless steels such as SUS410, etc., austenite based stainless steels such as SUS310, SUS304, SUS316, etc., clad steels, cast iron, copper, copper alloys, aluminum, Inconel, Hastelloy, titanium, and the like.

As to an oxygen concentration within the storage tank of the diol, though a lower limit thereof is not particularly limited, in general, it is preferably 0.00001% or more, more preferably 0.0001% or more, still more preferably 0.001% or more, and most preferably 0.01% or more relative to the total volume of the storage tank. In general, an upper limit thereof is preferably not more than 10%, more preferably not more than 5%, still more preferably not more than 1%, and most preferably not more than 0.1%.

When the oxygen concentration within the storage tank of the diol is 0.00001% or more, the matter that the control step becomes complicated is prevented, an aspect of which is thus economically advantageous. In addition, when the oxygen concentration is not more than 10%, an increase of coloration of the polymer by an oxidation reaction product of the diol can be prevented.

As to a storage temperature within the storage tank of the diol, in general, a lower limit thereof is preferably 15° C. or higher, more preferably 30° C. or higher, still more preferably 50° C. or higher, and most preferably 100° C. or higher; and an upper limit thereof is preferably not higher than 230° C., more preferably not higher than 200° C., still more preferably not higher than 180° C., and most preferably not higher than 160° C.

When the storage temperature within the storage tank of the diol is 15° C. or higher, the matter that the it takes a long time for raising the temperature at the time of producing a polyester is prevented, an aspect of which is thus economically advantageous for the production of a polyester, and the matter that the diol is solidified depending upon the kind thereof is prevented. On the other hand, when the storage temperature within the storage tank of the diol is not higher than 230° C., not only the matter that high-pressure storage equipment becomes necessary is prevented by suppressing evaporation of the diol, an aspect of which is thus economically advantageous, but deterioration of the diol can be prevented.

In general, a pressure within the storage tank of the diol is preferably a slightly elevated pressure by dry nitrogen or dry air. In the case where the pressure is too low or too high, the control equipment becomes complicated, an aspect of which is thus economically disadvantageous.

In the present invention, as to a content of the oxidation product of the diol which is used for the production of a polymer with a good color, in general, an upper limit thereof is preferably not more than 10,000 ppm, more preferably not more than 5,000 ppm, still more preferably not more than 3,000 ppm, and most preferably not more than 2,000 ppm. On the other hand, though a lower limit thereof is not particularly limited, in general, it is preferably 1 ppm or more. For the reason of economy of the purification step, the lower limit is more preferably 10 ppm or more, and more preferably 100 ppm or more.

In the present invention, the diol is in general purified by means of distillation.

As the biomass-resource-derived polyurethane according to the present invention, all of polyurethanes produced from polyester polyols which are produced through a reaction of components composed mainly of various compounds falling within the scopes of the above-enumerated dicarboxylic acid units and diol units are included in the polyurethane of the present invention.

As a typical polyester polyol which is used for the production of the biomass-resource-derived polyurethane according to the present invention, specifically, the following polyester polyols can be exemplified.

Examples of a polyester polyol using succinic acid include a polyester polyol composed of succinic acid and ethylene glycol, a polyester polyol composed of succinic acid and 1,3-propylene glycol, a polyester polyol composed of succinic acid and 2-methyl-1,3-propanediol, a polyester polyol composed of succinic acid and 3-methyl-1,5-pentanediol, a polyester polyol composed of succinic acid and neopentyl glycol, a polyester polyol composed of succinic acid and 1,6-hexamethylene glycol, a polyester polyol composed of succinic acid and 1,4-butanediol, a polyester polyol composed of succinic acid and 1,4-cyclohexanedimethanol, and the like.

Examples of a polyester polyol using oxalic acid include a polyester polyol composed of oxalic acid and ethylene glycol, a polyester polyol composed of oxalic acid and 1,3-propylene glycol, a polyester polyol composed of oxalic acid and 2-methyl-1,3-propanediol, a polyester polyol composed of oxalic acid and 3-methyl-1,5-pentanediol, a polyester polyol composed of oxalic acid and neopentyl glycol, a polyester polyol composed of oxalic acid and 1,6-hexamethylene glycol, a polyester polyol composed of oxalic acid and 1,4-butanediol, a polyester polyol composed of oxalic acid and 1,4-cyclohexanedimethanol, and the like.

Examples of a polyester polyol using adipic acid include a polyester polyol composed of adipic acid and ethylene glycol, a polyester polyol composed of adipic acid and 1,3-propylene glycol, a polyester polyol composed of adipic acid and 2-methyl-1,3-propanediol, a polyester polyol composed of adipic acid and 3-methyl-1,5-pentanediol, a polyester polyol composed of adipic acid and neopentyl glycol, a polyester polyol composed of adipic acid and 1,6-hexamethylene glycol, a polyester polyol composed of adipic acid and 1,4-butanediol, a polyester polyol composed of adipic acid and 1,4-cyclohexanedimethanol, and the like.

In addition to the above, polyester polyols obtained using the foregoing dicarboxylic acid in combination are also preferable. Examples thereof include a polyester polyol composed of succinic acid, adipic acid, and ethylene glycol, a polyester polyol composed of succinic acid, adipic acid, and 1,4-butanediol, a polyester polyol composed of terephthalic acid, adipic acid, and 1,4-butanediol, a polyester polyol composed of terephthalic acid, succinic acid, and 1,4-butanediol, and the like.

In general, a molecular weight calculated from a hydroxyl value of such a polyester polyol is preferably from 500 to 5,000, more preferably from 700 to 4,000, and still more preferably from 800 to 3,000. When the molecular weight is 500 or more, when formed into a polyurethane resin, satisfactory physical properties are obtained. In addition, when the molecular weight is not more than 5,000, the viscosity of the polyester polyol does not become excessively high, and handling properties are good.

Furthermore, in general, a molecular weight distribution of such a polyester polyol as measured by GPC (gel permeation chromatography) is preferably from 1.2 to 4.0, more preferably from 1.5 to 3.5, and still more preferably from 1.8 to 3.0. When the molecular weight distribution is 1.2 or more, economy of the production is enhanced. In addition, when it is not more than 4.0, physical properties of the polyurethane resin are enhanced.

In addition, these polyester polyols may be used solely, or may be used in admixture of two or more kinds thereof. Furthermore, the polyester polymer may be used upon being mixed with a polyether polyol or a polycarbonate diol, or may be used upon being modified into a copolymer polyol.

Furthermore, in the case where the polyurethane reaction is carried out in the absence of a solvent, such a polyester polyol is preferably liquid at 40° C., and more preferably, a viscosity thereof at 40° C. is not more than 15,000 mPa·s.

(3) Organic Acid Having a pKa Value at 25° C. of not More than 3.7:

Examples of the organic acid having a pKa value at 25° C. of not more than 3.7 include organic acids described in Kagaku-binran (Chemical Handbook) (Basic Edition), pp. 1054 to 1058, Maruzen Publishing Co., Ltd. (1966); and *CRC Handbook of Chemistry and Physics*, 75$^{th}$ Edition, p.8-43 to p.8-56, CRC Press (1995).

Of these, a lower limit value of the pKa value is preferably 2.0 or more, more preferably 2.5 or more, and especially preferably 3.1 or more; and an upper limit value thereof is preferably not more than 3.5. Incidentally, among the organic acids, there are compounds displaying two or more pKa values. In the present invention, the pKa value of a compound as referred to in that case means the lowest value.

Though the organic acid having a pKa value at 25° C. of not more than 3.7 is not particularly limited, organic acids having three or more active hydrogen groups per molecule are preferable; malic acid, citric acid, tartaric acid, and a mixture thereof are more preferable; malic acid and a mixture thereof are the most preferable; and malic acid especially preferable.

In particular, in the case of using succinic acid as a raw material, there may be the case where malic acid is contained in the raw material succinic acid depending upon the production method of succinic acid. In such case, the production of a polyester polyol can also be carried out by as a combination with a diol component choosing malic acid-containing succinic acid and using it as it is or using it by adding malic acid according to the need.

In the organic acid having three or more active hydrogen groups per molecule, its pKa value tends to decrease due to effect of OH group at $\alpha$ position of carbonyl group as compared with that of an organic acid having not more than 2 active hydrogen groups per molecule.

For example, when the case of malic acid having a pKa value at 25° C. of 3.4 is explained as an example, if the content of malic acid in the succinic acid is more than 1,000 ppm, a branched structure in the polyester polyol increases. Therefore, gelation at the time of a polyurethane reaction and unexpected polymerization are liable to occur, so that not only the control of the reaction becomes difficult, but a linear polyurethane having excellent physical properties may not be obtained. In addition, conversely, if malic acid is not contained at all, the mechanical strength tends to decrease depending upon the application.

For the foregoing reasons, as to the content of the organic acid having a pKa value at 25° C. of not more than 3.7, in general, a lower limit value thereof is more than 0 ppm, preferably 0.001 ppm or more, more preferably 0.01 ppm or more, still more preferably 0.05 ppm or more, especially preferably 0.07 ppm or more, and most preferably 0.1 ppm or more relative to the dicarboxylic acid. An upper limit thereof is in general not more than 1,000 ppm, preferably not more than 800 ppm, and more preferably not more than 600 ppm.

In the present description, an analysis (detection) method of the organic acid having a pKa value at 25° C. of not more than 3.7 is classified into two cases, and the analysis is carried out in accordance with these cases.

In the case where the content of the organic acid is 100 ppm or more, the analysis is carried out by means of high performance liquid chromatography. Specifically, a column equivalent to ULTRON PS-80H, 8.0 mm I.D.×30 cm, manufactured by Shinwa Chemical Industries Ltd. is used; a column temperature is kept at 60° C.; a 0.1% perchloric acid aqueous solution is used as an eluent and allowed to pass at a flow rate of 1.0 mL/min; and each of components is fractionated. For the detection, an RI detector and a UV detector are used depending upon the sensitivity of the component to be analyzed.

In the case where the content of the organic acid is less than 100 ppm, the analysis is carried out by means of LC-MS. Specifically, a column equivalent to MCI GEL CK08EH (8.0 mm×300 mm L.), manufactured by Mitsubishi Chemical Corporation is used; a column temperature is kept at 60° C.; a 0.02% formic acid aqueous solution is used as an eluent and allowed to pass at a flow rate of 1.0 mL/min; and fractionated components are successively introduced into an MS detector. The fractionated component having been introduced into the MS detector is detected by ESI-SIM (negative) as a pseudo-molecular ion signal of the component which is an analysis object. As an organic acid peak, S/N=3 was defined as a detection limit.

When the content of the organic acid in the dicarboxylic acid is more than 1,000 ppm, the viscosity of the polyester polyol as a polyurethane raw material becomes high; the handling operability is deteriorated; and a polyurethane having poor mechanical characteristics such as flexibility, elasticity, etc. with an abnormally high molecule weight, an abnormally large molecular weight distribution, due to gelation or the like at the time of polyurethane reaction tends to be formed. In addition, when the content of the organic acid in the dicarboxylic acid is more than 1,000 ppm, a scatter of the content is liable to be caused, and not only physical properties of the resulting polyurethane are variable, but even in the production step, the stable operation tends to become difficult.

When the content of the organic acid in the dicarboxylic acid is more than 0 ppm, not only the matter that the purification step of the dicarboxylic acid becomes complicated is prevented, an aspect of which is thus economically advantageous, and when formed into a polyurethane, the mechanical strength can be enhanced.

(4) Polyisocyanate Compound:

Examples of the polyisocyanate compound which is used in the present invention include aromatic diisocyanates such as 2,4- or 2,6-tolylene diisocyanate, xylylene diisocyanate, 4,4'-diphenylmethane diisocyanate (MDI), p-phenylene diisocyanate, 1,5-naphthalene diisocyanate, tolidine diisocyanate, etc.; aromatic ring-containing aliphatic diisocyanates such as $\alpha,\alpha,\alpha',\alpha'$-tetramethylxylylene diisocyanate, etc.; aliphatic diisocyanates such as methylene diisocyanate, propylene diisocyanate, lysine diisocyanate, 2,2,4- or 2,4,4-trimethylhexamethylene diisocyanate, 1,6-hexamethylene diisocyanate, etc.; alicyclic diisocyanates such as 1,4-cyclohexane diisocyanate, methylcyclohexane diisocyanate (hydrogenated TDI), 1-isocyanato-3-isocyanatomethyl-3,5,5-trimethylcyclohexane (IPDI), 4,4'-dicyclohexylmethane diisocyanate, isopropylidenedicyclohexyl-4,4'-diisocyanate, etc.; and the like. These may be used solely or in combination of two or more kinds thereof.

In the present invention, aromatic polyisocyanates having especially high reactivity are preferable, and in particular, tolylene diisocyanate (TDI) and diphenylmethane diisocyanate (hereinafter sometimes referred to as "MDI") are preferable. In addition, polyisocyanates in which a part of NCO groups thereof is modified into urethane, urea, burette, allophanate, carbodiimide, oxazolidone, amide, imide, or the like may be used, and furthermore, polynuclear bodies include those containing an isomer other than the foregoing.

In general, a use amount of such a polyisocyanate compound is preferably from 0.1 equivalents to 10 equivalents, more preferably from 0.8 equivalents to 1.5 equivalents, and still more preferably from 0.9 equivalents to 1.05 equivalents to 1 equivalent of the hydroxyl group of the polyester polyol, and the hydroxyl group and amino group of the chain extender.

When the use amount of the polyisocyanate is not more than 10 equivalents, the matter that an unreacted isocyanate group causes an undesirable reaction is prevented, and desired physical properties are easily obtainable. In addition, when the use amount of the polyisocyanate is 0.1 equivalents or more, the molecular weights of the polyurethane and the polyurethaneurea become sufficiently large, so that desired performances can be revealed.

In the present invention, a chain exchanger having two or more active hydrogens may be used according to the need. The chain extender is classified mainly into a compound having two or more hydroxyl groups and a compound having two or more amino groups. Of these, a short-chain polyol, specifically a compound having two or more hydroxyl groups, is preferable for the polyurethane application; and a polyamide compound, specifically a compound having two or more amino groups, is preferable for the polyurethane application.

In addition, in the polyurethane resin of the present invention, when a compound having a molecular weight (number average molecular weight) of not more than 500 is used in combination as the chain extender, rubber elasticity of a polyurethane elastomer is enhanced, and hence, such is more preferable from the standpoint of physical properties.

Examples of the compound having two or more hydroxyl groups include aliphatic glycols such as ethylene glycol, diethylene glycol, triethylene glycol, propylene glycol, dipropylene glycol, tripropylene glycol, 1,3-propanediol, 1,2-butanediol, 1,3-butanediol, 1,4-butanediol, 2,3-butanediol, 3-methyl-1,5-pentanediol, neopentyl glycol, 2-methyl-1,3-propanediol, 2-methyl-2-propyl-1,3-propanediol, 2-butyl-2-ethyl-1,3-propanediol, 1,5-pentanediol, 1,6-hexanediol, 2-methyl-2,4-pentanediol, 2,2,4-trimethyl-1,3-pentanediol, 2-ethyl-1,3-hexanediol, 2,5-dimethyl-2,5-hexanediol, 2-butyl-2-hexyl-1,3-propanediol, 1,8-octanediol, 2-methyl-1,8-octanediol, 1,9-nonanediol, etc.; alicyclic glycols such as bishydroxymethylcyclohexane, etc.; aromatic ring-containing glycols such as xylylene glycol, bishydroxyethoxybenzene, etc.; and the like.

Examples of the compound having two or more amino groups include aromatic diamines such as 2,4- or 2,6-tolylenediamine, xylylenediamine, 4,4'-diphenylmethanediamine, etc.; aliphatic diamines such as ethylenediamine, 1,2-propylenediamine, 1,6-hexanediamine, 2,2-dimethyl-1,3-propanediamine, 2-methyl-1,5-pentanediamine, 1,3-diaminopentane, 2,2,4- or 2,4,4-trimethylhexanediamine, 2-butyl-2-ethyl-1,5-pentanediamine, 1,8-octanediamine, 1,9-nonanediamine, 1,10-decanediamine, etc.; alicyclic diamines such as 1-amino-3-aminomethyl-3,5,5-trimethylcyclohexane (IPDA), 4,4'-dicyclohexylmethanediamine (hydrogenated MDA), isopropylidenecyclohexyl-4,4'-diamine, 1,4-diaminocyclohexane, 1,3-bisaminomethylcyclohexane, etc.; and the like.

Of these, ethylene glycol, diethylene glycol, 1,3-propanediol, 1,4-butanediol, 3-methyl-1,5-pentanediol, neopentyl glycol, 2-methyl-1,3-propanediol, isophoronediamine, hexamethylenediamine, ethylenediamine, propylenediamine, 1,3-diaminopentane, and 2-methyl-1,5-pentanediamine are preferable in the present invention.

In these chain extenders, when the aromatic polyisocyanate is used, one having a hydroxyl group is preferable, whereas when the aliphatic polyisocyanate is used, one having an amino group is preferable. In addition, these chain extenders may be used solely or in combination of two or more kinds thereof. Though a use amount of such a chain extender is not particularly limited, in general, it is preferably 0.1 equivalents or more and not more than 10 equivalents to 1 equivalent of the polyester polyol.

When the use amount of the chain extender is not more than 10 equivalents, the matter that the resulting polyurethane and polyurethaneurea resins become excessively rigid is prevented, desired characteristics are obtained, and the resins are easily soluble in a solvent, so that processing is easy. In addition, when the use amount of the chain extender is 0.1 equivalents or more, the resulting polyurethane and polyurethane resins do not become excessively soft, sufficient strength and elasticity recovering performance or elasticity retaining performance are obtained, and high-temperature characteristics can be enhanced.

In addition, for the purpose of controlling the molecular weight of the polyurethane resin, a chain terminator having one active hydrogen group can be used according to the need. Examples of such a chain terminator include aliphatic monools having a hydroxyl group, such as ethanol, propanol, butanol, hexanol, etc.; and aliphatic monoamines having an amino group, such as diethylamine, dibutylamine, monoethanolamine, diethanolamine, etc. These may be used solely or in combination of two or more kinds thereof.

In addition, for the purpose of increasing the heat resistance or strength of the polyurethane resin, a crosslinking agent having three or more active hydrogen groups can be used according to the need. Trimethylolpropane, glycerin and isocyanate modified products thereof, polymeric MDI, and the like can be used as such a crosslinking agent.

(5) Other Additives:

Furthermore, other additives than those described above may be added to the polyurethane resin of the present invention according to the need. Examples of such additives include antioxidants such as CYANOX 1790 (manufactured by Cyanamid), IRGANOX 245 and IRGANOX 1010 (all of which are manufactured by Ciba Specialty Chemicals), Sumilizer GA-80 (manufactured by Sumitomo Chemical Co., Ltd.), 2,6-dibutyl-4-methylphenol (BHT), etc., light stabilizer such as TINUVIN 622LD and TINUVIN 765 (all of which are manufactured by Ciba Specialty Chemicals), SANOL LS-2626 and LS-765 (all of which are manufactured by Sankyo Co., Ltd.), etc., ultraviolet ray absorbers such as TINUVIN 328 and TINUVIN 234 (all of which are manufactured by Ciba Specialty Chemicals), etc., silicone compounds such as dimethylsiloxane/polyoxyalkylene copolymers, additives and reactive flame retardants such as red phosphorus, organophosphorus compounds, phosphorus- and halogen-containing organic compounds, bromine- or chlorine-containing organic compounds, ammonium polyphosphate, aluminum hydroxide, antimony oxide, etc., colorants such as pigments, e.g., titanium dioxide, dyes, carbon black, etc., hydrolysis inhibitors such as carbodiimide compounds, etc., fillers such as short glass fibers, carbon fibers, alumina, talc, graphite, melamine, China clay, etc., lubricants, oils, surfactants, other inorganic extenders, organic solvents, and the like. In addition, a blowing agent such as water, alternative to CFCs, etc. may be added. In particular, the blowing agent is useful for polyurethane foams for shoe sole.

<Production Method of Biomass-Resource-Derived Polyester Polyol>

A production method of a biomass-resource-derived polyester polyol according to the present invention, which contains, as constituent units, an aliphatic diol unit, a dicarboxylic acid unit, and an organic acid unit having a pKa value at 25° C. of not more than 3.7, is not particularly limited so far as a polyester polyol can be produced such that the dicarboxylic acid contains at least one component derived from biomass resources; and that the content of the organic acid unit is more than 0% by mole and not more than 0.09% by mole relative to the dicarboxylic unit.

An example of the production method of a biomass-resource-derived polyester polyol according to the present invention is hereunder described.

In particular, a dicarboxylic acid component derived from biomass resources may be mixed with a dicarboxylic acid component not derived from biomass resources and used as the dicarboxylic acid. In the case of using the mixture, adipic acid, sebacic acid, and the like are preferable from the standpoints of costs and performance.

In addition, it is preferable to use ethylene glycol, diethylene glycol, 1,4-butanediol, and the like solely or in admixture as the diol unit from the standpoints of costs and performance, but it should not be construed that the present invention is limited thereto.

In the present invention, in using, as a polyester polyol forming reaction raw material, the dicarboxylic acid derived from biomass resources and/or diol obtained by the foregoing method, the polyester polyol may be produced within a reaction tank in which an oxygen concentration during the polyester polyol production reaction is controlled to not more than a specified value.

According to this, coloration of the polyester polyol due to an oxidation reaction of the nitrogen compound that is an impurity, or coloration of the polyester polyol due to a diol oxidation reaction of 2-(4-hydroxybutyloxy)tetrahydrofuran or the like as formed by an oxidation reaction of 1,4-butanediol in the case of using, for example, 1,4-butanediol as the diol, can be suppressed, and therefore, a polyester polyol with a good color can be produced.

The foregoing production reaction is defined as a reaction of from, after charging the raw materials in an esterification reaction tank, a point of time of starting temperature rising to produce a polymer having a desired viscosity in the reaction tank at ordinary pressure or under reduced pressure until subjecting the reaction tank to pressure recovery from the reduced pressure to ordinary pressure or higher.

As to an oxygen concentration in the reaction tank during the production reaction, though a lower limit thereof is not particularly limited, in general, it is preferably $1.0 \times 10^{-9}\%$ or more, and more preferably $1.0 \times 10^{-7}\%$ or more relative to a total volume of the reaction tank. In general, an upper limit thereof is preferably not more than 10%, more preferably not more than 1%, still more preferably not more than 0.1% and most preferably not more than 0.01%. When the oxygen concentration is $1.0 \times 10^{-9}\%$ or more, the matter that the control step becomes complicated can be prevented. In addition, when the oxygen concentration is not more than 10%, the matter that coloration of the polyester polyol becomes conspicuous can be prevented.

In the case of feeding the dicarboxylic acid derived from biomass resources into the reaction tank, so far as the dicarboxylic acid is a solid, it can be fed into the reaction tank as it stands in a state of the fed solid. It is important to carry out the operation before the start of the esterification reaction such that the oxygen concentration within the reaction tank is a desired concentration during the feeding or after the feeding. At the time of regulating the oxygen concentration, there may be the case where the raw material dicarboxylic acid is blown up into a gas phase, thereby making the operation difficult. Thus, it is desirable to adopt a particle size (average particle size) of the raw material dicarboxylic acid at the time of feeding of from 0.01 mm to 100 mm, and preferably from 0.05 mm to 10 mm.

In addition, in feeding the dicarboxylic acid derived from biomass resources as the polyester polyol raw material into the reaction tank, the dicarboxylic acid can be fed in a molten state, or a dissolving tank with the raw material polyol or a suitable solvent is provided before the reaction tank, and the dicarboxylic acid can be fed as a raw material solution or suspension into the reaction tank.

In addition, in using the dicarboxylic acid derived from biomass resources as a polyester polyol raw material, the oxygen concentration and humidity at the time of taking a method of transferring the dicarboxylic acid from the storage tank into the reactor may be controlled. According to this, corrosion within a transfer pipe to be caused due to a sulfur component that is an impurity can be prevented. Furthermore, coloration to be caused due to an oxidation reaction of a nitrogen source can be suppressed, and a polyester polyol with a good color can be produced.

Specifically, examples of the kind of the transfer pipe include known metal-made transfer pipes or those in which a lining of glass, a resin, or the like is applied to an inner surface thereof, glass-made or resin-made containers, and the like. From the standpoint of strength or the like, metal-made transfer pipes or those in which a lining is applied are preferable.

As a material of the metal-made tank, known materials are used. Specifically, examples thereof include carbon steels, ferrite based stainless steels, martensite based stainless steels such as SUS410, etc., austenite based stainless steels such as SUS310, SUS304, SUS316, etc., clad steels, cast iron, copper, copper alloys, aluminum, Inconel, Hastelloy, titanium, and the like.

As to an oxygen concentration within the transfer pipe, though a lower limit thereof is not particularly limited, in general, it is preferably 0.00001% or more, and more preferably 0.01% or more relative to the total volume of the transfer pipe. On the other hand, in general, a lower limit thereof is preferably not more than 16%, more preferably not more than 14%, and still more preferably not more than 12%. When the oxygen concentration is 0.00001% or more, the matter that the investment in plant and equipment or the control step becomes complicated is prevented, an aspect of which is thus economically advantageous. On the other hand, when the oxygen concentration is not more than 16%, coloration of the produced polyester polyol can be suppressed.

As to a humidity within the transfer pipe, though a lower limit thereof is not particularly limited, in general, it is preferably 0.0001% or more, more preferably 0.001% or more, still more preferably 0.01% or more, and most preferably 0.1% or more; and an upper limit thereof is preferably not more than 80%, more preferably not more than 60%, and still more preferably not more than 40%.

When the humidity within the transfer pipe is 0.0001% or more, the matter that the control step becomes complicated is prevented, an aspect of which is thus economically advantageous. In addition, when the humidity within the transfer pipe is not more than 80%, corrosion of the storage tank or piping can be prevented. Furthermore, when the humidity within the transfer pipe is not more than 80%, problems such as attachment of the dicarboxylic acid onto the storage tank or piping, blocking of the dicarboxylic acid, etc. can be prevented, and corrosion of the piping to be caused due to such an attachment phenomenon can be suppressed.

As to a temperature within the transfer pipe, in general, a lower limit thereof is preferably −50° C. or higher, and more preferably 0° C. or higher. On the other hand, in general, an upper limit thereof is preferably not higher than 200° C., more preferably not higher than 100° C., and still more preferably not higher than 50° C. When the temperature is −50° C. or higher, the storage costs can be suppressed. In addition, when the temperature is not higher than 200° C., concurrence of a dehydration reaction of the carboxylic acid or the like can be prevented.

In general, a pressure within the transfer pipe is preferably from 0.1 kPa to 1 MPa, and from the viewpoint of operability, it is more preferably 0.05 MPa or more and not more than 0.3 MPa.

A use amount of the diol which is used at the time of producing a polyester polyol is substantially equimolar to the diol amount necessary for obtaining a polyester polyol having a desired molecular weight relative to the molar number of the dicarboxylic acid or a derivative thereof. In general, in view of the fact that distillation is revealed during the ester condensation and/or ester exchange reaction, it is preferable to use the diol in an excessive amount by from 0.1 to 20% by mole.

In addition, it is preferable to carry out the ester condensation and/or ester exchange reaction in the presence of an esterification catalyst. An addition timing of the esterification catalyst is not particularly limited, and the esterification catalyst may be added at the time of charging the raw materials, or it may be added after removing water to some extent or at the time of starting the pressure reduction.

In the case where the dicarboxylic acid is used as a raw material, the raw material dicarboxylic acid displays autocatalysis, and therefore, it is general that the reaction is allowed to proceed at the beginning of the reaction without adding a catalyst, and, when the rate becomes insufficient in conformity with a formation rate of formed water, an esterification catalyst which is different from the raw material component is added. At that time, as to a timing of adding the esterification catalyst which is different from the raw material component, when a progressing esterification reaction rate is preferably not more than 1/3, and more preferably not more than 1/5 as compared with the esterification reaction rate at the beginning of the reaction without adding a catalyst, the reaction is easily controllable, and hence, such is preferable.

Examples of the esterification catalyst include compounds containing a metal element belonging to the Group 1 to the Group 14 of the periodic table exclusive of hydrogen and carbon. Specifically, examples thereof include organic group-containing compounds such as carboxylates, alkoxy salts, organic sulfonates, β-diketonate salts, etc., each containing at least one metal selected from the group consisting of titanium, zirconium, tin, antimony, cerium, germanium, zinc, cobalt, manganese, iron, aluminum, magnesium, calcium, strontium, sodium, and potassium; inorganic compounds such as oxides or halides of the foregoing metals, etc.; and mixtures thereof.

There may be the case where the foregoing catalyst component is contained in the polyester polyol raw material derived from biomass resources from the reasons described above. In that case, such a raw material may be used as it is as a metal-containing raw material without particularly purifying the raw material.

Of these, metal compounds containing titanium, zirconium, germanium, zinc, aluminum, magnesium, or calcium, and mixtures thereof are preferable. Above of all, titanium compounds, zirconium compounds, and germanium compounds are especially preferable. In addition, for the reason that when the catalyst is in a molten or dissolved state at the time of an esterification condensation reaction, the reaction rate increases, the catalyst is preferably a compound which is in a liquid form at the time of an esterification reaction or soluble in a desired polyester polyol.

As the titanium compounds, for example, tetraalkyl titanates are preferable. Specifically, examples thereof include tetra-n-propyl titanate, tetraisopropyl titanate, tetra-n-butyl titanate, tetra-t-butyl titanate, tetraphenyl titanate, tetracyclohexyl titanate, tetrabenzyl titanate, and mixtures thereof.

In addition, examples of the preferred titanium compound include titanium (oxy)acetylacetonate, titanium tetraacetylacetonate, titanium (diisopropoxide)acetylacetonate, titanium bis(ammonium lactato)dihydroxide, titanium bis(ethyl acetoacetato)diisopropoxide, titanium (triethanolaminato) isopropoxide, polyhydroxytitanium stearate, titanium lactate, titanium triethanolaminate, butyl titanate dimer, and the like.

Moreover, examples of the preferred titanium compound also include titanium oxide and a composite oxide containing titanium and silicon (for example, a titania/silica composite oxide). Of these, tetra-n-propyl titanate, tetraisopropyl titanate, tetra-n-butyl titanate, titanium (oxy)acetylacetonate, titanium tetraacetylacetonate, titanium bis(ammonium lactato) dihydroxide, polyhydroxytitanium stearate, titanium lactate, butyl titanate dimer, titanium oxide, and a titania/silica composite oxide are preferable; tetra-n-butyl titanate, titanium (oxy)acetylacetonate, titanium tetraacetylacetonate, polyhydroxytitanium stearate, titanium lactate, butyl titanate dimer, and a titania/silica composite oxide are more preferable; and tetra-n-butyl titanate, polyhydroxytitanium stearate, titanium (oxy)acetylacetonate, titanium tetraacetylacetonate, and a titania/silica composite oxide are especially preferable.

Specifically, examples of the zirconium compound include zirconium tetraacetate, zirconium acetate hydroxide, zirconium tris(butoxy)stearate, zirconyl diacetate, zirconium oxalate, zirconyl oxalate, potassium zirconium oxalate, polyhydroxyzirconium stearate, zirconium ethoxide, zirconium tetra-n-propoxide, zirconium tetraisopropoxide, zirconium tetra-n-butoxide, zirconium tetra-t-butoxide, zirconium tributoxyacetylacetonate, and mixtures thereof.

Furthermore, for example, zirconium oxide, or for example, a composite oxide containing zirconium and silicon is also preferably used as the zirconium compound. Of these, zirconyl diacetate, zirconium tris(butoxy)stearate, zirconium tetraacetate, zirconium acetate hydroxide, ammonium zirconium oxalate, potassium zirconium oxalate, polyhydroxyzirconium stearate, zirconium tetra-n-propoxide, zirconium tetraisopropoxide, zirconium tetra-n-butoxide, and zirconium tetra-t-butoxide are preferable; zirconyl diacetate, zirconium tetraacetate, zirconium acetate hydroxide, zirconium tris(butoxy)stearate, ammonium zirconium oxalate, zirconium tetra-n-propoxide, and zirconium tetra-n-butoxide are more preferable; and zirconium tris(butoxy)stearate are especially preferable.

Specifically, examples of the germanium compound include inorganic germanium compounds such as germanium oxide, germanium chloride, etc.; and organic germanium compounds such as a tetraalkoxygermanium, etc. From the standpoints of costs and easiness of availability, germanium oxide, tetraethoxygermanium, tetrabutoxygermanium, and the like are preferable, with germanium oxide being especially preferable.

As to a use amount of the catalyst in the case of using a metal compound as such an esterification catalyst, in general, a lower limit value thereof is preferably 1 ppm or more, and more preferably 3 ppm or more, and in general, an upper limit value thereof is not more than 30,000 ppm, more preferably not more than 1,000 ppm, still more preferably not more than 250 ppm, and especially preferably not more than 130 ppm, in terms of a metal amount relative to the formed polyester polyol. What the amount of the used catalyst is not more than 30,000 ppm is not only economically advantageous but enables the polyester polyol to have enhanced thermal stability. In addition, what the amount of the used catalyst is 1 ppm or more enables the polyester polyol to have enhanced polymerization activity.

As to a reaction temperature of the esterification condensation reaction and/or ester exchange reaction between the dicarboxylic acid component and the diol component, in general, a lower limit thereof is preferably 150° C. or higher, and more preferably 180° C. or higher, and in general, an upper limit thereof is preferably not higher than 260° C., and more preferably not higher than 250° C. A reaction atmosphere is in general an inert gas atmosphere of nitrogen, argon, or the like. In general, a reaction pressure is preferably from ordinary pressure to 10 Torr, and more preferably from ordinary pressure to 100 Torr.

As to a reaction time, in general, a lower limit thereof is preferably 10 minutes or longer, and in general, an upper limit thereof is preferably not longer than 10 hours, and more preferably not longer than 5 hours.

In addition, the esterification reaction is carried out at ordinary pressure or under reduced pressure, the timing of pressure reduction and the degree of pressure reduction are adopted chiefly in conformity with a reaction rate and a boiling point of the raw material diol, or in the case of making an azeotropic solvent coexistent, in conformity with a boiling point thereof. In order to carry out a preferred stable operation, it is preferable that the reaction is carried out at ordinary pressure at the time of starting an esterification reaction, and after a progressing esterification reaction rate reaches not more than ½ of the initial rate, the pressure reduction is started at a preferred timing. The pressure reduction may be started either before or after the catalyst adding timing.

In the present invention, as a reaction apparatus for producing a polyester, known vertical or horizontal stirring tank reactors can be used. For example, there is exemplified a method of using a stirring tank type reactor equipped with an exhaust pipe for pressure reduction connecting a vacuum pump and a reactor to each other. In addition, a method in which a condenser is coupled with the exhaust pipe for pressure reduction connecting a vacuum pump and a reactor to each other, and volatile components formed during the polycondensation reaction and unreacted raw materials are recovered by the condenser is preferable.

In an industrial production method, the reaction is decided chiefly by an outflow of the distillation component, thereby determining an end point of the reaction, and an appropriate outflow depends upon a boiling point (easiness of flowing out) of the raw material polyol component. In general, the reaction end point is determined by an acid number during the reaction. In addition, as the case may be, a treatment of regulating the polyester polyol so as to have a desired molecular weight (recondensation or depolymerization by the addition of the raw material diol) is added. Th reaction control is determined on the basis of the acid number. In addition, in general, the reaction end point is decided in conformity with the outflow. However, after completion of the reaction, an acid number of such a product is measured, and when the acid number falls outside the target standard, the esterification reaction is again carried out, thereby regulating it so as to have a desired acid number.

The acid number which is defined as the reaction end is preferably not more than 1.0, more preferably not more than 0.5, and still more preferably not more than 0.2. In addition, a preferred water content at the time of completion of the reaction is preferably not more than 200 ppm, more preferably not more than 100 ppm, and still more preferably not more than 50 ppm. In order to regulate appropriate acid number and water content at the time of end point, as the case may be, the reaction can also be carried out by adding an azeotropic solvent capable of causing azeotropy with water and forming two phases and not having active hydrogen. Though this azeotropic solvent is not particularly limited so far as it has such performances, it is generally an inexpensive aromatic compound such as benzene, toluene, etc.

In addition, after the polyester polyol production reaction, the polyester polyol can be stored as it is or fed for the polyurethane reaction, or after carrying out a treatment of deactivating the added catalyst, the polyester polyol can be stored or fed for the polyurethane reaction. Though a method of deactivating the added catalyst is not particularly limited, it is preferable to use a catalyst deactivating additive such as phosphite trimester, etc., and a method involving a concern that the polyester polyol structure is broken, such as a water treatment, etc., is rather unsuitable.

<Biomass-Resource-Derived Polyester Polyol>

The biomass-resource-derived polyester polyol according to the present invention is a polyester polyol containing, as constituent units, at least an aliphatic diol unit, a dicarboxylic acid unit, and an organic acid unit having a pKa value at 25° C. of not more than 3.7, wherein the dicarboxylic acid contains at least one component derived from biomass resources, and the content of the organic acid unit is more than 0% by mole and not more than 0.09% by mole relative to the dicarboxylic acid unit.

Though a lower limit of the content of the organic acid unit is not particularly limited, it is preferably $9 \times 10^{-8}$% by mole or more, more preferably $9 \times 10^{-7}$% by mole or more, still more preferably $4.5 \times 10^{-6}$% by mole or more, especially preferably $6.3 \times 10^{-6}$% by mole or more, and most preferably $9 \times 10^{-6}$% by mole or more; and an upper limit thereof is preferably not more than $9 \times 10^{-2}$% by mole, more preferably not more than $7.2 \times 10^{-2}$% by mole, and still more preferably not more than $5.4 \times 10^{-2}$% by mole, relative to the dicarboxylic acid unit.

When the content of the organic acid unit is more than 0.09% by mole, the viscosity of the polyester polyol as a polyurethane raw material becomes high; the handling operability is deteriorated; and a polyurethane having an abnormally high molecule weight, an abnormally large molecular weight distribution, or poor mechanical characteristics such as flexibility, elasticity, etc. due to gelation or the like at the time of polyurethane reaction tends to be formed. In addition, when the content of the organic acid unit is more than 0.09% by mole, a scatter of the content is liable to be caused, and not only physical properties of the resulting polyurethane are variable, but even in the production step, the stable operation tends to become difficult.

In addition, when the content of the organic acid unit is more than 0% by mole, not only the matter that the purification step of the dicarboxylic acid becomes complicated is prevented, an aspect of which is thus economically advantageous, but when formed into a polyurethane, the mechanical strength can be enhanced.

Though the polyester polyol of the present invention is not particularly limited on whether it is a solid or a liquid (in a liquid state) at ordinary temperature, it is preferably a liquid at ordinary temperature from the standpoint of handling.

In general, a molecular weight calculated from hydroxyl number of such a polyester polyol is preferably from 500 to 5,000, more preferably from 700 to 4,000, and still more preferably from 800 to 3,000. When the molecular weight is 500 or more, when formed into a polyurethane resin, satisfactory physical properties are obtainable. In addition, when the molecular weight is not more than 5,000, the viscosity of the polyester polyol does not become excessively high, and handling properties are enhanced.

Furthermore, in general, a molecular weight distribution of such a polyester polyol as measured by GPC (gel permeation chromatography) is preferably from 1.2 to 4.0, more preferably from 1.5 to 3.5, and still more preferably from 1.8 to 3.0. When the molecular weight distribution is 1.2 or more, the economy of the production is enhanced, whereas when it is not more than 4.0, physical properties of the polyurethane resin can be enhanced.

It is preferable that a content of nitrogen atoms contained in the polyester polyol of the present invention other than those contained in covalently bonded functional groups is not more than 1,000 ppm relative to the mass of the polyester polyol. The content of nitrogen atoms contained in the polyester polyol of the present invention other than those contained in covalently bonded functional groups is preferably not more than 500 ppm, more preferably not more than 100 ppm, and still more preferably not more than 50 ppm. Above all, it is preferably not more than 40 ppm, more preferably not more than 30 ppm, and most preferably not more than 20 ppm.

The content of nitrogen atoms contained in the polyester polyol of the present invention other than those contained in covalently bonded functional groups is mainly derived from nitrogen atoms in the raw material. When the content of nitrogen atoms contained in the polyester polyol of the present invention other than those contained in covalently bonded functional groups is not more than 20 ppm, coloration becomes small.

In general, the polyester polyol produced in the present invention is preferably a polyester polyol with less coloration. As to a value of the polyester polyol of the present invention as expressed by a Hazen color number (APHA value: in conformity with JIS-K0101), an upper limit thereof is preferably not more than 50, more preferably not more than 40, still more preferably not more than 30, and especially preferably not more than 25. On the hand, though a lower limit thereof is not particularly limited, in general, it is preferably 1 or more, more preferably 2 or more, and still more preferably 5 or more.

As to a polyester polyol having an APHA value of not more than 50, for example, there is brought such an advantage that the use application of films, sheets, and the like of a polyurethane using the polyester polyol as a raw material is not restricted. On the other hand, as to a polyester polyol having an APHA value of 1 or more, a production process of producing a polyester polyol is not complicated, does not require extremely expensive investment in plant and equipment, and is economically advantageous.

<Production Method of Biomass-Resource-Derived Polyurethane>

The production method of a biomass-resource-derived polyurethane in the present invention is a method for producing a polyurethane including at least a step of reacting an aliphatic diol and a dicarboxylic acid to produce a polyester polyol; and a step of reacting the polyester polyol and a polyisocyanate compound, wherein the dicarboxylic acid that is a raw material contains at least one component derived from biomass resources, and a content of an organic acid having a pKa value at 25° C. of not more than 3.7 in the dicarboxylic acid is more than 0 ppm and not more than 1,000 ppm. There are no particular limitations so far as at least the biomass-resource-derived polyurethane can be produced such that the dicarboxylic acid to be used as a raw material falls within the foregoing range.

In the production method of a biomass-resource-derived polyurethane according to the present invention, it is necessary to use raw materials under specified conditions. Furthermore, by combining various production conditions in processes until producing a polyurethane, a biomass-resource-derived polyurethane containing, as constituent units, at least an aliphatic diol unit, a dicarboxylic acid unit, a polyisocyanate unit, and an organic acid unit having a pKa value at 25° C. of not more than 3.7, wherein the dicarboxylic acid contains at least one component derived from biomass resources, and a content of the organic acid unit is more than 0% by mole and not more than 0.09% by mole relative to the dicarboxylic acid unit, can be first produced.

An example of the production method of a biomass-resource-derived polyurethane according to the present invention is hereunder described.

The polyurethane of the present invention may be produced through a reaction in a bulk state, namely in the absence of a solvent, or through a reaction in a solvent having excellent solubility against the polyurethane, such as aprotic polar solvents.

An example of the production method in the copresence of an aprotic solvent is hereunder described, but the production method is not particularly limited so far as it is carried out in the copresence of an aprotic solvent. Examples of the production method include one-stage method and two-stage method.

The one-stage method as referred to herein is a method of reacting a biomass-resource-derived polyester polyol, a polyisocyanate compound, and a chain extender together.

In addition, the two-stage method as referred to herein is a method of first reacting a biomass-resource-derived polyester polyol and a polyisocyanate compound to prepare a prepolymer, both ends of which are terminated with an isocyanate group, and then reacting the prepolymer with a chain extender (hereinafter also referred to as "isocyanate group-terminated two-stage method"). In addition, examples of the two-stage method include a method in which after preparing a prepolymer, both ends of which are terminated with a hydroxyl group, the prepolymer and a polyisocyanate are reacted.

Above all, the isocyanate group-terminated two-stage method goes through a step of reacting a polyester polyol with 1 equivalent or more of a polyisocyanate in advance, thereby preparing an intermediate, both ends of which are terminated with an isocyanate, corresponding to a soft segment of the polyurethane.

The two-stage method has such a characteristic feature that when the prepolymer is once prepared and then reacted with the chain extender, the molecular weight of the soft segment portion is easily regulated, distinct phase separation between the soft segment and the hard segment is easily achieved, and performances as an elastomer are easily revealed.

In particular, in the case where the chain extender is a diamine, this chain extender considerably differs in the reaction rate with the isocyanate group from the hydroxyl group of the polyester polyol. Therefore, it is more preferable to carry out polyurethaneurea formation by the prepolymer method.

[One-Stage Method]

The one-stage method as referred to herein is also called a one-shot method and is a method in which the biomass-resource-derived polyester polyol, the polyisocyanate compound, and the chain extender are charged together and reacted. The use amounts of the respective compounds may be the same as those described above.

In the one-shot method, a solvent may be used, or may not be used. In the case where a solvent is not used, the polyisocyanate component and the polyol component may be stirred and mixed using a low-pressure foaming machine or a high-pressure foaming machine, or using a high-speed rotary mixer.

In the case of using a solvent, examples of the solvent include ketones such as acetone, methyl ethyl ketone, methyl isobutyl ketone, cyclohexanone, etc.; ethers such as dioxane, tetrahydrofuran, etc.; hydrocarbons such as hexane, cyclohexane, etc.; aromatic hydrocarbons such as toluene, xylene, etc.; esters such as ethyl acetate, butyl acetate, etc.; halogenated hydrocarbons such as chlorobenzene, trichlene, perchlene, etc.; aprotic polar solvents such as γ-butyrolactone, dimethyl sulfoxide, N-methyl-2-pyrrolidone, N,N-dimethylformamide, N,N-dimethylacetamide, etc.; and mixtures of two or more kinds thereof.

In the present invention, of these organic solvents, in the case of producing a polyurethane, aprotic polar solvents are preferable from the viewpoint of solubility, an aspect of which is a characteristic feature of the present invention.

Furthermore, specific examples of the preferred aprotic polar solvent are exemplified. That is, methyl ethyl ketone, methyl isobutyl ketone, N,N-dimethylacetamide, N,N-dimethylformamide, N-methyl-2-pyrrolidone, and dimethyl sulfoxide are more preferable, with N,N-dimethylformamide and N,N-dimethylacetamide being especially preferable.

In the case of the one-shot method (reaction in one stage), as to an NCO/active hydrogen group (polyester polyol and chain extender) reaction equivalent ratio, in general, a lower limit thereof is preferably 0.50, and more preferably 0.8; and in general, an upper limit thereof is preferably 1.5, and more preferably 1.2.

When the reaction equivalent ratio is not more than 1.5, the matter that the excessive isocyanate groups cause side reactions to give unpreferable influences to physical properties of the polyurethane can be prevented. In addition, where the reaction equivalent ratio is 0.50 or more, the molecular weight of the resulting polyurethane sufficiently increases, and the generation of problems on strength or thermal stability can be prevented.

In general, the respective components are preferably reacted at from 0 to 100° C. It is preferable that this temperature is regulated by the amount of the solvent, reactivity of the raw materials used, reaction equipment, and the like. Too low temperatures are undesirable because the reaction proceeds too slowly, and the raw materials and polymerization product have low solubility, resulting in poor productivity. In addition, too high temperatures are undesirable because side reactions and decomposition of the polyurethane resin occur. The reaction may be carried out under reduced pressure while degassing.

In addition, a catalyst, a stabilizer, or the like may be added for the reaction according to the need.

Examples of the catalyst include triethylamine, tributylamine, dibutyltin dilaurate, stannous octylate, acetic acid, phosphoric acid, sulfuric acid, hydrochloric acid, sulfonic acids, and the like.

Examples of the stabilizer include 2,6-dibutyl-4-methylphenol, distearyl thiodipropionate, di-β-naphthylphenylenediamine, tri(dinonylphenyl) phosphite, and the like.

[Two-Stage Method]

The two-stage method is also called a prepolymer process. In this method, in general, the polyisocyanate component and the polyol ingredient are reacted in a reaction equivalent ratio of preferably from 1.0 to 10.00 in advance, thereby producing a prepolymer. Subsequently, a polyisocyanate component and an active hydrogen compound component such as a polyhydric alcohol, an amine compound, etc. are added to the prepolymer, thereby carrying out a two-stage reaction. In particular, a method in which the polyol component is reacted with a polyisocyanate compound in an amount of at least one equivalent to the polyol ingredient to form a prepolymer, both ends of which are terminated with NCO, and a short-chain diol or a diamine that is a chain extender is then allowed to act on the prepolymer to obtain a polyurethane, is useful.

In the two-stage method, a solvent may be used, or may not be used. In the case of using a solvent, examples of the solvent include ketones such as acetone, methyl ethyl ketone, methyl isobutyl ketone, cyclohexanone, etc.; ethers such as dioxane, tetrahydrofuran, etc.; hydrocarbons such as hexane, cyclohexane, etc.; aromatic hydrocarbons such as toluene, xylene, etc.; esters such as ethyl acetate, butyl acetate, etc.; halogenated hydrocarbons such as chlorobenzene, trichlene, perchlene, etc.; aprotic polar solvents such as γ-butyrolactone, dimethyl sulfoxide, N-methyl-2-pyrrolidone, N,N-dimethylformamide, N,N-dimethylacetamide, etc.; and mixtures of two or more kinds thereof.

In the present invention, of these organic solvents, in the case of producing a polyurethane, aprotic polar solvents are preferable from the viewpoint of solubility, an aspect of which is a characteristic feature of the present invention. Furthermore, specific examples of the preferred aprotic polar solvent are exemplified. That is, N,N-dimethylacetamide, N,N-dimethylformamide, N-methyl-2-pyrrolidone, and dimethyl sulfoxide are more preferable, with N,N-dimethylformamide and N,N-dimethylacetamide being especially preferable.

In synthesizing a prepolymer terminated with an isocyanate group, any of the following methods may be used: (1) a polyisocyanate compound is first reacted directly with the polyester polyol without using a solvent, to synthesize a prepolymer, and this prepolymer is used as it is; (2) a prepolymer is synthesized by the method (1) and then dissolved in a solvent, followed by providing for the use; and (3) a solvent is used from the beginning to react a polyisocyanate and a glycol.

In the case of the method (1), it is important in the present invention that a polyurethane is obtained in the state of coexisting with a solvent by a method in which in allowing a chain extender to act, the chain extender is dissolved in a solvent, or the prepolymer and the chain extender are simultaneously introduced into a solvent, or the like.

As to an NCO/active hydrogen group (polyester polyol) reaction equivalent ratio, in general, a lower limit thereof is preferably 1, and more preferably 1.1; and in general, an upper limit thereof is preferably 10, more preferably 5, and still more preferably 3.

A use amount of the chain extender is not particularly limited. In general, a lower limit thereof is preferably 0.8, and more preferably 1, and in general, an upper limit thereof is preferably 2, and more preferably 1.2, relative to the equivalent of the NCO group contained in the prepolymer.

When the foregoing ratio is not more than 2, the matter that the excessive isocyanate groups cause side reactions to give unpreferable influences to physical properties of the polyurethane can be prevented. In addition, where the foregoing ratio is 0.8 or more, the molecular weight of the resulting polyurethane sufficiently increases, and the generation of problems on strength or thermal stability can be prevented.

In addition, a monofunctional organic amine or alcohol may be allowed to coexist at the time of reaction.

In general, the respective components are reacted preferably at from 0 to 250° C. It is preferable that this temperature is regulated by the amount of the solvent, reactivity of the raw materials used, reaction equipment, and the like. Too low temperatures are undesirable because the reaction proceeds too slowly, and the raw materials and polymerization product have low solubility, resulting in poor productivity. In addition, too high temperatures are undesirable because side reactions and decomposition of the polyurethane resin occur. The reaction may be carried out under reduced pressure while degassing.

In addition, a catalyst, a stabilizer, or the like may be added for the reaction according to the need.

Examples of the catalyst include triethylamine, tributylamine, dibutyltin dilaurate, stannous octylate, acetic acid, phosphoric acid, sulfuric acid, hydrochloric acid, sulfonic acids, and the like. However, in the case where the chain extender is one having high reactivity such as short-chain aliphatic amines, etc., it is preferable that the reaction is carried out without adding a catalyst.

Examples of the stabilizer include 2,6-dibutyl-4-methylphenol, distearyl thiodipropionate, di-β-naphthylphenylenediamine, tri(dinonylphenyl) phosphite, and the like.

When a generally used petroleum-derived dicarboxylic acid is used at the time of polyurethane production, the reaction is hardly controlled at the time of urethane reaction, the molecular weight becomes abnormally high due to gelation or the like, or the molecular weight distribution becomes abnormally large. However, when the foregoing dicarboxylic acid in which the amount of the organic acid to be contained falls within a specified range is used, astonishingly, it is possible to control the reaction at the time of urethane reaction, and the foregoing problems do not occur. In consequence, since a linear biomass-resource-derived polyurethane can be produced, handling properties of the polyurethane are enhanced. In addition, by regulating a formulation depending upon an application thereof, the polyurethane can be used in a wide field.

At the time of polyurethane production of the present invention, in the case of adding a crosslinking agent for an application requiring heat resistance or strength, it is preferable to make its addition amount larger than that at the time of using a generally used petroleum-derived dicarboxylic acid. In addition, since the viscosity of the polyurethane obtained at the time of polyurethane production of the present invention is low, at the time of post-treatment and processing of the polyurethane, it is preferable to make the temperature slightly lower than that at the time of using petroleum-derived succinic acid, resulting in favorable handling properties, stability and economy.

<Artificial Leather/Synthetic Leather>

An artificial leather or synthetic leather of the present invention is described in detail. The artificial leather or synthetic leather is composed of, as major constituent elements, a base cloth, an adhesive layer, and a skin layer. The skin layer is a skin layer blended liquid obtained by mixing the polyurethane resin obtained in the present invention with other resins, an antioxidant, an ultraviolet ray absorber, etc. to fabricate a polyurethane resin solution, which is then mixed with a coloring agent, an organic solvent, etc. To the polyurethane resin solution, in addition to the above, a hydrolysis inhibitor, a pigment, a dye, a flame retardant, a filler, a crosslinking agent, etc. can be added according to the need.

Examples of other resins include polyurethane resins other than that of the present invention, poly(meth)acrylate resins, vinyl chloride-vinyl acetate based copolymers, vinyl chloride-vinyl propionate based copolymers, polyvinyl butyral based resins, cellulose based resins, polyester resins, epoxy resins, phenoxy resins, polyamide resins, and the like.

Examples of the crosslinking agent include polyisocyanate compounds such as organic polyisocyanates, crude MDI, a TDI adduct of trimethylolpropane, triphenylmethane isocyanate, etc. and the like.

Examples of the base cloth include Tetoron/rayon, a napped cotton cloth, a knitted cloth, a nylon tricot cloth, and the like. In addition, examples of the adhesive include two-pack polyurethane resins composed of a polyurethane resin, a polyisocyanate compound, and a catalyst.

In addition, examples of the polyisocyanate compound include a TDI adduct of trimethylolpropane and the like. Examples of the catalyst include amine based or tin based catalysts.

Next, the production method of a synthetic leather according to the present invention is described. That is, the above-obtained polyurethane resin is mixed with other resin, etc. to fabricate a polyurethane resin solution, which is then mixed with a coloring agent, etc. to fabricate a skin layer blended liquid. Subsequently, this blended liquid is coated on a release paper and dried; an adhesive is further coated to form an adhesive layer; a napped cloth or the like is laminated thereon and dried; and after aging at room temperature for a few days, the release paper is released, thereby obtaining the synthetic leather of the present invention.

The artificial leather/synthetic leather of the present invention can be used for clothing, shoe, bag, and the like.

The polyurethane for shoe sole according to the present invention is described in detail. Examples of the production method of a polyurethane foam for shoe sole using the foregoing polyester polyol include mainly (1) a method in which at the time of reacting a polyisocyanate component and a polyol component and expanding the reaction product to produce a polyurethane foam, as the polyol component, the foregoing polyester polyol-containing polyol component is used (hereinafter referred to as "Production Method A"); and (2) a method in which at the time of reacting an isocyanate prepolymer obtained by reacting a polyisocyanate component and a polyol component with a polyol component and expanding the reaction product to produce a polyurethane foam, the foregoing polyester polyol-containing polyol component is used as the polyol component which is used as a raw material of the isocyanate prepolymer (hereinafter referred to as "Production Method B").

First of all, Production Method A is described. In Production Method A, as the polyol component which is used at the time of reacting a polyisocyanate component and a polyol component and expanding the reaction product to produce a polyurethane foam, the foregoing polyester polyol-containing polyol component is used.

The polyol component can contain, in addition to the foregoing polyester polyol, other polyester polyol, a polyether polyol such as polypropylene glycol, polyoxytetramethylene glycol, etc., polycaprolactone polyol, polycarbonate polyol, and the like. These may be used solely, or may be used in admixture of two or more kinds thereof.

Representative examples of the polyisocyanate component which is used for Production Method A include an isocyanate prepolymer and the like. The isocyanate prepolymer is obtained by stirring and reacting a polyisocyanate monomer and a polyol in the presence of an excessive polyisocyanate monomer in the usual way.

Specific examples of the polyisocyanate monomer include polyisocyanate compounds such as tolylene diisocyanate, m-phenylene diisocyanate, p-phenylene diisocyanate, xylylene diisocyanate, diphenylmethane diisocyanate, hexamethylene diisocyanate, isophorone diisocyanate, polymethylene polyphenyl diisocyanate, dimethyl-4,4-biphenylene diisocyanate, etc.; and modified products thereof, for example, carbodiimide modified products, etc.

These may be used solely, or may be used in admixture of two or more kinds thereof. Of these, a single use of 4,4-diphenylmethane diisocyanate or a joint use of 4,4-diphenylmethane diisocyanate with a carbodiimide modified product thereof is preferable.

As to an NCO % of the isocyanate prepolymer, from the viewpoint of preventing the matter that a viscosity thereof is high so that molding by a low-pressure foaming machine becomes difficult, the NCO % is preferably 15% or more, and more preferably 17% or more; and from the viewpoint of preventing the matter that the viscosity is low so that weighing accuracy of the foaming machine becomes low, the NCO % is preferably not more than 25%, more preferably not more than 23%, and still more preferably not more than 22%.

The isocyanate prepolymer assumes a liquid at a temperature of 15° C. or higher and can be discharged even at a low temperature, and therefore, a polyurethane foam can be easily produced even at a molding temperature of, for example, from 40 to 50° C.

In Production Method A, at the time of reacting the polyisocyanate component and the polyol component, it is preferable to regulate a proportion between the both such that an isocyanate index is from 95 to 110.

In Production Method A, a polyurethane foam can be produced by mixing and stirring the polyisocyanate component and the polyol component by a molding machine, injecting the mixture into a molding die, and expanding it. More specifically, a polyurethane foam can be produced by regulating a temperature of the polyol component to a temperature of usually about 40° C. by using, for example, a tank, etc. and then mixing and reacting the polyol component and the polyisocyanate component using a foaming machine such as an automatic mixing and injection type foaming machine, an automatic mixing and injection type foaming machine, etc.

In addition, according to Production Method A, a urethane shoe sole can be molded by mixing the polyisocyanate component and the polyol component and then molding the mixture by a foaming machine temperature-controlled to usually from about 40 to 50° C.

Next, Production Method B is described. In Production Method B, at the time of reacting an isocyanate prepolymer obtained by reacting a polyisocyanate component and a polyol component with a polyol component and expanding the reaction product to produce a polyurethane foam, as the polyol component which is used at the time of preparing an isocyanate prepolymer, the foregoing polyester polyol-containing polyol component is used.

As the polyester polyol contained in the polyol component which is used at the time of preparing an isocyanate prepolymer, the polyester polyol of the present invention is used. Examples of the polyisocyanate component that is a production raw material of the isocyanate prepolymer include the polyisocyanate monomer which is used in Production Method A, and the like.

Examples of the polyisocyanate monomer include the same materials as the specific examples of the polyisocyanate monomer used in Production Method A. Incidentally, of these exemplified materials, a single use of 4,4-diphenylmethane diisocyanate or a joint use of 4,4-diphenylmethane diisocyanate with a carbodiimide modified product thereof is preferable.

In Production Method B, by using the foregoing polyester polyol, the viscosity of the resulting isocyanate prepolymer can be suitably kept, so that a polyurethane foam having excellent mechanical strength can be obtained.

The polyol component can contain, in addition to the foregoing polyester polyol, other polyester polyol. Examples of the other polyester polyol component include the same materials as those used in Production Method A.

A content of the foregoing polyester polyol in the polyol component is preferably from 10 to 100% by weight, and more preferably from 50 to 100% by weight. A content of the other polyester polyol is preferably from 0 to 90% by weight, and more preferably from 0 to 50% by weight.

In addition, in general, it is preferable to regulate a proportion between the polyisocyanate component and the polyol component such that an NCO group/OH group equivalent ratio is preferably from about 5 to 30.

Subsequently, an isocyanate prepolymer is obtained by mixing, stirring and reacting the polyisocyanate component and the polyol component and optionally, an additive in the usual way.

As to an NCO % of the thus obtained isocyanate prepolymer, from the viewpoint of reducing the viscosity to make it easy to achieve molding by a low-pressure foaming machine, the NCO % is preferably 12% or more, and more preferably 14% or more; and from the viewpoint of imparting an appropriate viscosity to enhance weighing accuracy of the foaming machine, the NCO % is preferably not more than 25%, more preferably not more than 23%, and still more preferably not more than 22%.

The isocyanate prepolymer assumes a liquid at a temperature of 15° C. or higher and can be discharged even at a low temperature, and therefore, a polyurethane foam can be favorably produced even at a molding temperature of, for example, from 40 to 50° C.

Subsequently, a polyurethane foam is obtained by reacting and expanding the isocyanate prepolymer and the polyol component.

Examples of the polyol component which is used for the reaction with the isocyanate prepolymer include the same materials as other polyols than the polyester polyol which is used as the polyol component in Production Method A.

Incidentally, to the polyol component which is used for the reaction with the isocyanate prepolymer, a chain extender, a blowing agent, a polyuretahne catalyst, a stabilizer, pigment, or the like may be properly added in an appropriate amount, according to the need.

In Production Method B, at the time of reacting the polyisocyanate component and the polyol component, it is preferable to regulate a proportion between the both such that an isocyanate index is from 95 to 110.

In addition, in Production Method B, a polyurethane foam can be produced by mixing and stirring the isocyanate prepolymer and the polyol component and optionally, an additive by a molding machine, injecting the mixture into a molding die, and expanding it. More specifically, a polyurethane foam can be produced by regulating a temperature of the polyol component to a temperature of usually about 40° C. by using, for example, a tank, etc. and then mixing and reacting it with the isocyanate prepolymer using a foaming machine such as an automatic mixing and injection type foaming machine, an automatic mixing and injection type foaming machine, etc.

In addition, according to Production Method B, a urethane shoe sole can be molded by mixing the isocyanate prepolymer and the polyol component and then molding the mixture by a foaming machine temperature-controlled to usually from about 40 to 50° C. In the case of adopting Production Method B for producing a shoe sole, as to the resulting polyurethane foam, nevertheless an amount of the resin peer unit volume decreases, mechanical strength such as tensile strength, tear strength, etc. can be sufficiently enhanced.

Thus, from the viewpoints of revealing sufficient mechanical strength and contriving to realize low density, a density of a molded article of the polyurethane foam obtained by Production Method A or Production Method B is preferably from 0.15 to 1.0 g/cm$^3$, and more preferably from 0.2 to 0.4 g/cm$^3$.

<Physical Properties of Biomass-Resource-Derived Polyurethane>

The biomass-resource-derived polyurethane according to the present invention is a polyurethane containing, as constituent units, at least an aliphatic diol unit, a dicarboxylic acid unit, and an organic acid unit having a pKa value at 25° C. of not more than 3.7, wherein the dicarboxylic acid contains at least one component derived from biomass resources, and the content of the organic acid unit is more than 0% by mole and not more than 0.09% by mole relative to the dicarboxylic acid unit.

Though a lower limit of the content of the organic acid unit is not particularly limited, it is preferably $9 \times 10^{-8}$% by mole or more, more preferably $9 \times 10^{-7}$% by mole or more, still more preferably $4.5 \times 10^{-6}$% by mole or more, especially preferably $6.3 \times 10^{-6}$% by mole or more, and most preferably $9 \times 10^{-6}$% by mole or more; and an upper limit thereof is preferably not more than $9 \times 10^{-2}$% by mole, more preferably not more than $7.2 \times 10^{-2}$% by mole, and still more preferably not more than $5.4 \times 10^{-2}$% by mole, relative to the dicarboxylic acid unit.

When the content of the organic acid unit is more than 0.09% by mole, a polyurethane having an abnormally high molecule weight, an abnormally large molecular weight distribution, or poor mechanical characteristics such as flexibility, elasticity, etc. due to gelation or the like at the time of polyurethane reaction tends to be formed. In addition, when the content of the organic acid unit is more than 0.09% by mole, a scatter of the content is liable to be caused, and not only physical properties of the resulting polyurethane are variable, but even in the production step, the stable operation tends to become difficult. On the other hand, when the content of the organic acid unit is more than 0% by mole, a polyurethane having high mechanical strength tends to be formed.

In addition, it is preferable that the biomass-resource-derived polyurethane according to the present invention has the following physical properties.

When the physical properties of the polyurethane of the present invention are described by reference to a polyurethane between an aliphatic diol and an aliphatic dicarboxylic acid, such as polybutylene succinate or polybutylene succinate adipate, it is preferable that the polyurethane has very broad physical property characteristics such as a tensile stress of from 5 to 15 MPa and an elongation at break of from 300 to 1,500%.

In addition, in the case where a specified application is subjective, a polyurethane having arbitrary broad range characteristics exceeding the foregoing range region can be formed. These characteristics can be arbitrarily regulated by varying the kind of the polyurethane raw material or additive, the polymerization condition, the molding condition, and the like depending upon the use purpose.

Ranges of representative physical property values which the polyurethane of the present invention has are hereunder disclosed in detail.

As to a composition ratio of the polyurethane copolymer, it is preferable that a molar ratio of the diol unit and the dicarboxylic acid unit is substantially equal.

As to a content of the sulfur atom in the polyurethane of the present invention, an upper limit thereof is preferably not more than 50 ppm, more preferably not more than 5 ppm, still more preferably not more than 3 ppm, and most preferably not more than 0.3 ppm as reduced into an atom relative to the mass of the polyurethane. On the other hand, though a lower limit thereof is not particularly limited, it is preferably 0.0001 ppm or more, more preferably 0.001 ppm or more, still more preferably 0.01 ppm or more, especially preferably 0.05 ppm or more, and most preferably 0.1 ppm or more.

When the content of the sulfur atom is not more than 50 ppm, the thermal stability or hydrolysis resistance of the polyurethane can be enhanced. In addition, when the content of the sulfur atom is 0.001 ppm or more, the matter that the purification costs become conspicuously high is prevented, an aspect of which is thus economically advantageous in the production of a polyurethane.

In the polymer of the present invention, in particular, in the case of a polyurethane using a raw material derived from biomass resources, there is a tendency that a volatile organic component, for example, tetrahydrofuran, acetaldehyde, etc. is liable to be contained in the polyurethane. As to a content of the volatile organic component, in general, an upper limit thereof is preferably not more than 10,000 ppm, more preferably not more than 3,000 ppm, still more preferably not more than 1,000 ppm, and most preferably not more than 500 ppm in the polyurethane. On the other hand, though a lower limit thereof is not particularly limited, in general, it is preferably 1 ppb or more, more preferably 10 ppb or more, and still more preferably 100 ppb or more.

When the amount of the volatile material is not more than 10,000 ppm, the matter that the volatile component causes an odor is prevented, and deterioration of the expansion or storage stability at the time of melt molding can be prevented. On the other hand, when the amount of the volatile material is 1 ppb or more, not only extremely expensive investment in plant and equipment is not required for the purpose of producing a polymer, but a long production time is not required, an aspect of which is thus economically advantageous.

In general, the polyurethane which is produced in the present invention is preferably a polyurethane with less coloration. As to a YI value (in conformity with JIS-K7105) of the polyurethane of the present invention, an upper limit thereof is preferably not more than 20, more preferably not more than 10, still more preferably not more than 5, and especially preferably not more than 3. On the other hand, though a lower limit thereof is not particularly limited, in general, it is preferably −20 or more, more preferably −5 or more, and still more preferably −1 or more.

A polyurethane having a YI value of not more than 20 has such an advantage that the use application of films, sheets, and the like is not restricted. On the other hand, as to a polyurethane having a YI value of −20 or more, a production process of producing a polymer is not complicated, does not require extremely expensive investment in plant and equipment, and is economically advantageous.

A weight average molecular weight of the polyurethane by means of GPC measurement varies depending upon an application, and in general, it is preferably from 10,000 to 1,000,000, more preferably from 50,000 to 500,000, still more preferably from 100,000 to 400,000, and especially preferably from 100,000 to 300,000 in terms of a polyurethane polymerization solution. A molecular weight distribution is preferably from 1.5 to 3.5, more preferably from 1.8 to 2.5, and still more preferably from 1.9 to 2.3 in terms of Mw/Mn.

When the foregoing molecular weight is not more than 1,000,000, the matter that the viscosity of the solution becomes excessively high is prevented, and handling properties are enhanced. In addition, when the molecular weight is 10,000 or more, the matter that the physical properties of the resulting polyurethane are excessively lowered can be prevented. When the molecular weight distribution is 1.5 or more, the matter that the economy of the polyurethane production is excessively deteriorated is prevented, and an elastic modulus of the resulting polyurethane is enhanced. In addition, when the molecular weight distribution is not more than 3.5, the matter that the viscosity of the solution becomes excessively high is prevented, and handling properties are enhanced. In addition, the matter that an elastic modulus of the resulting polyurethane becomes excessively high is prevented, and elastic recovery is enhanced.

As polyurethane molded articles, for example, synthetic leather or artificial leather, polyurethane for shoe sole, films, sheets, tubes, moisture permeable resins, and the like, in general, a weight average molecular weight of the polyurethane is preferably from 10,000 to 1,000,000, more preferably from 50,000 to 500,000, still more preferably from 100,000 to 400,000, and especially preferably from 150,000 to 350,000. A molecular weight distribution is preferably from 1.5 to 3.5, more preferably from 1.8 to 2.5, and still more preferably from 1.9 to 2.3 in terms of Mw/Mn.

When the foregoing molecular weight is not more than 1,000,000, the matter that the viscosity of the solution becomes excessively high is prevented, and handling properties become good. In addition, when the molecular weight is 10,000 or more, the matter that the physical properties of the resulting polyurethane are excessively lowered can be prevented. When the molecular weight distribution is 1.5 or more, the economy of the polyurethane production becomes good, and an elastic modulus of the resulting polyurethane can be enhanced. In addition, when the molecular weight distribution is not more than 3.5, the matter that the viscosity of the solution becomes excessively high is prevented, and handling properties become good. In addition, the matter that an elastic modulus of the resulting polyurethane becomes excessively high is prevented, and elastic recovery can be enhanced.

A solution containing the polyurethane produced in the present invention (hereinafter also referred to as "polyurethane solution") is convenient for processing into films, yarns, etc. because gelation hardly proceeds; the smaller the change in viscosity with a lapse of time, the better the storage stability is; and thixotropy is small.

In general, a content of the polyurethane is preferably from 1 to 99% by weight, more preferably from 5 to 90% by weight, still more preferably from 10 to 70% by weight, and especially preferably from 15 to 50% by weight relative to a total weight of the polyurethane solution having a polyurethane dissolved in an aprotic solvent. When the content of the polyurethane is 1% by weight or more, the removal of a large amount of the solvent is not necessary, and the productivity can be enhanced. In addition, when the content of the polyurethane is not more than 99% by weight, the viscosity of the solution is suppressed, and the operability or processability can be enhanced.

Though the polyurethane solution is not particularly specified, in the case of storing over a long period of time, it is preferable to store it in an inert gas atmosphere of nitrogen, argon, or the like.

<Polyurethane Molded Article/Application>

The polyurethane and urethane prepolymer solution thereof as produced by the present invention can reveal a variety of characteristics and can be widely used as foams, elastomers, coating materials, fibers, adhesives, flooring materials, sealants, medical materials, artificial leathers, and the like.

The polyurethane, polyurethaneurea, and urethane prepolymer solution thereof as produced by the present invention are also usable as a casting polyurethane elastomer. Examples thereof include rolls such as rolling rolls, papermaking rolls, business appliances, pretensioning rolls, etc.; solid tires, casters, or the like for fork lift trucks, automotive vehicle newtrams, carriages, carriers, and the like; and industrial products such as conveyor belt idlers, guide rolls, pulleys, steel pipe linings, rubber screens for ore, gears, connection rings, liners, impellers for pumps, cyclone cones, cyclone liners, etc. In addition, the polyurethane, polyurethaneurea, and urethane prepolymer solution thereof are applicable to belts for OA apparatus, paper feed rolls, squeegees, cleaning blades for copying, snowplows, toothed belts, surf rollers, and the like.

The polyurethane and urethane prepolymer solution thereof as produced by the present invention are also applicable to an application as thermoplastic elastomers. For example, the polyurethane and the urethane prepolymer solution can be used as tubes or hoses in pneumatic apparatus for use in the food and medical fields, coating apparatus, analytical instruments, physicochemical apparatus, constant delivery pumps, water treatment apparatus, industrial robots, and the like and as spiral tubes, hoses for firefighting, etc. In addition, the polyurethane and the urethane prepolymer solution are usable as belts such as round belts, V-belts, flat belts, etc. in various transmission mechanisms, spinning machines, packaging apparatus, printing machines, and the like.

In addition, examples of elastomer applications include heel tops of footwear, shoe soles, apparatus parts such as cup rings, packings, ball joints, bushings, gears, rolls, etc., sports goods, leisure goods, belts of wristwatches, and the like.

Furthermore, examples of automotive parts include oil stoppers, gear boxes, spacers, chassis parts, interior trims, tire chain substitutes, and the like. In addition, examples thereof include films such as key board films, automotive films, etc., curl cords, cable sheaths, bellows, conveying belts, flexible containers, binders, synthetic leathers, dipping products, adhesives, and the like.

The polyurethane and urethane prepolymer solution thereof as produced by the present invention are also applicable to an application as a solvent based two-pack type coating material and can be applied to wood products such as musical instruments, family Buddhist altars, furniture, decorative plywood, sports goods, etc. In addition, the polyurethane and urethane prepolymer solution are also usable as a tar-epoxy-urethane for automotive vehicle repair.

The polyurethane and urethane prepolymer solution thereof as produced by the present invention are usable as a component of moisture-curable one-pack type coating materials, block isocyanate type solvent coating materials, alkyd resin coating materials, urethane-modified synthetic resin coating materials, ultraviolet ray-curable coating materials, and the like.

Such coating materials can be used, for example, as coating materials for plastic bumpers, strippable paints, coating materials for magnetic tapes, overprint varnishes for floor tiles, flooring materials, paper, woodgrained films, and the like, varnishes for wood, coil coatings for high processing, optical fiber protection coatings, solder resists, topcoats for metal printing, base coats for vapor deposition, white coats for food cans, and the like.

The polyurethane and urethane prepolymer solution thereof as produced by the present invention are applicable as an adhesive to shoes, footwear, magnetic tape binders, decorative papers, wood, structural members, and the like. In addition, the polyurethane and urethane prepolymer solution can be used also as a component of adhesives for low-temperature use and hot-melt adhesives.

The polyurethane and urethane prepolymer solution thereof as produced by the present invention are usable as a binder in applications such as magnetic recording media, inks, castings, burned bricks, grafting materials, microcapsules, granular fertilizers, granular agricultural chemicals, polymer cement mortars, resin mortars, rubber chip binders, reclaimed foams, glass fiber sizing, and the like.

The polyurethane and urethane prepolymer solution thereof as produced by the present invention are usable as a component of fiber processing agents for shrink proofing, crease proofing, water repellent finishing, and the like.

The polyurethane, polyurethaneurea, and urethane prepolymer solution thereof as produced by the present invention are applicable as a sealant/caulking material to walls formed by concrete placing, induced joints, the periphery of sashes, wall type PC joints, ALC joints, and joints of boards and as a sealant for composite glasses, sealant for heat-insulating sashes, sealant for automotive vehicles, and the like.

The polyurethane produced by the present invention is suitable for applications to polyurethanes for shoe sole, synthetic leathers, and artificial leathers. In addition, at the time of using the polyurethane produced by the present invention, the polyester polyol component may have a skeleton of adipic acid, sebacic acid, or the like. Furthermore, since such a polyurethane of the present invention is derived from plants and is biodegradable, it is further suitable for non-durable consumer goods such as resins for shoe.

EXAMPLES

The present invention is hereunder described in more detail on the basis of the following Examples, but it should not be construed that the present invention is limited to the following Examples so far as the gist thereof is not deviated. Next, the present invention is described in more detail by reference to the Examples.
(Measuring Method of Molecular Weight of Polyester Polyol)
A number average molecular weight of a polyester polyol was determined in terms of a hydroxyl number (OH number, mg-KOH/g).
(Measuring Method of Molecular Weight of Polyurethane)
As to the measurement of a molecular weight of the resulting polyurethane, a GPC apparatus, manufactured by Shimadzu Corporation (column: TSKgel Super HZM-N, solvent: lithium bromide-added N,N-dimethylacetamide) was used, and a weight average molecular weight as reduced into standard polystyrene was defined as the molecular weight.
(Measuring Method of Physical Properties of Film)
A polyurethane resin test piece was fabricated in a strip form having a width of 10 mm, a length of 100 mm, and a thickness of from 50 to 100 µm and measured using a tensile tester (Tensilon RTC-1210A, manufactured by Orietec Co., Ltd.). The measurement was carried out under a condition of a chuck-to-chuck distance of 20 mm, a tensile rate of 200 mm/min, and a temperature of 23° C. (relative humidity: 55%). The measurement was carried out at ten points per sample, and as to a stress at break and an elongation at break, average values thereof were adopted, respectively.
(APHA Value)
The APHA value was measured by the method in conformity with JIS-K0101.
(Content of Nitrogen Atom)
Several 10 mg of a sample was collected on a quartz boat, the sample was burnt using a total nitrogen analyzer (TN-10 Model, manufactured Mitsubishi Chemical Corporation), and the content of a nitrogen atom was determined by the chemical luminescence method.
(Content of Sulfur Atom)
About 0.1 g of a sample was collected on a platinum boat and burnt in a quartz tubular furnace (AQF-100 (concentration system), manufactured by Mitsubishi Chemical Corporation), and a sulfur content in the combustion gas was absorbed by a 0.1% hydrogen peroxide aqueous solution. Thereafter, a sulfate ion in the absorbed solution was measured using an ion chromatography (ICS-1000 Model, manufactured by Dionex Corporation).
An amount of a terminal carboxyl group is a value obtained by dissolving the resulting polyester in benzyl alcohol and titrated with 0.1 N NaOH, and it is a carboxyl equivalent per $1 \times 10^6$ g.
(YI Value)
The YI value was measured by the method on the basis of JIS-K7105.
(Average Absorbance at from 250 to 300 nm)
The average absorbance was measured using a Hitachi's spectrophotometer UV-3500 and determined according to the method defined in the section of "MODES FOR CARRYING OUT THE INVENTION" of the present description.
(Analysis of Organic Acid and Sugar: High-Performance Liquid Chromatography)
Column: ULTRON PS-80H, 8.0 mm I.D.×30 cm, manufactured by Shinwa Chemical Industries Ltd.
Temperature: 60° C.
Eluent: 0.1% perchloric acid aqueous solution, 1.0 mL/min
Injection amount: 10 µL
Detection: RI detector or UV detector
A detection limit of malic acid was 100 ppm.
[Analysis of Malic Acid as a Minor Component (in the Case of Less than 100 ppm): LC-MS]
Column: MCI GEL CK08EH (8.0 mm×300 mm L.), manufactured by Mitsubishi Chemical Corporation
Temperature: 60° C.
Eluent: 0.02% formic acid aqueous solution, 1.0 mL/min
Injection amount: 3 µL
Detection: ESI-SIM (negative), m/z 133.2 (malic acid pseudo-molecular ion signal)
A detection limit of malic acid was 0.05 ppm at S/N of 3.
(Analysis of Amino Acid)
Apparatus: Hitachi's amino acid analyzer, L-8900
Analysis condition: Biological amino acid separation condition-ninhydrin colorimeter method (at 570 nm and 440 nm)
Standard product: PF (Wako's amino acid mixed liquid, ANII type 0.8 mL+B type 0.8 mL→10 mL)
Injection amount: 10 µL
(Hydrolysis and Analysis for the Determination of the Amount of Protein)
A material obtained by precisely weighing 10 mg or 100 mg of a sample and fixing its volume at 1 mL by pure water was dispensed 200 µL, dried, and heated in a hydrochloric acid atmosphere at 150° C. for one hour, thereby protein was hydrolyzed. This was dried and then again dissolved upon adding 200 µL of pure water. The solution was filtered by a 0.45-µm filter, and the filtrate was subjected to analysis of an amino acid. An increment of a total amino acid amount before and after the hydrolysis was considered to be amount of protein.
The present invention is described in more detail by reference to the following Examples, but it should not be construed that the present invention is limited to these Examples.

Referential Example 1

Fabrication of Succinic Acid Fermenting Strain (A) Extraction of *Brevibacterium flavum* MJ233 Strain Genome DNA:
*Brevibacterium flavum* MJ233 was deposited as an accession number FERM P-3068, on Apr. 28, 1975, with the National Institute of Bioscience and Human-Technology, Agency of Industrial Science and Technology, Ministry of International Trade and Industry (present Patent Microorganism Depositary Center, National Institute of Advanced Industrial Science and Technology) (Center 6, 1-1, Higashi 1-chome, Tsukuba-shi, Ibaraki-ken, 305-8566 Japan) and converted to an international deposit under Budapest Treaty on May 1, 1981 with the accession number FERM BP-1497.
A *Brevibacterium flavum* MJ233 strain was cultured until a late logarithmic growth phase on 10 mL of a medium A (obtained by dissolving 2 g of urea, 7 g of $(NH_4)_2SO_4$, 0.5 g of $KH_2PO_4$, 0.5 g of $K_2HPO_4$, 0.5 g of $MgSO_4.7H_2O$, 6 mg of $FeSO_4.7H_2O$, 6 mg of $MnSO_4.4-5H_2O$, 200 µg of biotin, 200 µg of thiamine, 1 g of yeast extract, 1 g of casamino aid, and 20 g of glucose in 1 L of distilled water), and bacterial cells were gathered by means of centrifugation (10,000 G for 5 minutes).

The resulting bacterial cells were suspended in 0.15 mL of a solution containing a 10 mM NaCl/20 mM tris buffer (pH 8.0)/1 mM EDTA.2Na solution containing lysozyme so as to have a concentration of 10 mg/mL. Subsequently, Proteinase K was added to the foregoing suspension so as to have a final concentration of 100 µg/mL, and the mixture was kept at 37° C. for one hour. Sodium dodecyl sulfate was further added so as to have a final concentration of 0.5%, and the mixture was kept at 50° C. for 6 hours to cause bacteriolysis.

After the addition of an equal amount of a phenol/chloroform solution to the resulting lysate solution and mild shaking at room temperature for 10 minutes, the whole amount of the mixture was centrifuged (5,000 G for 20 minutes at from 10 to 12° C.). The supernatant fraction was collected, to which was then added sodium acetate in a concentration of 0.3 M. To the resulting mixture was added two times the amount of ethanol, followed by mixing. The precipitate recovered by centrifugation (15,000 G for 2 minutes) was washed with 70% ethanol and then air-dried. To the resulting DNA, 5 mL of a 10 mM tris buffer (pH 7.5)/1 mM EDTA.2Na solution was added. The mixture was allowed to stand overnight at 4° C. and then used as a template DNA for the subsequent PCR.

(B) Construction of Plasmid for PC Gene Promoter Substitution:

A DNA fragment of an N-terminated region of a pyruvate carboxylase gene originated from the *Brevibacterium flavum* MJ233 strain was obtained by PCR using the DNA prepared in the above (A) as a template and synthetic DNAs (SEQ ID NO: 1 and SEQ ID NO: 2) designed based on the sequence (Cg10689 of GenBank Database Accession No. BA000036) of the subject gene of a *Corynebacterium glutamicum* ATCC 13032 strain whose entire genomic sequence had been reported. Incidentally, as the DNA of SEQ ID NO: 1, one which was phosphorylated on the 5'-end thereof was used.

Composition of reaction liquid: 1 µL of the template DNA, 0.2 µL of PfxDNA polymerase (manufactured by Invitrogen), 1-fold concentration of an attached buffer, 0.3 µM of each primer, 1 mM of $MgSO_4$ and 0.25 µM of dNTPS were mixed to give a total volume of 20 µL.

Reaction temperature condition: DNA Thermal Cycler PTC-200 (manufactured by MJ Research) was used, and a cycle composed of 94° C. for 20 seconds, 60° C. for 20 seconds and 72° C. for one minute was repeated 35 times. However, heat retention at 94° C. at the first cycle was conducted for 1 minute and 20 seconds, while heat retention at 72° C. at the final cycle was conducted for 4 minutes.

Confirmation of the amplified product was performed by separation by 0.75 agarose (SeaKem GTG agarose, manufactured by FMC BioProducts) gel electrophoresis and subsequent visualization with ethidium bromide staining, whereby about 0.9 kb of a fragment was detected. The desired DNA fragment was recovered from the gel using QIAquick Gel Extraction Kit (manufactured by QIAGEN). This was used as a PC gene N-terminated fragment.

On the other hand, a TZ4 promoter fragment originated from the *Brevibacterium flavum* MJ233 strain, which is constitutionally highly expressed, was prepared by PCR using plasmid pMJPC1 (see JP-A-2005-95169) as a template and synthetic DNAs described in SEQ ID NO: 3 and SEQ ID NO: 4. Incidentally, as the DNA of SEQ ID NO: 4, one which was phosphorylated on the 5'-end thereof was used.

Composition of reaction liquid: 1 µL of the template DNA, 0.2 µL of PfxDNA polymerase (manufactured by Invitrogen), 1-fold concentration of an attached buffer, 0.3 µM of each primer, 1 mM of $MgSO_4$ and 0.25 µM of dNTPS were mixed to give a total volume of 20 µL.

Reaction temperature condition: DNA Thermal Cycler PTC-200 (manufactured by MJ Research) was used, and a cycle composed of 94° C. for 20 seconds, 60° C. for 20 seconds and 72° C. for 30 seconds was repeated 25 times. However, heat retention at 94° C. at the first cycle was conducted for 1 minute and 20 seconds, while heat retention at 72° C. at the final cycle was conducted for 3 minutes.

Confirmation of the amplified product was performed by separation by 1.0% agarose (SeaKem GTG agarose, manufactured by FMC BioProducts) gel electrophoresis and subsequent visualization with ethidium bromide staining, whereby about 0.5 kb of a fragment was detected. The desired DNA fragment was recovered from the gel using QIAquick Gel Extraction Kit (manufactured by QIAGEN). This was used as a TZ4 promoter fragment.

The thus prepared PC gene N-terminated fragment and TZ4 promoter fragment were mixed and ligated using Ligation Kit ver. 2 (manufactured by Takara Shuzo Co., Ltd.); thereafter, the ligated fragment was cleaved with a restriction enzyme PstI and separated by 1.0% agarose (SeaKem GTG agarose, manufactured by FMC BioProducts) gel electrophoresis; and about 1.0 kb of a DNA fragment was recovered using QIAquick Gel Extraction Kit (manufactured by QIAGEN). This was used as a TZ4 promoter/PC gene N-terminated fragment.

Furthermore, this DNA fragment was mixed with a DNA prepared by cleaving *Escherichia coli* plasmid pHSG299 (manufactured by Takara Shuzo Co., Ltd.) with PstI and ligated using Ligation Kit ver. 2 (manufactured by Takara Shuzo Co., Ltd.). The resulting plasmid DNA was transformed with *Escherichia coli* (DH5α strain). The thus obtained recombinant *Escherichia coli* was smeared onto an LB agar medium containing 50 µg/mL of kanamycin and 50 µg/mL of X-Gal. Clones which had formed a white colony on the medium were subjected to liquid culture in the usual way, and the plasmid DNA was then purified. The resulting plasmid DNA was cleaved with a restriction enzyme PstI, whereby about 1.0 kb of an inserted fragment was recognized and named pMJPC17.1.

A DNA fragment of a 5'-upstream region of a pyruvate carboxylase gene originated from the *Brevibacterium flavum* MJ233 strain was obtained by PCR using the DNA prepared in Example 1-(A) as a template and synthetic DNAs (SEQ ID NO: 5 and SEQ ID NO: 6) designed based on the sequence (GenBank Database Accession No. BA000036) of the subject gene of a *Corynebacterium glutamicum* ATCC 13032 strain whose entire genomic sequence had been reported.

Composition of reaction liquid: 1 µL of the template DNA, 0.2 µL of PfxDNA polymerase (manufactured by Invitrogen), 1-fold concentration of an attached buffer, 0.3 µM of each primer, 1 mM of $MgSO_4$ and 0.25 µM of dNTPS were mixed to give a total volume of 20 µL.

Reaction temperature condition: DNA Thermal Cycler PTC-200 (manufactured by MJ Research) was used, and a cycle composed of 94° C. for 20 seconds, 60° C. for 20 seconds and 72° C. for 30 seconds was repeated 35 times. However, heat retention at 94° C. at the first cycle was conducted for 1 minute and 20 seconds, while heat retention at 72° C. at the final cycle was conducted for 5 minutes.

Confirmation of the amplified product was performed by separation by 1.0% agarose (SeaKem GTG agarose, manufactured by FMC BioProducts) gel electrophoresis and subsequent visualization with ethidium bromide staining, whereby about 0.7 kb of a fragment was detected. The desired DNA fragment was recovered from the gel using QIAquick Gel Extraction Kit (manufactured by QIAGEN).

After phosphorylation on the 5'-end of the recovered DNA fragment with T4 Polynucleotide Kinase (manufactured by Takara Shuzo Co., Ltd.), the resulting fragment was bound to an SmaI site of an *Escherichia coli* vector (manufactured by Takara Shuzo Co., Ltd.) by using Ligation Kit ver. 2 (manufactured by Takara Shuzo Co., Ltd.), followed by transformation of *Escherichia coli* (DH5α strain) with the resulting plasmid DNA. The thus obtained recombinant *Escherichia coli* was smeared onto an LB agar medium containing 50 µg/mL of ampicillin and 50 µg/mL of X-Gal. Clones which had formed a white colony on the medium were subjected to liquid culture in the usual way, and the plasmid DNA was then purified. The resulting plasmid DNA was provided for a PCR reaction with, as primers, DNAs expressed by SEQ ID NO: 7 and SEQ ID NO: 6.

Composition of reaction liquid: 1 ng of the foregoing plasmid, 0.2 µL of Ex-TaqDNA polymerase (manufactured by Takara Shuzo Co., Ltd.), 1-fold concentration of an attached buffer, 0.2 µM of each primer and 0.25 µM of dNTPS were mixed to give a total volume of 20 µL.

Reaction temperature condition: DNA Thermal Cycler PTC-200 (manufactured by MJ Research) was used, and a cycle composed of 94° C. for 20 seconds, 60° C. for 20 seconds and 72° C. for 50 seconds was repeated 20 times. However, heat retention at 94° C. at the first cycle was conducted for 1 minute and 20 seconds, while heat retention at 72° C. at the final cycle was conducted for 5 minutes.

In this way, the presence or absence of the thus inserted DNA fragment was recognized. As a result, the plasmid in which about 0.7 kb of the amplified product was recognized was selected and named pMJPC5.1.

Subsequently, the foregoing pMJPC17.1 and pMJPC5.1 were each cleaved with a restriction enzyme XbaI and mixed, followed by ligation using Ligation Kit ver. 2 (manufactured by Takara Shuzo Co., Ltd.). This was cleaved with a restriction enzyme SacI and an restriction enzyme SphI, and the resulting DNA fragment was separated by 0.75% agarose (SeaKem GTG agarose, manufactured by FMC BioProducts) gel electrophoresis, and about 1.75 kb of the DNA fragment was recovered using QIAquick Gel Extraction Kit (manufactured by QIAGEN).

A DNA fragment obtained by inserting the TZ4 promoter between the 5'-upstream region and the N-terminated region of this PC gene was mixed with DNA prepared by cleaving an sacB gene-containing plasmid pKMB1 (see JP-A-2005-95169) with SacI and SphI, followed by ligation using Ligation Kit ver. 2 (manufactured by Takara Shuzo Co., Ltd.). The resulting plasmid DNA was transformed with *Escherichia coli* (DH5α strain). The thus obtained recombinant *Escherichia coli* was smeared onto an LB agar medium containing 50 µg/mL of kanamycin and 50 µg/mL of X-Gal. Clones which had formed a white colony on the medium were subjected to liquid culture in the usual way, and the plasmid DNA was then purified. The resulting plasmid DNA was cleaved with restriction enzymes SacI and SphI, whereby about 1.75 kb of an inserted fragment was recognized and named pMJPC17.2.

(C) Fabrication of PC-Enhanced Strain:

A plasmid DNA to be used for transformation of the *Brevibacterium flavum* MJ233/ALDH (lactate dehydrogenase gene-disrupted strain, see JP-A-2005-95169) was reprepared from an *Escherichia coli* JM110 strain transformed with the plasmid DNA of pMJPC17.2 by a calcium chloride method (see *Journal of Molecular Biology*, 53, 159, 1970). The transformation of the *Brevibacterium flavum* MJ233/ΔLDH strain was performed by an electric pulse method (see *Res. Microbiol.*, Vol. 144, pages 181 to 185, 1993), and the resulting transformant was smeared onto an LBG agar medium [obtained by dissolving 10 g of tryptone, 5 g of yeast extract, 5 g of NaCl, 20 g of glucose and 15 g of agar in 1 L of distilled water) containing 50 µg/mL of kanamycin.

Since the strain grown on this medium was an unreplicable plasmid for pMJPC 17.2 in the *Brevibacterium flavum* MJ233 strain bacterial cell, homologous recombination was caused between the PC gene on the subject plasmid and the same gene on the genome of the *Brevibacterium flavum* MJ233 strain. As a result, kanamycin-resistant gene and sacB gene originated from the subject plasmid must be inserted on the genome.

Subsequently, the foregoing strain obtained by homologous recombination was subjected to liquid culture on an LBG medium containing 25 µg/mL of kanamycin. The culture solution corresponding to about 1,000,000 bacterial cells was smeared onto an LBG medium containing 10% sucrose. As a result, about several ten strains which were presumed to be sucrose-insensitive as a result of loss of the sacB gene caused by the second homologous recombination were obtained. The thus obtained strains include a strain in which the TZ4 promoter originated from pMJPC17.2 has been inserted in the upstream of the PC gene and a strain which has reverted to a wild type.

Whether the PC gene is a promoter substitution type or a wild type can be easily confirmed by providing a bacterial cell obtained by liquid culture on an LBG medium directly for a PCR reaction and detecting the PC gene. When the TZ4 promoter and the PC gene are analyzed using primers for PCR amplification (SEQ ID NO: 8 and SEQ ID NO: 9), 678 bp of the DNA fragment must be recognized in the promoter substitution type. As a result of analysis of the sucrose-insensitive strain by the foregoing method, a strain having the TZ4 promoter inserted thereinto was selected, and the subject strain was named *Brevibacterium flavum* MJ233/PC-5/ΔLDH.

<Preparation of Succinic Acid Fermenting Strain by Jar Fermentor>

(A) Seed Culture:

100 mL of a medium prepared by dissolving 4 g of urea, 14 g of ammonium sulfate, 0.5 g of monopotassium phosphate, 0.5 g of dipotassium phosphate, 0.5 g of magnesium sulfate heptahydrate, 20 mg of ferrous sulfate heptahydrate, 20 mg of manganese sulfate hydrate, 200 µg of D-biotin, 200 µg of thiamin hydrochloride, 1 g of yeast extract, and 1 g of casamino acid in distilled water to make to 1,000 mL was charged in a 500-mL Erlenmeyer flask and then sterilized by heating at 121° C. for 20 minutes. This was cooled to room temperature, to which was then added 4 mL of a % glucose aqueous solution having been sterilized in advance. The above-constructed *Brevibacterium flavum* MJ233/PC-5/ALDH was inoculated, thereby achieving seed culture while shaking (160 rpm) at 30° C. for 16 hours.

(B) Main Culture:

2.0 L of a medium prepared by dissolving 3.0 g of ammonium sulfate, 6.7 g of 85% phosphoric acid, 4.9 g of potassium chloride, 1.5 g of magnesium sulfate heptahydrate, 120 mg of ferrous sulfate heptahydrate, 120 mg of manganese sulfate hydrate, 30.0 g of a corn steep liquid (manufactured by Oji Cornstarch Co., Ltd.), 11.0 g of a 10 N potassium hydroxide aqueous solution, and 2.5 g of an antifoaming agent (CE457, manufactured by NOF Corporation) in distilled water was charged in a 5-L fermentor and then sterilized by heating at 121° C. for 20 minutes.

This was cooled to room temperature, to which was then added 28% ammonia water was added to regulate the pH to 7.0. Thereafter, 15 mL of a 0.2 g/L aqueous solution of each of D-biotin having been filter sterilized in advance and thiamine hydrochloride and 110 mL of a 720 g/L sucrose aqueous solution having been sterilized in advance were added. 100 mL of the foregoing seed culture solution was further added thereto, and the mixture was kept at 30° C. The pH was kept at not more than 7.2 using 28% ammonia water, aeration was carried out at a rate of 3.0 L per minute and at a back pressure of 0.05 MPa, and stirring was carried out at 750 rpm, thereby starting main culture.

After the dissolved oxygen concentration decreased to substantially 0, an increase of the dissolved oxygen concentration again started. When the dissolved oxygen concentration reached 1 ppm, about 5.3 g of a 72% sucrose aqueous solution having been sterilized in advance was added. As a result, the dissolved oxygen concentration again decreased to 0. The addition of a sucrose aqueous solution was repeated by the foregoing method at every time when the dissolved oxygen concentration again increased. The operation was continued until 19 hours after the start of culture.

(C) Succinic Acid Forming Reaction:

1.6 g of 85% phosphoric acid, 1.1 g of magnesium sulfate heptahydrate, 43 mg of ferrous sulfate heptahydrate, 43 mg of manganese sulfate hydrate, and 2.86 g of a 10 N potassium hydroxide aqueous solution were dissolved in distilled water to make to 42 mL, which was then sterilized by heating at 121° C. for 20 minutes, thereby fabricating a reaction concentrated medium.

42 mL of the foregoing reaction concentrated medium having been cooled to room temperature, 530 mL of a 720 g/L sucrose aqueous solution having been sterilized in advance, 1.2 L of sterilized water, 20 mL of a 0.2 g/L aqueous solution of each of D-biotin having been filter sterilized in advance and thiamine hydrochloride, and 675 mL of the culture solution obtained by the foregoing main culture were added in a 5-L jar fermentor, thereby starting a reaction. The reaction was continued at a reaction temperature of 40° C. and at a stirring rotation number of 150 rpm while regulating the pH to 7.35 by successive addition of a neutralizing agent (ammonium hydrogencarbonate: 171 g, 28% ammonia water: 354 g, distilled water: 529 g), and when the residual sucrose in the reaction liquid reached not more than 0.1 g/L, the reaction was completed.

The thus prepared reaction liquid was centrifuged (15,000 G for 5 minutes) to obtain a supernatant (hereinafter sometimes referred to as "succinic acid fermentation liquid"). Results of composition analysis of this supernatant are shown in the following Table 2.

TABLE 2

Composition of succinic acid fermentation liquid

| Product | Accumulated concentration (g/L) | Accumulated concentration (% by weight) |
|---|---|---|
| Succinic acid | 91.3 | 8.65 |
| Malic acid | 9.8 | 0.93 |
| Pyruvic acid | 0.5 | 0.05 |
| Acetic acid | 13.2 | 1.25 |
| Fumaric acid | 2.7 | 0.26 |
| α-Ketoglutaric acid | 1.1 | 0.10 |
| α-Ketovaline | 1.1 | 0.10 |
| Alanine | 2.5 | 0.24 |
| Valine | 0.8 | 0.08 |
| Glutamic acid | 0.1 | 0.01 |
| Trehalose | 1.2 | 0.11 |
| Protein | 1.2 | 0.11 |

(Density: 1.056 g/mL)

The analysis of each of the organic acid and the sugar was carried out by means of high-performance liquid chromatography under conditions equal to those described below.
Column: ULTRON PS-80H, 8.0 mm I.D.×30 cm, manufactured by Shinwa Chemical Industries Ltd.
Temperature: 60° C.
Eluent: 0.1% perchloric acid aqueous solution, 1.0 mL/min
Injection: 3 μL
Detection: RI detector or UV detector
Detection limit of malic acid: 100 ppm Referential Example 2

Succinic acid was produced from the thus obtained succinic acid fermentation liquid that is an aqueous solution containing an aliphatic dicarboxylic acid obtained from a raw material derived from biomass resources.

<Protonation Step>

To 1,500 g of the foregoing succinic acid fermentation liquid, 98% sulfuric acid was added, thereby regulating the pH to 2.5. Here, an addition amount of 98% sulfuric acid was 150 g.

<Extraction Step>

The succinic acid aqueous solution after adding sulfuric acid was mixed with a methyl ethyl ketone (hereinafter sometimes abbreviated as "MEK") using a jacketed static mixture (Noritake 1/4(1)-N40-174-0 (inside diameter φ: 5 mm, element number: 24)) and a jacketed three-tank type settler in which the tanks had a volume of 600 mL, 400 mL, and 300 mL, respectively, followed by liquid-liquid separation to continuously extract succinic acid.

That is, 1,650 g of the succinic acid aqueous solution and 825 g of a 10% hydrated MEK solution having been added with water in advance (MEK solution (weight)/succinic acid aqueous solution (weight)=0.5 (weight/weight)) were fed at a rate of 20 g/min and 10 g/min, respectively into the static mixed, the temperature of which was controlled while allowing warm water at 30° C. to pass through the jacket. The discharged suspension liquid was fed into the first tank of the three-tank type settler, the temperature of which was controlled while allowing warm water at 30° C. to pass through the jacket, and subjected to liquid-liquid separation to continuously discharge a raffinate phase from the bottom of the first tank.

An extract phase was overflowed from a weir between the first tank and the second tank and fed into the second tank. In the second tank, an insoluble component which had not been able to be separated in the first tank was settled in the bottom, and only a clear extract phase was overflowed from a weir between the second tank and the third tank and fed into the third tank. Furthermore, in the third tank, a clear extract phase was overflowed from the neighborhood of a liquid-liquid interface to recover the extract phase. Finally, 688 g of the extract phase, 1,613 g of the raffinate phase, and 173 g of an intermediate phase were recovered. The intermediate phase was subjected to pressure filtration with a PTFE-made membrane filter having an opening of 0.5 μm, thereby recovering 172 of a clear liquid.

<Continuous Extraction>1,613 g of the recovered raffinate phase was continuously extracted with 1,613 g of 10% hydrated MEK (MEK solution (weight)/succinic acid aqueous solution (weight)=1.0 (weight/weight)) by using a jacketed stirring type continuous extraction column having an inside diameter φ of 20 mm and a height of 2 m (theoretical plate number: 10 plates).

Here, the raffinate phase was fed at a rate of 200 g/hr from the column top, and an MEK solution in which the water content had been regulated to 10% by weight in advance was flown at a rate of 200 g/hr from the column bottom. A continuous phase was the raffinate phase, whereas a dispersed phase was the MEK phase (light liquid dispersion). In addition, the temperature of the extraction column was controlled to 30° C. by allowing warm water to pass through the jacket. Finally, 1,777 g of the extract phase was recovered.

The recovered extract phase was combined with the clear liquid recovered by the mixer-settler, and the resulting aliphatic dicarboxylic acid-containing liquid was 2,637 g in total. As a result of analyzing a composition thereof, results shown in the following Table 3 were revealed. The analysis of each of the organic acid and the sugar was carried out by means of high-performance liquid chromatography under conditions equal to those in Table 2.

TABLE 3

Composition of mixed solution of extract phase and clear liquid

| Component | Composition (% by weight) |
|---|---|
| Succinic acid | 4.91 |
| Malic acid | 0.19 |
| Pyruvic acid | 0.00 |
| Acetic acid | 0.71 |
| Fumaric acid | 0.15 |
| α-Ketoglutaric acid | 0.01 |
| α-Ketovaline | 0.02 |
| Alanine | 0.00 |
| Valine | 0.00 |
| Glutamic acid | 0.00 |
| Trehalose | 0.00 |
| Protein | 0.01 |
| MEK | 80.8 |
| Water | 13.2 |

<Distillation>

MEK is substantially removed from the recovered extract phase by means of continuous distillation. Here, the distillate is recovered as an azeotropic composition of MEK and water, namely 11% by weight hydrated MEK; however, there is a concern that succinic acid is deposited depending upon a degree of concentration of the still residue liquid. Then, 190 g of water was added to 2,637 g of the extract phase such that the distillate was 11% by weight MEK, and the still residue liquid was a 30% by weight succinic acid solution.

For the distillation, an atmospheric continuous distillation apparatus equipped with a packed column having an inside diameter φ of 40 mm, in which a coil pack of φ5 mm was packed to a height of 30 cm, a 500-mL round-bottom flask, and a reflux condenser was used. As to the distillation, after making the inside of the system stable by means of total reflux, continuous distillation was carried out at a reflux ratio of 1. The still residue liquid after the distillation was 432 g. In addition, results obtained by analyzing a composition thereof are shown in the following Table 4.

TABLE 4

Composition of still residue liquid after distillation

| Component | Composition (% by weight) |
|---|---|
| Succinic acid | 30.0 |
| Malic acid | 1.14 |
| Pyruvic acid | 0.00 |
| Acetic acid | 4.31 |
| Fumaric acid | 1.14 |
| α-Ketoglutaric acid | 0.05 |
| α-Ketovaline | 0.14 |
| Alanine | 0.01 |

TABLE 4-continued

Composition of still residue liquid after distillation

| Component | Composition (% by weight) |
|---|---|
| Valine | 0.01 |
| Glutamic acid | 0.00 |
| Trehalose | 0.00 |
| Protein | 0.08 |
| MEK | 0.03 |

<Crystallization>

The liquid from which MEK had been distilled off was transferred into a jacketed 500-mL separable flask and kept at 80° C. with stirring while allowing warm water to pass through the jacket. Thereafter, the warm water to be allowed to pass through the jacket was cooled to 20° C. over one hour using programed circulating water baths, thereby crystallizing succinic acid under cooling, and after the temperature reached 20° C., the system was aged at 20° C. for one hour. The resulting slurry was filtered in vacuo to separate a crystallization mother liquid.

Furthermore, the resulting wet cake as a crystallization product was washed with 250 g of cold water, and the washings were recovered to obtain a wet cake composed mainly of succinic acid. Furthermore, the resulting wet cake was dried at 80° C. under a maximum pressure reduction condition using a vacuum dryer, and 114 g of succinic acid was finally recovered. Results obtained by analyzing a composition of the resulting succinic acid are shown in the following Table 5. The analysis of each of the organic acid and the sugar was carried out by means of high-performance liquid chromatography under conditions equal to those in Table 2.

TABLE 5

Composition of obtained succinic acid

| Component | Composition (% by weight) |
|---|---|
| Succinic acid | 95.7 |
| Malic acid | 0.0 |
| Pyruvic acid | 0.0 |
| Acetic acid | 0.1 |
| Fumaric acid | 3.3 |
| α-Ketoglutaric acid | 0.0 |
| α-Ketovaline | 0.0 |
| Alanine | 0.0 |
| Valine | 0.0 |
| Glutamic acid | 0.0 |
| Trehalose | 0.0 |
| Protein | 18 ppm |
| MEK | 0.0 |
| Water | 0.8 |

Succinic acid yield 84%

The crystallization mother liquid and the washings were mixed to prepare 562 g of a recovered liquid, and a composition thereof is shown in the following Table 6. The analysis of each of the organic acid and the sugar was carried out by means of high-performance liquid chromatography under conditions equal to those in Table 2.

TABLE 6

Composition of recovered liquid

| Component | Composition (% by weight) |
|---|---|
| Succinic acid | 3.66 |
| Malic acid | 0.87 |

TABLE 6-continued

Composition of recovered liquid

| Component | Composition (% by weight) |
|---|---|
| Pyruvic acid | 0.00 |
| Acetic acid | 3.29 |
| Fumaric acid | 0.01 |
| α-Ketoglutaric acid | 0.04 |
| α-Ketovaline | 0.10 |
| Alanine | 0.01 |
| Valine | 0.01 |
| Glutamic acid | 0.00 |
| Trehalose | 0.00 |
| Protein | 0.06 |
| MEK | 0.02 |

Referential Example 3

Protonation

To 1,384 g of the foregoing succinic acid fermentation liquid, 98% sulfuric acid was added, thereby regulating the pH to 2.5. Here, an addition amount of 98% sulfuric acid was 138 g. To this protonated liquid, 281 g of the recovered liquid recovered in Referential Example 2, the amount of which is corresponding to a half thereof; was added to prepare 1,803 g of a succinic acid aqueous solution.

<Extraction>

The succinic acid aqueous solution was extracted with 10% hydrated MEK in the same method as that in Referential Example 2. In the mixer-settler, 10% hydrated MEK in an amount of 0.5 weight times the succinic acid aqueous solution was fed at a rate of 20 g/min and 10 g/min, respectively. The recovered intermediate phase was subjected to pressure filtration, and the raffinate phase was further subjected to countercurrent multi-stage continuous extraction with 10% hydrated MEK in an amount of 1.0 weight time the raffinate phase. As a result, 2,882 g of the extract phase and 1,593 g of the raffinate phase were recovered. A composition thereof is as follows.

<Distillation>

Distillation was carried out in the same method as that in Referential Example 2, thereby recovering 438 g of a succinic acid concentrated liquid. A composition thereof is shown in the following Table 7. The analysis of each of the organic acid and the sugar was carried out by means of high-performance liquid chromatography under conditions equal to those in Table 2.

TABLE 7

Composition of succinic acid concentrated liquid

| Component | Extract phase | Concentrated liquid |
|---|---|---|
| | Composition (% by weight) | |
| Succinic acid | 4.51 | 29.7 |
| Malic acid | 0.19 | 1.24 |
| Pyruvic acid | 0.00 | 0.00 |
| Acetic acid | 0.92 | 6.03 |
| Fumaric acid | 0.12 | 0.81 |
| α-Ketoglutaric acid | 0.01 | 0.05 |
| α-Ketovaline | 0.02 | 0.15 |
| Alanine | 0.00 | 0.01 |
| Valine | 0.00 | 0.01 |
| Glutamic acid | 0.00 | 0.00 |
| Trehalose | 0.00 | 0.00 |

TABLE 7-continued

Composition of succinic acid concentrated liquid

| Component | Extract phase | Concentrated liquid |
|---|---|---|
| | Composition (% by weight) | |
| Protein | 0.01 | 0.08 |
| MEK | 81.0 | 03 |
| Water | 13.2 | — |

<Crystallization>

Crystallization was carried out in the same method as that in Referential Example 2, thereby recovering 113 g of succinic acid and 568 g of a recovered liquid that is a mixed liquid of a crystallization mother liquid and washings. A composition of the resulting succinic acid is shown in the following Table 8, and a composition of the resulting recovered liquid is shown in the following Table 9. The analysis of each of the organic acid and the sugar was carried out by means of high-performance liquid chromatography under conditions equal to those in Table 2.

TABLE 8

Composition of obtained succinic acid

| Component | Composition (% by weight) |
|---|---|
| Succinic acid | 95.9 |
| Malic acid | 0.0 |
| Pyruvic acid | 0.0 |
| Acetic acid | 0.1 |
| Fumaric acid | 3.1 |
| α-Ketoglutaric acid | 0.0 |
| α-Ketovaline | 0.0 |
| Alanine | 0.0 |
| Valine | 0.0 |
| Glutamic acid | 0.0 |
| Trehalose | 0.0 |
| Protein | 18 ppm |
| MEK | 0.0 |
| Water | 0.8 |

Recovered succinic acid/newly fed succinic acid: 113 × 0.959/(1,384 × 0.0865) = 91%

TABLE 9

Composition of recovered liquid

| Component | Composition (% by weight) |
|---|---|
| Succinic acid | 3.63 |
| Malic acid | 0.95 |
| Pyruvic acid | 0.00 |
| Acetic acid | 4.62 |
| Fumaric acid | 0.01 |
| α-Ketoglutaric acid | 0.04 |
| α-Ketovaline | 0.11 |
| Alanine | 0.01 |
| Valine | 0.01 |
| Glutamic acid | 0.00 |
| Trehalose | 0.00 |
| Protein | 0.06 |
| MEK | 0.02 |

<Highly Purification>

A 30 wt % crude succinic acid aqueous solution was prepared from the above-obtained crude crystal at 80° C., and a chemically activated, powdered activated carbon Diahope 8ED (manufactured by Calgon Mitsubishi Chemical Corporation) was then added in an amount of 0.3 wt % relative to the succinic acid. The activated carbon treatment was carried out at 80° C. for 2 hours with stirring at 200 rpm using a three-one motor.

After filtering out the activated carbon at 80° C., the resulting succinic acid aqueous solution was charged in an SUS 316-made 500-mL induction stirring autoclave and subjected to a hydrogen treatment in the presence of 5 PdJC (Wako's catalogue 326-81672, catalyst amount: 0.06 wt % relative to succinic acid) under a condition at a hydrogen pressure of 0.8 MPa at a reaction temperature of 80° C. for a reaction time of 3 hours. As a result, fumaric acid contained in an amount of 1.3% by weight relative to succinic acid in crude succinic acid was entirely derived into succinic acid. After completion of the reaction, the catalyst was filtered out. The hydrogen treatment solution was substantially free from an odor.

This hydrogen-treated succinic acid aqueous solution was subjected to an ion exchange treatment (cation exchange resin (Diaion SK1B-H (manufactured by Mitsubishi Chemical Corporation): H type) at 80° C., thereby removing cations having been contained in a trace amount.

The ion exchange-treated succinic acid aqueous solution was cooled to 20° C. with stirring for about 90 minutes and further kept at 20° C. for one hour to deposit a crystal. The deposited succinic acid was recovered by means of filtration, and the crystal was washed with cold water and then dried in vacuo at 70° C. for 12 hours to obtain white odorless succinic acid (YI=−1).

In the resulting succinic acid, the concentrations of Na, K, Mg, Ca and $NH_4$ ions were all not more than 1 ppm; the sulfur atom content was less than 1 ppm; and the nitrogen atom content was 2 ppm. In addition, a succinic acid aqueous solution having a concentration of the resulting succinic acid of 3.0 wt % was prepared, a spectrum of which was then measured using a Hitachi's spectrophotometer Hitachi UV-3500. As a result, its average absorbance at 250 to 300 nm was not more than 0.01.

Example 1

Production of Polyester Polyol

In a one-liter four-necked flask installed with a thermometer, an induction stirrer, a condenser-equipped oil-water separator, and a dropping funnel, 260 g (2.2 moles) of succinic acid having a content of malic acid of 0.2 ppm (prepared by purifying succinic acid as produced by the fermentation method) and 296 g (2.5 moles) of 3-methyl-1,5-pentanediol as a polyhydric alcohol were charged. Thereafter, operations of pressure reduction to 30 Torr and pressure return with nitrogen were repeated several times, thereby substituting the inside of the reactor with nitrogen.

The temperature was increased to 145° C. while stirring the reaction mixture, and stirring was kept at that temperature for 30 minutes. At that time, since formed water started to come out, the removal of water formed from the condenser-equipped oil-water separator was started. Thereafter, the temperature was increased to 220° C. over about one hour. Thereafter, 15 mL of toluene was added from the dropping funnel, the pressure was further reduced to about 600 Torr, and the removal of formed water was continued so as to reflux toluene through the condenser-equipped oil-water separator.

15 minutes after starting the pressure reduction, 0.53 mL of a tetraisopropoxy titanium (TPT) 5 wt/vol % toluene solution was added. Thereafter, when it was confirmed that the acid number became not more than 0.50 KOH-mg/g, the reaction was completed.

After completion of the reaction, the temperature was decreased to 160° C., the pressure was further reduced finally to 20 Torr to completely distil off the toluene, and a hydroxyl number of the contents in the flask was measured. For the purpose of obtaining a polyester polyol having a number average molecular weight of 2,000, in the case where the hydroxyl number is larger than 56.0, the removal of the diol was further carried out; whereas in the case where the hydroxyl number is smaller than 56.0, the raw material polyhydric alcohol was added so as to correspond to the hydroxyl number of 56.0, and superheating was carried out with stirring at 220° C. for an arbitrary period of time to achieve a depolymerization reaction, thereby regulating the hydroxyl number to about 56.0. As a result, a polyester polyol having a hydroxyl number of 54.9 (hydroxyl number-calculated molecular weight: 2,044) was produced. The resulting polyester polyol had an APHA of 20.

The hydroxyl number-calculated molecular weight as referred to herein was calculated in the following manner while considering the polyol as a diol.

Hydroxyl number-calculated molecular weight=[Molecular weight of KOH (g/mole)]/[Hydroxyl number (mg-KOH/g)]×1,000×2

<NMR Measuring Method of Polyester Polyol>

43.3 mg of a polyester polyol sample was dissolved in 0.7 mL of deuteriochloroform (containing 0.05 v/v TMS) and then transferred into an NMR sample tube having an outside diameter of 5 mm. A 1H-NMR spectrum was measured at room temperature using an AVANCE 400 spectrometer, manufactured by Bruker. As a standard of the chemical shift, a signal of TMS was defined as 0.00 ppm. In the measurement of an amount of malic acid in the succinic acid unit of the polyester polyol, a peak of the maleate is detected at 5.43 ppm. In the case of S/N=3, a detection limit was 500 ppm relative to the succinic acid unit.

In consequence, since the charge amount of the malic acid unit relative to the raw material succinic acid unit was 0.2 ppm, and in the foregoing NMR measurement, the detection limit of malic acid was 500 ppm, and hence, the malic acid unit was not detected.

<Polyurethane Production 1>

In a one-liter separable flask, 102.2 g of the polyester polyol produced by the foregoing method (number average molecular weight calculated from the hydroxyl number: about 2,000) was charged and dissolved in N,N-dimethylformamide (DMF) by dipping the flask on an oil bath set at 55° C. while heating. Stirring was started at about 100 rpm, 4.51 g of 1,4-butanediol was further added as a chain extender, and 0.024 g of tin octylate was dropped.

Subsequently, diphenylmethane diisocyanate (MDI) was dropped at a rate such that the reaction liquid temperature did not exceed 70° C. Thereafter, MDI was gradually dropped to achieve chain extension, and finally, 25.3 g (1.01 equivalents to the polyol hydroxyl group) of MDI was added. When it was confirmed that the weight average molecular weight exceeded 100,000 by the GPC measurement, the reaction was completed to obtain a DMF solution of polyurethane having a solid content of 30%. The resulting polyurethane revealed target results such that a weight average molecular weight was 139,000, and a molecular weight distribution Mw/Mn was 2.1.

<NMR Measuring Method of Polyurethane>

About 40 mg of a polyurethane sample was weighed in an NMR sample tube having an outside diameter of 5 mm and dissolved in about 1.0 mL of DMF-d7. A 1H-NMR spectrum was measured at room temperature using an AVANCE 400 spectrometer, manufactured by Bruker. As a standard of the chemical shift, a signal on the low magnetic field side of a methyl group of DMF was defined as 2.91 ppm. In the measurement of an amount of malic acid in the succinic acid unit of the polyurethane, a peak of the maleate is detected at 5.46 ppm. In the case of S/N=3, a detection limit was 300 ppm relative to the succinic acid unit. In consequence, since the charge amount of the malic acid unit relative to the raw material succinic acid unit was 0.2 ppm, and in the foregoing NMR measurement, the detection limit of malic acid was 300 ppm, and hence, the malic acid unit was not detected.

<Fabrication of Sample for Evaluating Polyurethane Physical Properties>

The resulting polyurethane solution was used and coated in a uniform film thickness on a polyethylene film using a doctor blade, followed by drying by a dryer to obtain a polyurethane film. A tensile strength test of this film was carried out according to the foregoing measuring methods of film physical properties. As to the physical properties, the urethane film had a stress at break of 7.9 MPa and had a low elastic modulus such that an elongation at break was 1,270%, thereby revealing very excellent physical properties in elongation.

Comparative Example 1

A polyester polyol having a hydroxyl number of 55.1 (hydroxyl number-calculated molecular weight: 2,036) was produced by the above-described polyester polyol production method by using, as raw materials, 260 g (2.2 moles) of succinic acid having a content of malic acid of 5,000 ppm (using commercially available succinic acid as produced from maleic anhydride as a raw material) and 296 g (2.5 moles) of 3-methyl-1,5-pentanediol as a polyhydric alcohol. This polyester polyol had an APHA of 20. As a result of the NMR measurement, an amount of a malic acid unit, namely a crosslinking structure, was 0.47% by mole relative to a succinic acid unit.

A polyurethane was produced in the above-described production method of Polyurethane Production 1 by using 101.8 g of the foregoing polyester polyol as a raw material, 4.51 g of 1,4-butanediol as a chain extender, and 25.2 g (1.01 equivalents to the hydroxyl group) of diphenylmethane diisocyanate (MDI).

The resulting polyurethane had a weight average molecular weight of 410,000 and a molecular weight distribution Mw/Mn of 3.2 and revealed results that both the molecular weight and the molecular weight distribution were unexpectedly large. As a result of the NMR measurement, an amount of a malic acid unit, namely a crosslinking structure, was 0.52% by mole relative to a succinic acid unit. In addition, the urethane film had a stress at break of 9.9 MPa and had a high elastic modulus such that an elongation at break was 910%, thereby revealing low physical properties in elongation.

Comparative Example 2

A polyester polyol having a hydroxyl number of 54.1 (hydroxyl number-calculated molecular weight: 2,074) was produced by the above-described polyester polyol production method by using, as raw materials, 260 g (2.2 moles) of succinic acid having a content of malic acid of 1,700 ppm (succinic acid prepared by purifying a product produced from maleic anhydride as a raw material was used) and 296 g (2.5 moles) of 3-methyl-1,5-pentanediol as a polyhydric alcohol. This polyester polyol had an APHA of 20. As a result of the NMR measurement, an amount of a malic acid unit, namely a crosslinking structure, was 0.16% by mole relative to a succinic acid unit.

A polyurethane was produced in the above-described production method of Polyurethane Production 1 by using 103.7 g of the foregoing polyester polyol as a raw material, 4.51 g of 1,4-butanediol as a chain extender, and 25.3 g (1.01 equivalents to the hydroxyl group) of diphenylmethane diisocyanate (MDI).

The resulting polyurethane had a weight average molecular weight of 320,000 and a molecular weight distribution Mw/Mn of 2.8 and revealed results that both the molecular weight and the molecular weight distribution were unexpectedly large. As a result of the NMR measurement, an amount of a malic acid unit, namely a crosslinking structure, was 0.19% by mole relative to a succinic acid unit. In addition, in this urethane solution, the weight average molecular weight abnormally increased to 490,000 at the time of film fabrication, and hence, the evaluation was discontinued.

Example 2

A polyester polyol having a hydroxyl number of 61.0 (hydroxyl number-calculated molecular weight: 1,839) was produced in the same method as that in Example 1, except for using, as raw materials, 71 g (0.6 moles) of succinic acid having a content of malic acid of 0.2 ppm (prepared by purifying succinic acid as produced by the fermentation method), 88 g (0.6 moles) of adipic acid (commercially available product), and 162 g (1.4 moles) of 3-methyl-1,5-pentanediol as a polyhydric alcohol. This polyester polyol had an APHA of 25, and even when mixed with a petroleum-derived dicarboxylic acid, a polyester polyol with less coloration was obtained.

Example 3

A polyester polyol having a hydroxyl number of 56.9 (hydroxyl number-calculated molecular weight: 1,972) was produced in the same method as that in Example 1, except for using, as raw materials, 160 g (1.4 moles) of succinic acid having a content of malic acid of 500 ppm (prepared by adding malic acid to succinic acid as produced by the fermentation method) and 179 g (1.5 moles) of 3-methyl-1,5-pentanediol as a polyhydric alcohol; and setting an upper limit of the reaction temperature to about 190° C.

<Polyurethane Production 2>

In a one-liter separable flask, 56.8 g of the polyester polyol produced by the foregoing method (number average molecular weight calculated from the hydroxyl number: about 2,000) was charged and substituted with nitrogen three times. Thereafter, the pressure was reduced to 20 Torr, and the flask was dipped on an oil bath at 100° C. to achieve dehydration for one hour. After lapsing one hour, the system was once cooled, and the pressure was returned with nitrogen. At that time, a water content of the polyester polyol was 110 ppm. Subsequently, the flask was dipped on an oil bath at 60° C., and N,N-dimethylacetamide (DMAc) was added and dissolved while heating. Stirring was started at about 100 rpm, 2.55 g of 1,4-butanediol was further added as a chain extender, and 0.012 g of tin octylate was dropped. At that time, the water content was 0.025 g (0.0014 moles) in total in the polyester polyol and the solvent.

In the polyurethane reaction, since MDI is consumed by water contained in the system, the addition amount of MDI was determined taking into consideration the water content. The water content after dehydrating the polyol and the water content contained in the used solvent were measured, and MDI was added through calculation such that its addition amount was 100% relative to the hydroxyl group number of the polyester polyol and the chain extender and the active hydrogen number contained in the measured water content (MDI equivalent to the active hydrogen).

That is, the MDI equivalent to the active hydrogen is expressed by the following equation.

MDI equivalent relative to active hydrogen=(NCO [mole])/{(Hydroxyl group number of polyester polyol [mole])+(Hydroxyl group number of chain extender [mole])+(Water content in polyester polyol [mole])+(Water content in solvent [mole])}

Diphenylmethane diisocyanate (MDI) was dropped at a rate such that the reaction liquid temperature did not exceed 70° C. Thereafter, MDI was gradually dropped to achieve chain extension, and finally, 14.4 g (1.00 equivalent to the active hydrogen) of MDI was added. When it was confirmed that the weight average molecular weight exceeded 100,000 by the GPC measurement, the reaction was completed, thereby obtaining a DMAc solution of polyurethane having a solid content of 30%.

The resulting polyurethane revealed results such that a weight average molecular weight was 188,000, and a molecular weight distribution Mw/Mn was 2.0. In addition, as to the physical properties, the urethane film had a stress at break of 8.5 MPa. In addition, in the case of producing a polyurethane in the same method as Polyurethane Production 2, except that in the foregoing polyurethane reaction, 14.5 g (1.01 equivalents to the active hydrogen) of diphenylmethane diisocyanate (MDI) was used, and the resulting polyurethane revealed results such that a weight average molecular weight was 258,000, and a molecular weight distribution Mw/Mn was 2.2. Thus, a polyurethane having a desired molecular weight was easily obtainable without causing gelation.

Example 4

A polyester polyol having a hydroxyl number of 52.6 (hydroxyl number-calculated molecular weight: 2,133) was produced in the same method as that in Example 1, except for using, as raw materials, 160 g (1.4 moles) of succinic acid having a content of malic acid of 0.2 ppm (prepared by purifying succinic acid as produced by the fermentation method) and 178 g (1.5 moles) of 3-methyl-1,5-pentanediol as a polyhydric alcohol.

A polyurethane was produced in the above-described production method of Polyurethane Production 2 by using 60.2 g of the foregoing polyester polyol as a raw material, 2.54 g of 1,4-butanediol as a chain extender, and 14.2 g (1.00 equivalent to the active hydrogen) of diphenylmethane diisocyanate (MDI). At that time, the water content was 0.014 g (0.00078 moles) in total in the polyester polyol and the solvent. The resulting polyurethane revealed target results such that a weight average molecular weight was 160,000, and a molecular weight distribution Mw/Mn was 2.0. In addition, as to the physical properties, the urethane film had a stress at break of 5.5 MPa.

In addition, in the case of producing a polyurethane in the same method as Polyurethane Production 2, except that in the foregoing polyurethane reaction, 14.3 g (1.01 equivalents to the active hydrogen) of diphenylmethane diisocyanate (MDI) was used, and the resulting polyurethane revealed results such that a weight average molecular weight was 201,000, and a molecular weight distribution Mw/Mn was 2.0. Thus, a polyurethane having a desired molecular weight was easily obtainable without causing gelation.

Comparative Example 3

A polyester polyol having a hydroxyl number of 55.2 (hydroxyl group-calculated molecular weight: 2,033) was produced in the same method as that in Example 1, except for using, as raw materials, 160 g (1.4 moles) of succinic acid having a content of malic acid of less than the detection limit (succinic acid prepared by further crystallization and purification of succinic acid having a malic acid content of 0.2 ppm as produced by the fermentation method, thereby making the malic acid content less than the detection limit relative to succinic acid by LC-MS, was used) and 177 g (1.5 moles) of 3-methyl-1,5-pentanediol as a polyhydric alcohol; and setting an upper limit of the reaction temperature to about 190° C.

A polyurethane was produced in the above-described production method of Polyurethane Production 2 by using 58.9 g of the foregoing polyester polyol as a raw material, 2.61 g of 1,4-butanediol as a chain extender, and 14.7 g (1.00 equivalent to the active hydrogen) of diphenylmethane diisocyanate (MDI). At that time, the water content in the system was 0.028 g (0.0016 moles) in total in the polyester polyol and the solvent.

The resulting polyurethane had a weight average molecular weight was 146,000, and a molecular weight distribution Mw/Mn of 2.1 and revealed results that the molecular weight hardly increased. In addition, the urethane film had a stress at break of 5.3 MPa, so that a polyurethane with sufficient mechanical strength was not obtained.

Comparative Example 4

A polyester polyol having a hydroxyl number of 56.3 (hydroxyl number-calculated molecular weight: 1,993) was produced in the same method as that in Example 1, except for using, as raw materials, 159 g (1.4 moles) of succinic acid having a content of malic acid of 5,000 ppm (succinic acid prepared by adding malic acid to succinic acid as produced by the fermentation method was used) and 178 g (1.5 moles) of 3-methyl-1,5-pentanediol as a polyhydric alcohol; and setting an upper limit of the reaction temperature to about 190° C.

A polyurethane was produced in the above-described production method of Polyurethane Production 2 by using 60.7 g of the foregoing polyester polyol as a raw material, 2.75 g of 1,4-butanediol as a chain extender, and 15.4 g (1.00 equivalent to the active hydrogen) of diphenylmethane diisocyanate (MDI). At that time, the water content in the system was 0.025 g (0.0014 moles) in total in the polyester polyol and the solvent. The resulting polyurethane had a weight average molecular weight of 375,000 and a molecular weight distribution Mw/Mn of 3.2 and revealed results that both the molecular weight and the molecular weight distribution were unexpectedly large. As a result of the NMR measurement, a stress at break of the urethane film was 14.4 MPa.

In addition, in the case of producing a polyurethane in the same method, except that in the foregoing polyurethane reaction, 15.6 g (1.01 equivalents to the active hydrogen) of diphenylmethane diisocyanate (MDI) was used, the polyurethane caused gelation.

That is, in the case of producing a polyester polyol using succinic acid containing 5,000 ppm of malic acid and subsequently producing a polyurethane, the molecular weight largely increases relative to the addition and operation amount of MDI, resulting in danger of causing gelation. Thus, results that it is difficult to obtain a polyurethane having a desired molecular weight were revealed.

The results of Examples 3 to 4 and Comparative Examples 3 to 4 are shown in Table 10.

TABLE 10

| | Amount of malic acid in raw material succinic acid [ppm] | Molecular weight of polyurethane [Mw] | | Stress at break of polyurethane [MPa] |
|---|---|---|---|---|
| | | MDI: 1.00 equivalent | MDI: 1.01 equivalents | MDI: 1.00 equivalent |
| Comparative Example 3 | Less than detection limit | 146,000 | — | 5.3 |
| Example 4 | 0.2 | 160,000 | 201,000 | 5.5 |
| Example 3 | 500 | 188,000 | 258,000 | 8.5 |
| Comparative Example 4 | 5,000 | 375,000 | (Gelated) | 14.4 |

Example 5

Production 2 of Polyester Polyol

In a one-liter four-necked flask installed with a thermometer, an induction stirrer, a condenser-equipped oil-water separator, and a dropping funnel, 170 g (1.5 moles) of succinic acid having a content of malic acid of 0.2 ppm (prepared by purifying succinic acid as produced by the fermentation method), 110 g (1.8 moles) of ethylene glycol as a polyhydric alcohol, and 80 g (0.9 moles) of 1,4-butanediol were charged. Thereafter, operations of pressure reduction to 30 Torr and pressure return with nitrogen were repeated several times, thereby substituting the inside of the reactor with nitrogen.

The temperature was increased to 145° C. while stirring the reaction mixture, and stirring was kept at that temperature for 30 minutes. At that time, since formed water started to come out, the removal of water formed from the condenser was started. Thereafter, the temperature was increased to 190° C. over about one hour. After the temperature increase, 0.35 mL of a tetraisopropoxy titanium (TPT) 5 wt/vol % toluene solution was added. The pressure of the reactor was reduced from ordinary pressure to 20 Torr over about 2 hours, thereby removing a prescribed amount of the excessive diol together with water. Thereafter, when it was confirmed that the acid number became not more than 1.0 KOH-mg/g, the reaction was completed.

After completion of the reaction, the temperature was decreased to 160° C., and a hydroxyl number of the contents in the flask was measured. For the purpose of obtaining a polyester polyol having a number average molecular weight of 2,000, in the case where the hydroxyl number is large than 56.0, the removal of the diol was further carried out; whereas in the case where the hydroxyl number is smaller than 56.0, the raw material polyhydric alcohol was added so as to correspond to the hydroxyl number of 56.0, and superheating was carried out with stirring at 190° C. for an arbitrary period of time to achieve a depolymerization reaction, thereby regulating the hydroxyl number to about 56.0. As a result, a polyester polyol having a hydroxyl number of 55.8 (hydroxyl number-calculated molecular weight: 2,011) was produced.

A polyurethane was produced in the above-described production method of Polyurethane Production 2, except for using 58.8 g of the foregoing polyester polyol as a raw material, 2.63 g of 1,4-butanediol as a chain extender, and 14.8 g (1.00 equivalent to the active hydrogen) of diphenylmethane diisocyanate (MDI) and using DMF as a solvent. At that time, the water content was 0.029 g (0.0016 moles) in total in the polyester polyol and the solvent. The resulting polyurethane revealed target results such that a weight average molecular weight was 198,000, and a molecular weight distribution Mw/Mn was 2.0. Also, an abnormal increase of the molecular weight was not observed, and excellent production stability was revealed.

From the foregoing results, as shown in the present Comparative Examples, it has been noted that in the case of producing a polyester polyol using, as a raw material, a dicarboxylic acid having a content of an organic acid having a pKa value of not more than 3.7 of more than 1,000 ppm and producing a polyurethane using this polyester polyol, since the produced polyester polyol and polyurethane have a crosslinking structure, gelation and abnormal molecular weight increase occur at the time of polyisocyanate reaction due to the crosslinking structure, and hence, control of the reaction is difficult. Furthermore, it has been noted that physical properties of the resulting polyurethane are rigid and low in elongation.

In addition, as shown in the present Comparative Examples, it has been noted that in the case of producing a polyester polyol using a dicarboxylic acid having a content of an organic acid having a pKa value of not more than 3.7 of 0 ppm (less than a detection limit) and producing a polyurethane using this polyester polyol, molecular weights of the produced polyester polyol and polyurethane do not sufficiently increase, and the mechanical strength of the resulting polyurethane is lowered.

On the other hand, as shown in the present Examples, it has been noted that in the case of producing a polyester polyol using, as a raw material, a dicarboxylic acid having a content of an organic acid having a pKa value of not more than 3.7 of more than 0 ppm and not more than 1,000 ppm and producing a polyurethane using this polyester polyol, since a crosslinking structure appropriately relies upon the produced polyester polyol and polyurethane, not only the molecular weight or the like is easily controllable at the time of polyisocyanate reaction, but a polyurethane with sufficient mechanical strength is obtained.

It has hitherto been considered that in a polyester polyol using, as a raw material, succinic acid as the dicarboxylic acid, the reaction control is difficult at the time of polyurethane reaction, and physical properties of a polyurethane using it are rigid and low in elongation. However, by using certain specified succinic acid as a raw material, it has now been astonishingly noted that even when succinic acid is used as the raw material, the reaction control is possible, and furthermore, a polyurethane having sufficient mechanical strength can be produced.

While the present invention has been described in detail and with reference to specific embodiments thereof, it will be apparent to one skilled in the art that various changes and modifications can be made therein without departing from the spirit and scope thereof. Incidentally, the present application is based on a Japanese patent application, filed Mar. 31, 2010

(Japanese Patent Application No. 2010-082393), the entire contents of which are incorporated therein and made hereof by reference.

INDUSTRIAL APPLICABILITY

Since a biomass-resource-derived polyurethane using, as a raw material, a biomass-resource-derived polyester polyol according to the present invention is easily controllable in the reaction and low in its solution viscosity, it is good in operability and is easily cast and coated. Thus, it can be used for wide-range polyurethane applications.

Furthermore, since the polyurethane of the present invention is derived from environmentally friendly plants while keeping mechanical strengths such as abrasion resistance, flexibility resistance, etc. as characteristics as conventional polyester polyol-derived polyurethanes, it is expected that the present invention is industrially extremely useful.

The invention claimed is:

1. A biomass-resource-derived polyurethane, comprising, in reacted form:
   (I) a polyester polyol unit having a number average molecular weight of 500 to 4,000 and comprising, in reacted form:
      an organic acid comprising three or more active hydrogen groups per molecule and having a pKa value at 25° C. of not more than 3.7;
      a dicarboxylic acid unit comprising a dicarboxylic acid other than the organic acid, wherein at least a portion of the dicarboxylic acid is derived from biomass resources; and
      an aliphatic diol unit,
      wherein a content of the organic acid is more than 0% by mole and not more than 0.09% by mole relative to the dicarboxylic acid unit; and
   (II) a polyisocyanate unit.

2. The biomass-resource-derived polyurethane of claim 1, wherein the dicarboxylic acid comprises succinic acid derived from biomass resources.

3. The biomass-resource-derived polyurethane of claim 1, wherein the aliphatic diol unit comprises an ethylene glycol unit, a 1,4-butanediol unit, or both.

4. The biomass-resource-derived polyurethane of claim 1, wherein the organic acid is malic acid, tartaric acid, citric acid, or any combination thereof.

5. The biomass-resource-derived polyurethane of claim 1, having a YI value (in conformity with JIS-K7105) of not more than 20.

6. The biomass-resource-derived polyurethane of claim 1, having a molecular weight distribution, Mw/Mn, from 1.5 to 3.5, determined by the GPC measurement.

* * * * *